(12) United States Patent
Manchester et al.

(10) Patent No.: US 10,544,390 B2
(45) Date of Patent: Jan. 28, 2020

(54) METHODS FOR GENERATING A BACTERIAL HEMOGLOBIN LIBRARY AND USES THEREOF

(71) Applicant: Zymergen Inc., Emeryville, CA (US)

(72) Inventors: Shawn Manchester, Oakland, CA (US); Alexander Neckelmann, Emeryville, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

(21) Appl. No.: 16/313,612

(22) PCT Filed: Jun. 28, 2017

(86) PCT No.: PCT/US2017/039772
§ 371 (c)(1),
(2) Date: Dec. 27, 2018

(87) PCT Pub. No.: WO2018/005655
PCT Pub. Date: Jan. 4, 2018

(65) Prior Publication Data
US 2019/0194599 A1    Jun. 27, 2019

Related U.S. Application Data

(60) Provisional application No. 62/356,934, filed on Jun. 30, 2016.

(51) Int. Cl.
*C07K 14/805* (2006.01)
*C12N 15/70* (2006.01)
(Continued)

(52) U.S. Cl.
CPC .............. *C12N 1/20* (2013.01); *C07K 14/805* (2013.01); *C12N 15/70* (2013.01); *C12N 15/74* (2013.01); *C12R 1/15* (2013.01); *C40B 30/06* (2013.01)

(58) Field of Classification Search
CPC .............. C12N 15/1037; C12N 9/1205; C12N 2800/22; C12N 15/77; C12N 1/20;
(Continued)

(56) References Cited

U.S. PATENT DOCUMENTS

| 4,435,504 A | 3/1984 | Zuk et al. |
| 4,489,160 A | 12/1984 | Katsumata et al. |

(Continued)

FOREIGN PATENT DOCUMENTS

| DE | 19548222 A1 | 6/1997 |
| DE | 19831609 A1 | 4/1999 |

(Continued)

OTHER PUBLICATIONS

"Designing a Million Genomes: Machine Learning, Automation and Biotech.", Strata + Hadoop World, Make Data Work conference, London, UK, May 5, 2015; https://www.youtube.com/watch?v=658kvYgrJBE&feature=youtu.be, Published on Oct. 7, 2015, Business-focused talk at Strata UK 2015 by Aaron Kimball, CTO of Zymergen Inc.

(Continued)

*Primary Examiner* — Jeremy C Flinders
(74) *Attorney, Agent, or Firm* — Cooley LLP

(57) ABSTRACT

The present disclosure describes methods for generating microbial strains expressing a heterologous bacterial hemoglobin gene that produce biomolecules of interest. In aspects, the disclosure provides novel bacterial strains, which express a heterologous bacterial hemoglobin gene whose expression is controlled by a native *Corynebacterium glutamicum* promoter or a mutant promoter derived therefrom. Also provided herein are methods for producing a library of bacterial hemoglobin genes using a promoter (Continued)

US 10,544,390 B2

Page 2 ladder comprising a plurality of promoters derived from *Corynebacterium glutamicum*.

20 Claims, 5 Drawing Sheets

Specification includes a Sequence Listing.

(51) Int. Cl.
    *C12N 15/74* (2006.01)
    *C12R 1/15* (2006.01)
    *C12N 1/20* (2006.01)
    *C40B 30/06* (2006.01)

(58) Field of Classification Search
    CPC .............. C12N 15/70; C12N 15/74; C12Y 207/01069; C12Y 207/01001; C12Y 7/01002; C12P 1/04; C12P 21/02; C12P 19/02; C12P 19/30; C07K 1/047; C07K 14/805; C12R 1/15
    See application file for complete search history.

(56) References Cited

U.S. PATENT DOCUMENTS

| | | |
|---|---|---|
| 4,601,893 A | 7/1986 | Cardinal |
| 4,855,240 A | 8/1989 | Rosenstein et al. |
| 4,980,298 A | 12/1990 | Blake et al. |
| 5,158,891 A | 10/1992 | Takeda et al. |
| 5,275,940 A | 1/1994 | Kino et al. |
| 5,487,993 A | 1/1996 | Herrnstadt et al. |
| 5,516,670 A | 5/1996 | Kuehnle et al. |
| 5,591,645 A | 1/1997 | Rosenstein |
| 5,605,793 A | 2/1997 | Stemmer |
| 5,753,477 A | 5/1998 | Chan |
| 5,756,345 A | 5/1998 | Camakaris et al. |
| 5,770,409 A | 6/1998 | Pfefferle et al. |
| 5,811,238 A | 9/1998 | Stemmer et al. |
| 5,827,698 A | 10/1998 | Kikuchi et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 5,990,350 A | 11/1999 | Stevens et al. |
| 6,040,439 A | 3/2000 | Hayakawa et al. |
| 6,060,296 A | 5/2000 | Hoekstra |
| 6,090,592 A | 7/2000 | Adams et al. |
| 6,117,679 A | 9/2000 | Stemmer et al. |
| 6,136,565 A | 10/2000 | Best et al. |
| 6,174,673 B1 | 1/2001 | Short et al. |
| 6,251,674 B1 | 6/2001 | Tobin et al. |
| 6,287,862 B1 | 9/2001 | delCardayre et al. |
| 6,300,070 B1 | 10/2001 | Boles et al. |
| 6,326,204 B1 | 12/2001 | delCardayre et al. |
| 6,335,160 B1 | 1/2002 | Paatten et al. |
| 6,335,198 B1 | 1/2002 | delCardayre et al. |
| 6,352,859 B1 | 3/2002 | delCardayre et al. |
| 6,358,709 B1 | 3/2002 | Short et al. |
| 6,379,964 B1 | 4/2002 | del Cardayre et al. |
| 6,479,258 B1 | 11/2002 | Short |
| 6,528,311 B1 | 3/2003 | delCardayre et al. |
| 6,586,214 B1 | 7/2003 | Dunican et al. |
| 6,605,449 B1 | 8/2003 | Short |
| 6,713,279 B1 | 3/2004 | Short |
| 6,716,631 B1 | 4/2004 | delCardayre et al. |
| 6,759,195 B1 | 7/2004 | Bentley et al. |
| 6,759,218 B2 | 7/2004 | Mockel et al. |
| 7,033,781 B1 | 4/2006 | Short |
| 7,115,400 B1 | 10/2006 | Adessi et al. |
| 7,118,904 B2 | 10/2006 | Mockel et al. |
| 7,127,379 B2 | 10/2006 | Palsson et al. |
| 7,138,266 B2 | 11/2006 | Debabov et al. |
| 7,148,054 B2 | 12/2006 | delCardayre et al. |
| 7,507,574 B2 | 3/2009 | Bill et al. |
| 7,510,854 B2 | 3/2009 | Pompejus et al. |
| 7,629,170 B2 | 12/2009 | delCardayre et al. |
| 7,711,490 B2 | 5/2010 | Maranas et al. |
| 7,826,975 B2 | 11/2010 | Maranas et al. |
| 7,842,485 B2 | 11/2010 | Gill et al. |
| 7,846,688 B2 | 12/2010 | Gill et al. |
| 7,987,056 B2 | 7/2011 | Gill et al. |
| 8,076,138 B2 | 12/2011 | delCardayre et al. |
| 8,108,152 B2 | 1/2012 | Maranas et al. |
| 8,110,360 B2 | 2/2012 | Serber et al. |
| 8,221,982 B2 | 7/2012 | Serber et al. |
| 8,332,160 B1 | 12/2012 | Platt et al. |
| 8,349,587 B2 | 1/2013 | Fischer et al. |
| 8,377,681 B2 | 2/2013 | delCardayre et al. |
| 8,467,975 B2 | 6/2013 | Gill et al. |
| 8,476,041 B2 | 7/2013 | Cervin et al. |
| 8,530,203 B2 | 9/2013 | Ikeda et al. |
| 8,546,136 B2 | 10/2013 | Serber et al. |
| 8,685,737 B2 | 4/2014 | Serber et al. |
| 8,697,359 B1 | 4/2014 | Zhang |
| 8,741,603 B2 | 6/2014 | Han et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,883,464 B2 | 11/2014 | Lynch et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,388,419 B2 | 7/2016 | Lynch et al. |
| 9,428,778 B2 | 8/2016 | Lynch et al. |
| 9,506,087 B2 | 11/2016 | Vroom et al. |
| 9,506,167 B2 | 11/2016 | Shetty et al. |
| 9,580,719 B2 | 2/2017 | Retallack et al. |
| 9,637,739 B2 | 5/2017 | Siksnys et al. |
| 9,677,090 B2 | 6/2017 | Donohue et al. |
| 9,688,972 B2 | 6/2017 | May et al. |
| 9,701,971 B2 | 7/2017 | Serber et al. |
| 9,738,687 B2 | 8/2017 | Guay et al. |
| 9,745,562 B2 | 8/2017 | Donohue et al. |
| 9,752,176 B2 | 9/2017 | Kung et al. |
| 9,771,795 B2 | 9/2017 | Knight et al. |
| 9,790,490 B2 | 10/2017 | Zhang et al. |
| 9,816,081 B1 | 11/2017 | Donohue et al. |
| 9,822,372 B2 | 11/2017 | Zhang et al. |
| 9,840,713 B2 | 12/2017 | Zhang |
| 9,902,980 B2 | 2/2018 | Fischer et al. |
| 9,988,624 B2 | 6/2018 | Serber et al. |
| 10,047,358 B1 | 8/2018 | Serber et al. |
| 2002/0169562 A1 | 11/2002 | Stephanopoulos et al. |
| 2002/0197605 A1 | 12/2002 | Nakagawa et al. |
| 2003/0027175 A1 | 2/2003 | Stephanopoulos et al. |
| 2004/0077090 A1 | 4/2004 | Short |
| 2004/0101963 A1 | 5/2004 | Bibb et al. |
| 2005/0054106 A1 | 3/2005 | Ow et al. |
| 2005/0124010 A1 | 6/2005 | Short et al. |
| 2006/0019301 A1 | 1/2006 | Hansen et al. |
| 2006/0084098 A1 | 4/2006 | Gill et al. |
| 2006/0269975 A1 | 11/2006 | Pompejus et al. |
| 2006/0286574 A1 | 12/2006 | Romesberg et al. |
| 2007/0166792 A1 | 1/2007 | Olson et al. |
| 2007/0042474 A1 | 2/2007 | Pompejus et al. |
| 2007/0059768 A1 | 3/2007 | Gill et al. |
| 2007/0118916 A1 | 5/2007 | Puzio et al. |
| 2007/0122890 A1 | 5/2007 | Park et al. |
| 2007/0218533 A1 | 9/2007 | Gill et al. |
| 2007/0274972 A1 | 11/2007 | Muller et al. |
| 2007/0292918 A1 | 12/2007 | Stelman et al. |
| 2008/0103060 A1 | 5/2008 | Gill et al. |
| 2008/0243397 A1 | 10/2008 | Peccoud et al. |
| 2009/0221442 A1 | 9/2009 | Dower et al. |
| 2009/0253174 A1 | 10/2009 | Serber et al. |
| 2009/0280529 A1 | 11/2009 | Berg et al. |
| 2009/0325248 A1 | 12/2009 | Marx et al. |

(56) References Cited

U.S. PATENT DOCUMENTS

| | | |
|---|---|---|
| 2010/0048938 A1 | 2/2010 | Berg et al. |
| 2010/0105865 A1 | 4/2010 | Telford et al. |
| 2010/0124768 A1 | 5/2010 | Serber et al. |
| 2010/0136633 A1 | 6/2010 | Serber et al. |
| 2010/0137143 A1 | 6/2010 | Rothberg et al. |
| 2010/0210017 A1 | 8/2010 | Gill et al. |
| 2010/0216648 A1 | 8/2010 | Stahler et al. |
| 2010/0304982 A1 | 12/2010 | Hinz et al. |
| 2010/0317115 A1 | 12/2010 | Gill et al. |
| 2011/0054654 A1 | 3/2011 | Phillips et al. |
| 2011/0136688 A1 | 6/2011 | Scholl et al. |
| 2011/0172127 A1 | 7/2011 | Jacobsen et al. |
| 2011/0223638 A1 | 9/2011 | Wiedenheft et al. |
| 2011/0223671 A1 | 9/2011 | Yoder et al. |
| 2011/0244575 A1 | 10/2011 | Lipscomb et al. |
| 2011/0277179 A1 | 11/2011 | Puzio et al. |
| 2012/0070870 A1 | 3/2012 | Way et al. |
| 2012/0077681 A1 | 3/2012 | Gill et al. |
| 2012/0245056 A1 | 9/2012 | Serber et al. |
| 2012/0252681 A1 | 10/2012 | Del Cardayre et al. |
| 2012/0264902 A1 | 10/2012 | Lipscomb et al. |
| 2012/0277120 A1 | 11/2012 | Del Cardayre et al. |
| 2013/0071893 A1 | 3/2013 | Lynch et al. |
| 2013/0078709 A1 | 3/2013 | Franklin et al. |
| 2013/0122541 A1 | 5/2013 | Lynch et al. |
| 2013/0149742 A1 | 6/2013 | Bower et al. |
| 2013/0217132 A1 | 8/2013 | Gill et al. |
| 2013/0252240 A1 | 9/2013 | Cutler et al. |
| 2014/0045231 A1 | 2/2014 | Lynch et al. |
| 2014/0068797 A1 | 3/2014 | Doudna et al. |
| 2014/0172318 A1 | 6/2014 | Fisher et al. |
| 2014/0180660 A1 | 6/2014 | Clancy et al. |
| 2014/0186942 A1 | 7/2014 | Serber et al. |
| 2014/0295457 A1 | 10/2014 | Broenstrup et al. |
| 2014/0356921 A1 | 12/2014 | Deng et al. |
| 2015/0031100 A1 | 1/2015 | Gill et al. |
| 2015/0056651 A1 | 2/2015 | Lynch et al. |
| 2015/0056684 A1 | 2/2015 | Lipscomb et al. |
| 2015/0132263 A1 | 5/2015 | Liu et al. |
| 2015/0140626 A1 | 5/2015 | Song et al. |
| 2015/0211013 A1 | 7/2015 | Emalfarb et al. |
| 2015/0275224 A1 | 10/2015 | Basra et al. |
| 2015/0284810 A1 | 10/2015 | Knight et al. |
| 2015/0284811 A1 | 10/2015 | Knight et al. |
| 2015/0299742 A1 | 10/2015 | Gill et al. |
| 2015/0315599 A1 | 11/2015 | Shetty et al. |
| 2015/0344916 A1 | 12/2015 | Lynch et al. |
| 2015/0368639 A1 | 12/2015 | Gill et al. |
| 2015/0376628 A1 | 12/2015 | Schoenherr et al. |
| 2016/0046961 A1 | 2/2016 | Jinek et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0283651 A1 | 9/2016 | Knight et al. |
| 2016/0290132 A1 | 10/2016 | Knight et al. |
| 2016/0304905 A1 | 10/2016 | Hansen et al. |
| 2017/0009283 A1 | 1/2017 | Gill et al. |
| 2017/0051310 A1 | 2/2017 | Doudna et al. |
| 2017/0051312 A1 | 2/2017 | Jinek et al. |
| 2017/0067046 A1 | 3/2017 | Gill et al. |
| 2017/0073695 A1 | 3/2017 | Verruto et al. |
| 2017/0074889 A1 | 3/2017 | Shetty et al. |
| 2017/0114377 A1 | 4/2017 | Lynch et al. |
| 2017/0139078 A1 | 5/2017 | Knight et al. |
| 2017/0147742 A1 | 5/2017 | Jayaram et al. |
| 2017/0159045 A1 | 6/2017 | Serber et al. |
| 2017/0173086 A1 | 6/2017 | Boyle et al. |
| 2017/0240886 A1 | 8/2017 | Oleinikov |
| 2017/0240922 A1 | 8/2017 | Gill et al. |
| 2017/0240923 A1 | 8/2017 | Serber et al. |
| 2017/0316353 A1 | 11/2017 | Frewen et al. |
| 2017/0321198 A1 | 11/2017 | Severinov et al. |
| 2017/0321226 A1 | 11/2017 | Gill et al. |
| 2017/0342132 A1 | 11/2017 | Fraser et al. |
| 2017/0369870 A1 | 12/2017 | Gill et al. |
| 2017/0370213 A1 | 12/2017 | Knight et al. |
| 2018/0023120 A1 | 1/2018 | Kung et al. |
| 2018/0216099 A1 | 8/2018 | Serber et al. |
| 2018/0216100 A1 | 8/2018 | Serber et al. |
| 2018/0216101 A1 | 8/2018 | Serber et al. |
| 2018/0362991 A1 | 12/2018 | Serber et al. |

FOREIGN PATENT DOCUMENTS

| | | |
|---|---|---|
| DE | 19947791 A1 | 4/2001 |
| DE | 19950409 A1 | 4/2001 |
| DE | 19959327 A1 | 6/2001 |
| DE | 19959328 A1 | 6/2001 |
| EP | 0131171 A1 | 1/1985 |
| EP | 0238023 A2 | 9/1987 |
| EP | 0197335 B1 | 2/1991 |
| EP | 0472869 A2 | 3/1992 |
| EP | 0356739 B1 | 12/1995 |
| EP | 0743016 A | 11/1996 |
| EP | 0635574 B1 | 4/2003 |
| EP | 1790721 A1 | 5/2007 |
| EP | 0972081 B1 | 6/2007 |
| EP | 1546312 B1 | 7/2014 |
| JP | 01-225487 A | 9/1989 |
| KR | 1020080042823 A | 5/2008 |
| WO | WO 1989/003883 A1 | 5/1989 |
| WO | WO 1991/006628 A1 | 5/1991 |
| WO | WO 1992/003546 A1 | 3/1992 |
| WO | WO 1995/022625 A1 | 8/1995 |
| WO | WO 1996/015246 A1 | 5/1996 |
| WO | WO 1996/033207 A1 | 10/1996 |
| WO | WO 1998/031837 A1 | 7/1998 |
| WO | WO 2000/020555 A2 | 4/2000 |
| WO | WO 2001/012791 A1 | 2/2001 |
| WO | WO 2002/029032 A2 | 4/2002 |
| WO | WO 2003/014330 A2 | 2/2003 |
| WO | WO 2003/040373 A2 | 5/2003 |
| WO | WO 2004/054381 A1 | 7/2004 |
| WO | WO 2004/069996 A2 | 8/2004 |
| WO | WO 2005/006875 A2 | 1/2005 |
| WO | WO 2005/021772 A1 | 3/2005 |
| WO | WO 2006/069711 A1 | 7/2006 |
| WO | WO 2007/012078 A1 | 1/2007 |
| WO | WO 2007/015178 A2 | 2/2007 |
| WO | WO 2007/141580 A2 | 12/2007 |
| WO | WO 2009/025470 A2 | 2/2009 |
| WO | WO 2009/043803 A2 | 4/2009 |
| WO | WO 2009/126623 A2 | 10/2009 |
| WO | WO 2010/059763 A2 | 5/2010 |
| WO | WO 2010/075424 A2 | 7/2010 |
| WO | WO 2011/154147 A1 | 12/2011 |
| WO | WO 2012/082720 A2 | 6/2012 |
| WO | WO 2012/142591 A2 | 10/2012 |
| WO | WO 2012/149470 A1 | 11/2012 |
| WO | WO 2012/164565 A1 | 12/2012 |
| WO | WO 2013/066848 A1 | 5/2013 |
| WO | WO 2013/142578 A1 | 9/2013 |
| WO | WO 2014/011800 A1 | 1/2014 |
| WO | WO 2014/019527 A1 | 2/2014 |
| WO | WO 2014/089436 A1 | 6/2014 |
| WO | WO 2014/102782 A1 | 7/2014 |
| WO | WO 2015/070193 A1 | 5/2015 |
| WO | WO 2015/123339 A1 | 8/2015 |
| WO | WO 2015/148680 A1 | 10/2015 |
| WO | WO 2015/175793 A1 | 11/2015 |
| WO | WO 2006/028063 A1 | 3/2016 |
| WO | WO 2016/073690 A1 | 5/2016 |
| WO | WO 2016/196319 A1 | 12/2016 |
| WO | WO 2017/037304 A2 | 3/2017 |
| WO | WO 2017/100376 A2 | 6/2017 |
| WO | WO 2017/100377 A2 | 6/2017 |
| WO | WO 2017/189784 A1 | 11/2017 |
| WO | WO 2017/215790 A1 | 12/2017 |
| WO | WO 2017/223538 A1 | 12/2017 |
| WO | WO 2018/005655 A2 | 1/2018 |
| WO | WO 2018/005793 A1 | 1/2018 |

(56) References Cited

FOREIGN PATENT DOCUMENTS

| | | |
|---|---|---|
| WO | WO 2018/009372 A1 | 1/2018 |
| WO | WO 2018/013990 A1 | 1/2018 |
| WO | WO 2018/022972 A1 | 2/2018 |
| WO | WO 2018/071672 A1 | 4/2018 |

OTHER PUBLICATIONS

"The Data-Driven future of biotechnology." https://www.youtube.com/watch?v=IYmgJUHcG9g&feature=youtu.be&t=915, Strata + Hadoop World, NY Sep. 28-Oct. 1, 2015, Published on Nov. 15, 2015, Technical talk at Strata NY 2015 by Aaron Kimball, CTO of Zymergen Inc. about Zymergen's technology.

Adrio, Jose-Luis et al., "Recombinant organisms for production of industrial products", Bioengineered Bugs, 2010, pp. 116-131, vol. 1, No. 2.

Almeida, Elionor R.P., et al. "Transgenic expression of two marker genes under the control of an *Arabidopsis* rbcS promoter: Sequences encoding the Rubisco transit peptide increase expression levels." Molecular and General Genetics MGG (1989); 218.1: 78-86.

Alper et al., "Construction of lycopene-overproducing *E. coli* strains by combining systematic and combinatorial gene knockout targets." Nature Biotechnology (2005); 23 (5): 612-616.

Anonymous: "ABI 3900 High Throughput DNA Synthesizer", Mar. 1, 2001 (Mar. 1, 2001), URL:https://assets.thermofisher.com/TFS-Assets/LSG/manuals/cms_095580.pdf [retrieved on Jan. 2, 2018], 144 pages.

Askenazi, M., et al., "Integrating transcriptional and metabolite profiles to direct the engineering of lovastatin-producing fungal strains." Nat. Biotechnol. (2003); 21: 150-156.

Aslanidis, Charalampos, et al. "Ligation-independent cloning of PCR products (LIC-PCR)." Nucleic Acids Research (1990); 18.20: 6069-6074.

Azhayev, Alex V., et al. "Amide group assisted 3'-dephosphorylation of oligonucleotides synthesized on universal A-supports." Tetrahedron (2001); 57.23: 4977-4986.

Barcellos, Fernando Gomes, et al. "Genetic analysis of Aspergillus nidulans unstable transformants obtained by the biolistic process." Canadian Journal of Microbiology (1998); 44.12: 1137-1141.

Bartley, Bryan, et al. "Synthetic biology open language (SBOL) version 2.0. 0." Journal of Integrative Bioinformatics (JIB) (2015); 12(2): 902-991.

Beal, et al., "An End-to-End Workflow for Engineering of Biological Networks from High-Level Specifications." ACS Synth. Biol. (2012); 1 (8): 317-331. Publication Date (Web): Jul. 10, 2012.

Becker, Daniel M., and Guarente, Leonard. "[12] High-efficiency transformation of yeast by electroporation." Methods in Enzymology (1991); 194: 182-187.

Bentley, David R., et al. "Accurate whole human genome sequencing using reversible terminator chemistry." Nature (2008); 456.7218: 53-59.

Bernard, Philippe, et al. "The F plasmid CcdB protein induces efficient ATP-dependent DNA cleavage by gyrase." Journal of Molecular Biology (1993); 234.3: 534-541.

Bilitchenko, Al., "Eugene-a domain specific language for specifying and constraining synthetic biological parts, devices, and systems." PLOS ONE (2011); 6.4: e18882 (and Supplemental Data).

Boyd, J., et al. "Analysis of the diphtheria tox promoter by site-directed mutagenesis." Journal of Bacteriology (1988);170.12: 5949-5952.

Buchholz et al., "Platform Engineering of Corynebacterium glutamicum with Reduced Pyruvate Dehydrogenase Complex Activity for Improved Production of L-Lysine, L-Valine, and 2-Ketoisovalerate." Applied and Environmental Microbiology (2013); 79(18): 5566-5575.

Chakraborty, B. N., and Kapoor, M., "Transformation of filamentous fungi by electroporation." Nucleic Acids Research (1990); 18.22: 6737.

Chandran, et al., "TinkerCell: modular CAD tool for synthetic biology." Journal of Biological Engineering (2009); 3: 19, 17 pages.

Chen et al., "DeviceEditor visual biological CAD canvas." Journal of Biological Engineering (2012); 6:1, pp. 1-12.

Choi, J.H. et al., "Enhanced production of insulin-like growth factor I fusion protein in *Escherichia coli* by coexpression of the downregulated genes identified by transcriptome profiling." Appl. Environ. Microbiol. (2003); 69(8): 4737-4742.

Christiansen, Solveig K., et al. "Biolistic transformation of the obligate plant pathogenic fungus, *Erysiphe graminis* f. sp. hordei." Current Genetics (1995); 29.1: 100-102.

Christie, Peter J., and Gordon, Jay E. "The Agrobacterium Ti plasmids." Microbiology Spectrum (2014); 2.6.

Costanzo, Michael, et al. "The genetic landscape of a cell." Science (2010); 327 (5964): 425-431.

Cramer, Paula, et al. "Functional association between promoter structure and transcript alternative splicing." Proceedings of the National Academy of Sciences (1997); 94.21: 11456-11460.

Crameri, Andreas, et al. "Improved green fluorescent protein by molecular evolution using." Nat. Biotechnol (1996); 14.3: 315-319.

Crameri, Andreas, et al. "Construction and evolution of antibody-phage libraries by DMA shuffling." Nature Medicine (1996); 2.1: 100-102.

Crameri, Andreas, et al. "DNA shuffling of a family of genes from diverse species accelerates directed evolution." Nature (1998); 391.6664: 288-291.

Crameri, Andreas, et al. "Molecular evolution of an arsenate detoxification pathway by DNA shuffling." Nature Biotechnology (1997); 15.5: 436-438.

Czar, Michael J., et al. "Gene synthesis demystified." Trends in Biotechnology (2009); 27.2: 63-72.

Dahl, et al., "Multi-task Neural Networks for QSAR Predictions" Dept. of Computer Science, Univ. of Toronto, Jun. 2014, 21 pages (arXiv:1406.1231 [stat.ML]).

Dalphin, Mark E., et al. "TransTerm: A database of translational signals." Nucleic Acids Research (1996); 24.1: 216-218.

Damha, Masad J., et al. "An improved procedure for derivatization of controlled-pore glass beads for solid-phase oligonucleotide synthesis." Nucleic Acids Research (1990); 18.13 : 3813-3821.

Database EMBL [Online], "Dna fragment having promoter function." XP002767746, retrieved from EBI accession No. EM PAT:DD324094, Sep. 20, 2006.

Database Geneseq [Online] "Corynebacterium glutamicum DNA gyrase subunit B DNA, SEQ ID: 123." XP002767747, retrieved from EBI accession No. GSN: AEM36105. Mar. 8, 2007.

Database Geneseq [Online] "Corynebacterium glutamicum DNA gyrase subunit B DNA, SEQ ID: 123." XP002770467, retrieved from EBI accession No. GSN:AEM36105, Mar. 8, 2007.

Dauner, M., et al., "Intracellular carbon fluxes in riboflavin-producing Bacillus subtilis during growth on two-carbon substrate mixtures." Appl. Environ. Microbiol. (2002); 68(4): 1760-1771.

Drmanac, Radoje, et al. "Human genome sequencing using unchained base reads on self-assembling DNA nanoarrays." Science (2010); 327.5961: 78-81.

Duarte, N.C., et al., "Reconstruction and validation of *Saccharomyces scerevisiae* iND750, a fully compartmentalized genome-scale metabolic model." Genome Res. (2004); 14: 1298-1309.

Dunican, L.K. and Shivnan, E. "High frequency transformation of whole cells of amino acid producing coryneform bacteria using high voltage electroporation." Nature Biotechnology (1989); 7.10: 1067-1070.

Durand, Roger, et al. "Transient expression of the β-glucuronidase gene after biolistic transformation of the anaerobic fungus Neocallimastix frontalis." Current Genetics (1997); 31.2: 158-161.

Edwards, J.S. and Palsson, B.O., "Systems properties of the Haemophilus influenzae Rd metabolic genotype." J. Biol. Chem. (1999); 274(25): 17410-17416.

Edwards, J.S. and Palsson, B.O., "The *Escherichia coli* MG1655 in silico metabolic genotype: its definition, characteristics, and capabilities." Proc. Natl. Acad. Sci. U. S. A. (2000); 97(10): 5528-5533.

Eid, John, et al. "Real-time DNA sequencing from single polymerase molecules." Science (2009); 323.5910: 133-138.

Eikmanns, Bernhard J. "Identification, sequence analysis, and expression of a Corynebacterium glutamicum gene cluster encoding the three glycolytic enzymes glyceraldehyde-3-phosphate dehydrogenase,

(56) References Cited

OTHER PUBLICATIONS 3-phosphoglycerate kinase, and triosephosphate isomerase." Journal of Bacteriology (1992); 174.19: 6076-6086.
Eikmanns, Bernhard J., et al. "A family of Corynebacterium glutamicum/ *Escherichia coli* shuttle vectors for cloning, controlled gene expression, and promoter probing." Gene (1991); 102.1: 93-98.
Engler, Carola, et al. "A one pot, one step, precision cloning method with high throughput capability." PLOS ONE (2008); 3.11: e3647.
Fischer, S., et al., "The art of CHO cell engineering: A comprehensive retrospect and future perspectives." Biotechnology Advances (2015); 33: 1878-1896.
Fitzpatrick, R., et al. "Construction and characterization of recA mutant strains of Corynebacterium glutamicum and Brevibacterium lactofermentum." Applied Microbiology and Biotechnology (1994); 42.4: 575-580.
Förster, J., et al., "Genome-scale reconstruction of the *Saccharomyces cerevisiae* metabolic network." Genome Res. (2003); 13: 244-253.
Fox, Richard J., et al. "Improving catalytic function by ProSAR-driven enzyme evolution." Nature Biotechnology (2007); 25.3: 338-344.
Frewen, B., et al., "A Detailed, flexible model for sharing DNA concepts." IWBDA 2015, 7th International Workshop on Bio-Design Automation, University of Washington, pp. 66-67, Aug. 19-21, 2015 (Presentation and Poster), 86 pages.
Frey and Kallio, " Bacterial hemoglobins and flavohemoglobins: versatile proteins and their impact on microbiology and biotechnology." FEMS Microbiol Rev. (Oct. 2003); 27(4): 525-545.
Gardner et al., "Production of Citric Acid by Mutants of Aspergillus niger." J. Gen. Microbial (1956); 14: 228-237.
Gietz, et al., "Improved method for high efficiency transformation of intact yeast cells." Nucleic Acids Res. (Mar. 1992); 20(6): 1425.
GenBank Accession No. CP010451.1 (Jan. 20, 2015), Corynebacterium glutamicum strain B253 DNA, complete genome, downloaded Jan. 12, 2018, 10 pages, https://www.ncbi.nlm.nih.gov/nuccore/748809780?sat=21&satkey=31610401.
GenBank CP001663.1, "*Mycobacterium smegmatis* str. MC2 155, complete genome." Jan. 31, 2014 (Jan. 31, 2014) [retrieved on Oct. 30, 2017, https://www.ncbi.nlm.nih.gov/nuccore/CP001663.1] genomic sequence nucleotide 4269453-4267996, 2 pages.
Gibson, Daniel G., et al. "Enzymatic assembly of DNA molecules up to several hundred kilobases." Nature Methods (2009); 6.5: 343-345.
Goosen, Theo, et al. "Transformation of Aspergillus niger using the homologous orotidine-5'-phosphate-decarboxylase gene." Current Genetics (1987); 11.6: 499-503.
GPU-Based Deep Learning Inference: A Performance and Power Analysis, NVidia Whitepaper, Nov. 2015, 12 pages.
Greger, Ingo H., et al. "Balancing transcriptional interference and initiation on the GAL7 promoter of *Saccharomyces cerevisiae*." Proceedings of the National Academy of Sciences (2000); 97.15: 8415-8420.
Guerrero, Carmen, et al. "Directed mutagenesis of a regulatory palindromic sequence upstream from the Brevibacterium lactofermentum tryptophan operon." Gene (1994); 138.1: 35-41.
Han, M.J. et al., "Engineering Escherichia coli for increased production of serine-rich proteins based on proteome profiling." Appl. Environ. Microbiol. (2003); 69(10): 5772-5781.
Han, M.J. et al., "Proteome analysis of metabolically engineered *Escherichia coli* cells producing poly(3-hydroxybutyrate)." J. Bacteriol. (2001); 183(1): 301-308.
Haynes, Jill A., and Britz, Margaret L. "The effect of growth conditions of Corynebacterium glutamicum on the transformation frequency obtained by electroporation." Microbiology (1990); 136.2: 255-263.
Hermann, Thomas, et al. "Proteome analysis of Corynebacterium glutamicum." Electrophoresis (2001); 22.9: 1712-1723.
Hillson, N.J., "j5 DNA Assembly Design Automation Software." ACS Synthetic Biology (2011); 1: 14-21.

Hirao, et al., "L-Lysine production in continuous culture of an L-lysine hyperproducing mutant of Corynebacterium glutamicum." Applied Microbiology and Biotechnology (1989); 32 (3): 269-273.
Hong, Jiong, et al. "Cloning and functional expression of thermostable β-glucosidase gene from Thermoascus aurantiacus." Applied Microbiology and Biotechnology (2007); 73.6: 1331-1339.
Hong, S.H., et al., "The genome sequence of the capnophilic rumen bacterium Mannheimia succiniciproducens." Nat. Biotechnol. (2004); 22: 1275-1281.
Hui, A., et al. "Mutagenesis of the three bases preceding the start codon of the beta-galactosidase mRNA and its effect on translation in *Escherichia coli*." The EMBO Journal (1984); 3.3: 623-629.
Ikeda et al., "A genome-based approach to create a minimally mutated Corynebacterium glutamicum strain for efficient L-lysine production." J. Ind. Microbial. Biotechnol. (2006); 33(7): 610-615.
International Application No. PCT/US2016/065464, International Preliminary Report on Patentability, dated Jun. 12, 2018, 7 pages.
International Application No. PCT/US2016/065464, International Search Report and Written Opinion, dated Jun. 26, 2017, 14 pages.
International Application No. PCT/US2017/039772, International Preliminary Report on Patentability, dated Jan. 1, 2019, 12 pages.
International Application No. PCT/US2017/039772, International Search Report and Written Opinion, dated Jan. 8, 2018, 18 pages.
International Application No. PCT/US2017/039772, Invitation to Pay Additional Fees, dated Oct. 23, 2017, 3 pages.
Isojärvi, J., et al., "Draft Genome Sequence of Calothrix Strain 336/3, a Novel H2-Producing Cyanobacterium Isolated from a Finnish Lake." Genome Announcements (2015); 3 (1): 1-2, e01474-14.
Ito, Hisao, et al. "Transformation of intact yeast cells treated with alkali cations." Journal of Bacteriology (1983); 153.1: 163-168.
J5 DeviceEditor manual excerpt from https://j5.jbei.org/index.php/Main_Page_downloadedcontent available Apr. 19, 2016, 45 pages.
Jäger, W., et al. "Expression of the Bacillus subtilis sacB gene leads to sucrose sensitivity in the gram-positive bacterium Corynebacterium glutamicum but not in Streptomyces lividans." Journal of Bacteriology (1992); 174.16: 5462-5465.
Jensen, Peter Ruhdal and Hammer, Karin. "Artificial promoters for metabolic optimization." Biotechnology and Bioengineering (1998); 58.2-3: 191-195.
Jones, Jonathan DG, et al. "High level expression of introduced chimaeric genes in regenerated transformed plants." The EMBO Journal (1985); 4.10: 2411.
Jungwirth, Britta, et al. "Triple transcriptional control of the resuscitation promoting factor 2 (rpf2) gene of Corynebacterium glutamicum by the regulators of acetate metabolism RamA and RamB and the cAMP-dependent regulator GlxR." FEMS Microbiology Letters (2008); 281.2: 190-197.
Kabir, M.M. and Shimizu, K., "Fermentation characteristics and protein expression patterns in a recombinant *Escherichia coli* mutant lacking phosphoglucose isomerase for poly(3-hydroxybutyrate) production." Appl. Microbiol. Biotechnol. (2003); 62: 244-255.
Kadonaga, James T. "Regulation of RNA polymerase II transcription by sequence-specific DNA binding factors." Cell (2004); 116.2: 247-257.
Kashyap, Hirak, et al. "Big data analytics in bioinformatics: A machine learning perspective." Journal of Latex Class Files (2014);13(9): 20 pages.
Khanna, N.C., et al. "Identification of the template binding polypeptide in the pea chloroplast transcriptional complex." Nucleic Acids Research (1992); 20.1: 69-74.
Khosla and Bailey, "Heterologous expression of a bacterial haemoglobin improves the growth properties of recombinant *Escherichia coli*." Nature (Feb. 1988); 331(6157): 633-635.
Khosla, et al., "Expression of Intracellular Hemoglobin Improves Protein Synthesis in Oxygen-Limited *Escherichia coli*." Biotechnology (N.Y). (Sep. 1990); 8(9): 849-853.
Khudyakov, Yu E., et al. "Effect of structure of the initiator codon on translation in *E. coli*." FEBS Letters (1998); 232.2: 369-371.
Kikuchi, Yoshimi, et al. "Functional analysis of the twin-arginine translocation pathway in Corynebacterium glutamicum ATCC 13869." Applied and environmental microbiology (2006); 72.11: 7183-7192.

(56) References Cited

OTHER PUBLICATIONS

Kim, Jae Bum, et al. "Polony multiplex analysis of gene expression (PMAGE) in mouse hypertrophic cardiomyopathy." Science (2007); 316.5830: 1481-1484.
Kimball, A., "The Data-Driven Future of Biotechnology." Zymergen, Machine learning, automation, and biotech, Strata + Hadoop World, Make Data Work conference, Presentation, London, UK, May 5, 2015, 49 pages http://cdn.oreillystatic.com/en/assets/1/event/132/the%20data-driven%20future%20of%20biotechnology%20Presentation.pdf.
Kirchner, Oliver and Tauch, Andreas. "Tools for genetic engineering in the amino acid-producing bacterium Corynebacteriumglutamicum." Journal of Biotechnology (2003); 104.1: 287-299.
Kotera, Ippei, et al. "A high-throughput and single-tube recombination of crude PCR products using a DNA polymerase inhibitor and type IIS restriction enzyme." Journal of Biotechnology (2008); 137.1: 1-7.
Kozlov, Igor A., et al. "Significant improvement of quality for long oligonucleotides by using controlled pore glass with large pores." Nucleosides, Nucleotides and Nucleic Acids (2005); 24.5-7: 1037-1041.
Krämer, O., et al., "Methods in mammalian cell line engineering: from random mutagenesis to sequence-specific approaches." Appl Microbiol Biotechnol (2010); 88: 425-436.
Krömer, J.O., et al., "In-depth profiling of lysine-producing Corynebacterium glutamicum by combined analysis of the transcriptome, metabolome, and fluxome." J. Bacteriol. (2004); 186(6): 1769-1784.
Kuo, Chih-Chung, et al., "The emerging role of systems biology for engineering protein production in CHO cells." Current Opinion in Biotechnology (2018); 51: 64-69.
Labarre, Jean, et al. "Gene replacement, integration, and amplification at the gdhA locus of Corynebacterium glutamicum." Journal of Bacteriology (1993); 175.4: 1001-1007.
Lee, et al., "A Highly Characterized Yeast Toolkit for Modular, Multipart Assembly." ACS Synthetic Biology (2015); 4(9): 975-986 (Published Apr. 14, 2015).
Lee, J.H., et al., "Global analyses of transcriptomes and proteomes of a parent strain and an L-threonine-overproducing mutant strain." J. Bacteriol. (2003); 185(18): 5442-5451.
Lee, Joo-Young, et al. "Adaptive evolution of Corynebacterium glutamicum resistant to oxidative stress and its global gene expression profiling." Biotechnology Letters (2013); 35.5: 709-717.
Lee, Sang Yup, et al., "Systems biotechnology for strain improvement." Trends in Biotechnology (2005); 23(7): 349-358.
Leng, Xiaoyan, et al. "Classification using functional data analysis for temporal gene expression data." Bioinformatics (2006); 22.1: 68-76.
Li, et al., "C-Brick: A New Standard for Assembly of Biological Parts Using Cpf1." ACS Synth. Biol. (2016); 5 (12): 1383-1388.
Libbrecht, Maxwell W., et al. "Machine learning applications in genetics and genomics." Nature Reviews Genetics (2015); 16.6: 321-332.
Lindroth, Peter, and Mopper, Kenneth. "High performance liquid chromatographic determination of subpicomole amounts of amino acids by precolumn fluorescence derivatization withoff-phthaldialdehyde." Anal. Chem (1979); 51.11: 1667-1674.
Liu, et al., "Developing a high-throughput screening method for threonine overproduction based on an artificial promoter." Microbial Cell Factories (2015); 14: 121, 11 pages.
Makrides, Savvas C. "Strategies for achieving high-level expression of genes in *Escherichia coli*." Microbiological Reviews (1996); 60.3: 512-538.
Malumbres, Marcos, et al. "Codon preference in corynebacteria." Gene (1993); 134.1: 15-24.
Margulies, Marcel, et al. "Genome sequencing in microfabricated high-density picolitre reactors." Nature (2005); 437.7057: 376-380.
Martin, J. F., et al. "Cloning Systems in Amino Acid-Producing Corynebacteria." Nature Biotechnology (1987); 5.2: 137-146.

Menkel et al., "Influence of increased aspartate availability on lysine formation by a recombinant strain of Corynebacterium glutamicum and utilization of fumarate." Appl. Environ. Microbiol. (1989); 55(3): 684-688.
Mockel, Bettina, et al. "Functional and structural analyses of threonine dehydratase from Corynebacterium glutamicum." Journal of Bacteriology (1992);174.24: 8065-8072.
Mockel, Bettina, et al. "Threonine dehydratases of Corynebacterium glutamicum with altered allosteric control: their generation and biochemical and structural analysis." Molecular Microbiology (1994); 13.5: 833-842.
Molenaar, et al., "Biochemical and genetic characterization of the membrane-associated malate dehydrogenase (acceptor) from Corynebacterium glutamicum." Eur J Biochem. (1998); 254(2): 395-403.
Moore, Jeffrey C., et al. "Strategies for the in vitro evolution of protein function: enzyme evolution by random recombination of improved sequences." Journal of Molecular Biology (1997); 272.3: 336-347.
Murray, Elizabeth E. et al. "Codon usage in plant genes." Nucleic Acids Research (1989); 17.2: 477-498.
Nakashima, Nobutaka, et al. "Bacterial cellular engineering by genome editing and gene silencing." International Journal of Molecular Sciences (2014); 15.2: 2773-2793.
Neumann, Susanne, and Quiñones, Ariel. "Discoordinate gene expression of gyrA and gyrB in response to DNA gyrase inhibition in *Escherichia coli*." Journal of Basic Microbiology (1997); 37.1: 53-69.
Ohnishi et al., "A novel methodology employing Corynebacterium glutamicum genome information to generate a new L-lysine-producing mutant." Appl. Microbial Biotechnol (2002); 58(2): 217-223. Published online: Dec. 8, 2001.
Ohnishi, J. et al., "Efficient 40 degrees C fermentation of L-lysine by a new Corynebacterium glutamicum mutant developed by genome breeding." Appl. Microbiol. Biotechnol. (2003); 62: 69-75.
Paek, Se-Hwan, et al. "Development of rapid one-step immunochromatographic assay." Methods (2000); 22.1: 53-60.
Parry, Neil J., et al. "Biochemical characterization and mechanism of action of a thermostable β-glucosidase purified from Thermoascus aurantiacus." Biochemical Journal (2001); 353.1: 117-127.
Pátek, Miroslav, et al. "Promoters from Corynebacterium glutamicum: cloning, molecular analysis and search for a consensus motif." Microbiology (1996); 142.5: 1297-1309.
Pedersen and Phillips, "Towards programming languages for genetic engineering of living cells." J.R. Soc. Interface (2009); 6 (Suppl 4): S437-S450. Published online Apr. 15, 2009.
Peters-Wendisch, Petra G., et al. "Pyruvate carboxylase from Corynebacterium glutamicum: characterization, expression and inactivation of the pyc gene." Microbiology (1998); 144.4: 915-927.
Pfeifer-Sancar, Katharina, et al. "Comprehensive analysis of the Corynebacterium glutamicum transcriptome using an improved RNAseq technique." BMC Genomics (2013):14.1: 888, 23 pages.
Price, N.D., et al., "Genome-scale models of microbial cells: evaluating the consequences of constraints." Nat. Rev. Microbiol. (2004); 2: 886-897.
Prompramote, Supawan, et al. "Machine learning in bioinformatics." Bioinformatics Technologies. Springer Berlin Heidelberg (2005); pp. 117-153.
Qiu, Zhihao, et al. "The Escherichia coli polB Locus Is Identical to dinA, the Structural Gene for DNA Polymerase II Characterization of Pol II Purified From a polB Mutant." Journal of Biological Chemistry (1997); 272.13: 8611-8617.
Rastegari, Hilda et al., "Improvement in the Production of L-Lysine by Over-expression of Aspartokinase (ASK) in C. glutamicum ATCC-21799", Tropical Journal of Pharmaceutical Research, Feb. 2013, pp. 51-56, vol. 12, No. 1.
Reddy, Prasad, et al. "Translational efficiency of the *Escherichia coli* adenylate cyclase gene: mutating the UUG initiation codon to GUG or AUG results in increased gene expression." Proceedings of the National Academy of Sciences (1985); 82.17: 5656-5660.
Reed, J.L., et al., "An expanded genome-scale model of *Escherichia coli* K-12 (iJR904 GSM/GPR)." Genome Biol. (2003); 4, R54.

(56) References Cited

OTHER PUBLICATIONS

Reimer, et al., "High-Throughput Screening of a Corynebacterium glutamicum Mutant Library on Genomic and Metabolic Level." PLOS ONE (2014); 9(2): e86799, 12 pages.
Reinscheid, Dieter J., et al. "Stable expression of hom-1-thrB in Corynebacterium glutamicum and its effect on the carbon flux to threonine and related amino acids." Applied and Environmental Microbiology (1994); 60.1: 126-132.
Rey, Daniel Alexander, et al. "The putative transcriptional repressor McbR, member of the TetR-family, is involved in the regulation of the metabolic network directing the synthesis of sulfur containing amino acids in Corynebacterium glutamicum." Journal of Biotechnology (2003); 103.1: 51-65.
Reyrat, Jean-Marc, et al. "Counterselectable markers: untapped tools for bacterial genetics and pathogenesis." Infection and Immunity (1998); 66.9: 4011-4017.
Ricciardelli, Carmela, et al. "Development and characterization of primary cultures of smooth muscle cells from the fibromuscular stroma of the guinea pig prostate." In Vitro Cellular & Developmental Biology (1989); 25.11: 1016-1024.
Rückert, C., et al., "Genome-wide analysis of the L-methionine biosynthetic pathway in Corynebacterium glutamicum by targeted gene deletion and homologous complementation." J. Biotechnol. (2003); 104: 213-228.
Rytter, et al., "Synthetic promoter libraries for Corynebacterium glutamicum." Applied Microbiology and Biotechnology (2014); 98 (6): 2617-2623.
Sahm, Hermann, et al. "d-Pantothenate Synthesis in Corynebacterium glutamicum and Use of panBC and Genes Encoding I-Valine Synthesis ford-Pantothenate Overproduction." Applied and Environmental Microbiology (1999); 65.5: 1973-1979.
Sasaki, et al. "Simultaneous utilization of D-cellobiose, D-glucose, and D-xylose by recombinant Corynebacterium glutamicum under oxygen-deprived conditions." Applied Microbiology and Biotechnology (2008); 81.4: 691-699.
Schäfer, A., et al. "Increased fertility of Corynebacterium glutamicum recipients in intergeneric matings with Escherichia coli after stress exposure." Applied and Environmental Microbiology (1994); 60.2: 756-759.
Schäfer, Andreas, et al. "Small mobilizable multi-purpose cloning vectors derived from the Escherichia coli plasmids pK18 and pK19: selection of defined deletions in the chromosome of Corynebacterium glutamicum." Gene (1994); 145.1: 69-73.
Schilling, C.H., et al., "Genome-scale metabolic model of Helicobacter pylori 26695." J. Bacteriol. (2002); 184(16): 4582-4593.
Schrumpf, Barbel, et al. "A functionally split pathway for lysine synthesis in Corynebacterium glutamicium." Journal of Bacteriology (1991); 173.14: 4510-4516.
Schwarzer, Astrid, and Pühler, Alfred. "Manipuiation of Corynebacterium glutamicum by Gene Disruption and Replacement." Nature Biotechnology (1991); 9.1: 84-87.
Serwold-Davis, Theresa M., et al. "Localization of an origin of replication in Corynebacterium diphtheriae broad host range plasmid pNG2 that also functions inEscherichia coli." FEMS Microbiology Letters (1990) 66.1-3: 119-123.
Shevade, Shirish Krishnaj, et al. "A simple and efficient algorithm for gene selection using sparse logistic regression." Bioinformatics (2003); 19.17: 2246-2253.
Shuman, Stewart. "Novel approach to molecular cloning and polynucleotide synthesis using vaccinia DNA topoisomerase." Journal of Biological Chemistry (1994); 269.51: 32678-32684.
Sierzchala, Agnieszka B., et al. "Solid-phase oligodeoxynucleotide synthesis: a two-step cycle using peroxy anion deprotection." Journal of the American Chemical Society (2003); 125.44: 13427-13441.
Simon, R., et al. "A broad host range mobilization system for in vivo genetic engineering: transposon mutagenesis in gram negative bacteria." Nature Biotechnology (1983); 1.9: 784-791.
Snitkin and Segre, "Epistatic Interaction Maps Relative to Multiple Metabolic Phenotypes." PLoS Genet (2011); 7(2): e1001294.

Sonnen, Hans, et al. "Characterization of pGA1, a new plasmid from Corynebacterium glutamicum LP-6." Gene (1991); 107.1: 69-74.
Spackman, Darrel H., et al. "Automatic recording apparatus for use in the chromatography of amino acids." Analytical Chemistry (1958); 30: 1190-1206.
Spratt, Brian G., et al. "Kanamycin-resistant vectors that are analogues of plasmids pUC8, pUC9, pEMBL8 and pEMBL9." Gene (1986); 41.2: 337-342.
Stansen, Corinna, et al. "Characterization of a Corynebacterium glutamicum lactate utilization operon induced during temperature-triggered glutamate production." Applied and environmental microbiology (2005); 71.10: 5920-5928.
Stemmer, Willem P. "DNA shuffling by random fragmentation and reassembly: In vitro recombination for molecular evolution." Proceedings of the National Academy of Sciences (1994); 91.22: 10747-10751.
Stemmer, Willem P.C. "Rapid evolution of a protein in vitro by DNA shuffling." Nature (1994); 370.6488: 389-391.
Stemmer, Willem P.C. "The evolution of molecular computation." Science (1995); 270.5241: 1510-1511.
Stemmer, Willem P.C., "Searching Sequence Space" Nature Biotechnology (1995); 13: 549-553.
Stemmer, Willem P.C., et al. "Single-step assembly of a gene and entire plasmid from large numbers of oligodeoxyribonucleotides." Gene (1995); 164.1: 49-53.
Stenström, C. Magnus, et al. "Cooperative effects by the initiation codon and its flanking regions on translation initiation." Gene (2001); 273.2: 259-265.
Stephanopoulos, G., "Exploiting biological complexity for strain improvement through systems biology." Nat. Biotechnol. (2004); 22: 1261-1267.
Student. "The probable error of a mean." Biometrika (1908); 6(1): 1-25.
Su, Shin-San, et al. "*Escherichia coli* mutS-encoded protein binds to mismatched DNA base pairs." Proceedings of the National Academy of Sciences (1986); 83.14: 5057-5061.
Suda, Masako, et al. "Transcriptional regulation of Corynebacterium glutamicum methionine biosynthesis genes in response to methionine supplementation under oxygen deprivation." Applied Microbiology and Biotechnology (2008); 81.3: 505-513.
Sugimoto, Masakazu, et al. "Sequence analysis of functional regions of homoserine dehydrogenase genes from L-lysine and L-threonine-producing mutants of Brevibacterium lactofermentum." Bioscience, Biotechnology, and Biochemistry (1997); 61.10: 1760-1762.
Tauch, Andreas, et al. "Corynebacterium glutamicum DNA is subjected to methylation-restriction in *Escherichia coli*." FEMS Microbiology Letters (1994); 123.3: 343-347.
Tauch, Andreas, et al. "Plasmids in Corynebacterium glutamicum and their molecular classification by comparative genomics." Journal of Biotechnology (2003); 104.1: 27-40.
Tear, Crystal Jing Ying, et al. "Excision of Unstable Artificial Gene-Specific Inverted Repeats Mediates Scar-Free Gene Deletions in *Escherichia coli*." Applied Biochemistry and Biotechnology (2014); 175.4: 1858-1867.
Thierbach, Georg, et al. "Transformation of spheroplasts and protoplasts of Corynebacterium glutamicum." Applied Microbiology and Biotechnology (1998); 29.4: 356-362.
Third Party Observation filed in connection with International Application No. PCT/US2016/065465, dated Apr. 6, 2018, 12 pages.
Third-Party Submission filed with the U.S. Patent and Trademark Office on Dec. 7, 2017, in connection with U.S. Appl. No. 15/396,230, 14 pages.
Third-Party Submission filed with the U.S. Patent and Trademark Office on May 1, 2018, in connection with U.S. Appl. No. 15/140,296, 63 pages.
Tian, Jingdong, et al. "Advancing high-throughput gene synthesis technology." Molecular BioSystems (2009); 5.7: 714-722.
Trikka et al., "Iterative carotenogenic screens identify combinations of yeast gene deletions that enhance sclareol production." Microbial Cell Factories (2015); 14:60 (Published on line Apr. 24, 2015), 1:19, 19 pages.

(56) References Cited

OTHER PUBLICATIONS

Tsuchiya, Makoto, and Morinaga, Yasushi. "Genetic control systems of *Escherichia coli* can confer inducible expression of cloned genes in coryneform bacteria." Nature Biotechnology (1998); 6.4: 428-430.

Tummala, S.B. et al., "Transcriptional analysis of product concentration driven changes in cellular programs of recombinant Clostridium acetobutylicum strains." Biotechnol. Bioeng. (2003); 84, 842-854.

Vašicová, Pavla, et al. "Analysis of the Corynebacterium glutamicum dapA promoter." Journal of Bacteriology (1999);181.19: 6188-6191.

Voskuil, Martin I., et al. "The -16 region of Bacillus subtilis and other gram-positive bacterial promoters." Nucleic Acids Research (1998); 26.15: 3584-3590.

Wagner, Robert, et al. "Mutation detection using immobilized mismatch binding protein (MutS)." Nucleic Acids Research (1995); 23.19: 3944-3948.

Wang et al., "Programming cells by multiplex genome engineering and accelerated evolution." Nature (2009); 460: 894-898.

Wang, Junping, et al. "An improved recombineering approach by adding RecA to λ red recombination." Molecular Biotechnology (2006); 32.1: 43-53.

Weber, Ernst, et al. "Assembly of designer TAL effectors by Golden Gate cloning." PLOS ONE (2011); 6.5: e19722.

West, Steven and Proudfoot, Nicholas J. "Transcriptional termination enhances protein expression in human cells." Molecular Cell (2009); 33.3: 354-364.

West, Steven, et al. "Molecular dissection of mammalian RNA polymerase II transcriptional termination." Molecular Cell (2008); 29.5: 600-610.

Wilson, Erin H., et al., "Genotype specification language." ACS Synthetic Biology (2016); 5 (6): 471-478.

WIPO Communication dated Apr. 10, 2018 to Applicant, Zymergen Inc. In connection with International Application No. PCT/US2016/065465, advising of third party observation filed Apr. 6, 2018, 1 page.

Wittmann, C. and Heinzle, E., "Modeling and experimental design for metabolic flux analysis of lysine-producing Corynebacteria by mass spectrometry." Metab. Eng. (2001); 3: 173-191.

Yelton, M. Melanie, et al. "Transformation of Aspergillus nidulans by using a trpC plasmid." Proceedings of the National Academy of Sciences (1984); 81 (5): 1470-1474.

Yoon, S.H., et al., "Combined transcriptome and proteome analysis of *Escherichia coli* during high Cell density culture." Biotechnol. Bioeng. (2003); 81: 753-767.

Zetsche, et al., "Cpf1 Is a Single RNA-Guided Endonuclease of a Class 2 CRISPR-Cas System." Cell (2015); 163 (2): 759-771.

Zhang, Ji-Hu, et al. "Directed evolution of a fucosidase from a galactosidase by DNA shuffling and screening." Proceedings of the National Academy of Sciences (1997); 94 (9): 4504-4509.

Database UniProt [Online] Jan. 25, 2012 (Jan. 25, 2012), "SubName: Full=Nitric oxide dioxygenase {EC0:00003131 EMBL:EHC19637.1 }; EC=1.14.12.17 {EC0:00003131 EMBL:EHC19637.1 };" XP002791262, retrieved from EBI accession No. UNIPROT:G6FNK7 Database accession No. G6FNK7, 2 pages.

European Application No. 17821157.9, Partial Supplementary European Search Report dated May 29, 2019, 15 pages.

SEQUENCE LISTING

```
<160> NUMBER OF SEQ ID NOS: 34

<210> SEQ ID NO 1
<211> LENGTH: 97
<212> TYPE: DNA
<213> ORGANISM: Corynebacterium glutamicum
<220> FEATURE:
<221> NAME/KEY: misc_feature
<222> LOCATION: (1)..(97)
<223> OTHER INFORMATION: Pcg0007_39

<400> SEQUENCE: 1
tgccgtttct cgcgttgtgt gtggtactac gtggggacct aagcgtgtat tatggaaacg      60
tctgtatcgg ataagtagcg aggagtgttc gttaaaa                              97

<210> SEQ ID NO 2
<211> LENGTH: 97
<212> TYPE: DNA
<213> ORGANISM: Corynebacterium glutamicum
<220> FEATURE:
<221> NAME/KEY: misc_feature
<222> LOCATION: (1)..(97)
<223> OTHER INFORMATION: Pcg0007

<400> SEQUENCE: 2
tgccgtttct cgcgttgtgt gtggtactac gtggggacct aagcgtgtaa gatggaaacg      60
tctgtatcgg ataagtagcg aggagtgttc gttaaaa                              97

<210> SEQ ID NO 3
<211> LENGTH: 93
<212> TYPE: DNA
<213> ORGANISM: Corynebacterium glutamicum
<220> FEATURE:
<221> NAME/KEY: misc_feature
<222> LOCATION: (1)..(93)
<223> OTHER INFORMATION: Pcg1860

<400> SEQUENCE: 3
cttagctttg acctgcacaa atagttgcaa attgtcccac atacacataa agtagcttgc      60
gtatttaaaa ttatgaacct aagggggttta gca                                 93

<210> SEQ ID NO 4
<211> LENGTH: 98
<212> TYPE: DNA
<213> ORGANISM: Corynebacterium glutamicum
<220> FEATURE:
<221> NAME/KEY: misc_feature
<222> LOCATION: (1)..(98)
```

<223> OTHER INFORMATION: Pcg0755

<400> SEQUENCE: 4
aataaattta taccacacag tctattgcaa tagaccaagc tgttcagtag ggtgcatggg    60
agaagaattt cctaataaaa actcttaagg acctccaa                            98

<210> SEQ ID NO 5
<211> LENGTH: 97
<212> TYPE: DNA
<213> ORGANISM: Corynebacterium glutamicum
<220> FEATURE:
<221> NAME/KEY: misc_feature
<222> LOCATION: (1)..(97)
<223> OTHER INFORMATION: Pcg0007_265

<400> SEQUENCE: 5
tgccgtttct cgcgttgtgt gtggtactac gtggggacct aagcgtgtac gctggaaacg    60
tctgtatcgg ataagtagcg aggagtgttc gttaaaa                             97

<210> SEQ ID NO 6
<211> LENGTH: 86
<212> TYPE: DNA
<213> ORGANISM: Corynebacterium glutamicum
<220> FEATURE:
<221> NAME/KEY: misc_feature
<222> LOCATION: (1)..(86)
<223> OTHER INFORMATION: Pcg3381

<400> SEQUENCE: 6
cgccggataa atgaattgat tatttaggc tcccagggat taagtctagg gtggaatgca     60
gaaatatttc ctacggaagg tccgtt                                         86

<210> SEQ ID NO 7
<211> LENGTH: 97
<212> TYPE: DNA
<213> ORGANISM: Corynebacterium glutamicum
<220> FEATURE:
<221> NAME/KEY: misc_feature
<222> LOCATION: (1)..(97)
<223> OTHER INFORMATION: Pcg0007_119

<400> SEQUENCE: 7
tgccgtttct cgcgttgtgt gtggtactac gtggggacct aagcgtgttg catggaaacg    60
tctgtatcgg ataagtagcg aggagtgttc gttaaaa                             97

<210> SEQ ID NO 8
<211> LENGTH: 87
<212> TYPE: DNA
<213> ORGANISM: Corynebacterium glutamicum
<220> FEATURE:
<221> NAME/KEY: misc_feature
<222> LOCATION: (1)..(87)
<223> OTHER INFORMATION: Pcg3121

<400> SEQUENCE: 8
gtggctaaaa cttttggaaa cttaagttac ctttaatcgg aaacttattg aattcgggtg    60
aggcaactgc aactctggac ttaaagc                                        87

<210> SEQ ID NO 9
<211> LENGTH: 441
<212> TYPE: DNA
<213> ORGANISM: Vitreoscilla stercoraria
<220> FEATURE:
<221> NAME/KEY: misc_feature
<222> LOCATION: (1)..(441)
<223> OTHER INFORMATION: Vhb01

<400> SEQUENCE: 9

| | | | | | |
|---|---|---|---|---|---|
| atgctagatc | aacagacaat | taacattatc | aaagctacgg | taccggttct | taaagaacat | 60 |
| ggtgtgacta | ttactactac | tttctataag | aatttgtttg | cgaagcatcc | agaagtccgc | 120 |
| ccactttttg | atatgggtcg | tcaggaatct | ctggagcagc | ctaaagctct | tgcgatgacg | 180 |
| gttcttgcgg | cagcgcagaa | tattgagaat | ctgccagcga | ttcttcctgc | ggtgaagaaa | 240 |
| attgcggtca | acattgtca | ggctggagta | gcagcagcac | attatccgat | cgtaggacaa | 300 |
| gaacttttgg | gggctatcaa | agaagtgctc | ggcgacgctg | ctaccgatga | tattcttgac | 360 |
| gcgtggggaa | aagcttacgg | tgttatcgct | gatgtattca | ttcaagttga | ggctgatttg | 420 |
| tatgcgcaag | ctgttgaata | g | | | | 441 |

<210> SEQ ID NO 10
<211> LENGTH: 411
<212> TYPE: DNA
<213> ORGANISM: Gordonia terrae C-6
<220> FEATURE:
<221> NAME/KEY: misc_feature
<222> LOCATION: (1)..(411)
<223> OTHER INFORMATION: Vhb02

<400> SEQUENCE: 10

| | | | | | |
|---|---|---|---|---|---|
| atgcttaatc | gtgaagttct | ccaagattct | ctatcccttg | ttatcgacga | tgaacagaaa | 60 |
| cttatgctta | gtttctatga | tcgcctgttc | gaggaacatc | cagaagtccg | cccgatgttt | 120 |
| ggtgcggact | tgcgtcctca | ggctacgatg | cttcaacagg | ctattgcggc | tgttctagat | 180 |
| catttggatg | atacggaatg | gcttggacga | actttgggag | cgcttggtcg | gcgccatgca | 240 |
| gacctgggag | tgactccaga | gatgtacggt | tgggtagctg | gcgcgcttat | tactacgatg | 300 |
| gctgagcgtg | gtggcgggga | ttggactgat | gaaatgacag | cggcttggac | cgaagctctt | 360 |
| ggtgcagtgg | cgggacttat | gttggacgct | tatccggcag | tagcggatta | g | 411 |

<210> SEQ ID NO 11
<211> LENGTH: 423
<212> TYPE: DNA
<213> ORGANISM: Sandaracinus amylolyticus
<220> FEATURE:
<221> NAME/KEY: misc_feature
<222> LOCATION: (1)..(423)
<223> OTHER INFORMATION: Vhb03

<400> SEQUENCE: 11

| | | | | | |
|---|---|---|---|---|---|
| atgtcccttg | atgttccttt | gcttagatct | tcattcgaat | tggtacttga | acgtgagcct | 60 |
| gcacttaccg | cgcgttttta | cgaaatccta | ttcgagcgct | atccgcaagc | tcgcccgctt | 120 |
| tttgctcgga | atgctcgtaa | acagcaagaa | gaaatgctgg | cgcgagcgct | ggctgctgta | 180 |
| gtggaccgcc | ttgaagatgc | accatggctt | gtggagactt | tggagcgat | gggagcgaaa | 240 |
| catgtcgatt | atggcgtcac | tgaagaaatg | tatggttggg | ttggggacgc | acttcttcgt | 300 |
| acgctagctg | aagttgctgg | tgatgcttgg | acgccagagt | tggaagcggc | ttgggcggca | 360 |
| gcttacggtg | cgattcgcga | tcttatgctc | gctggagcga | gtcgtgcgca | ggcagctgaa | 420 |
| tag | | | | | | 423 |

<210> SEQ ID NO 12
<211> LENGTH: 498
<212> TYPE: DNA

<213> ORGANISM: Fischerella sp. JSC-11
<220> FEATURE:
<221> NAME/KEY: misc_feature
<222> LOCATION: (1)..(498)
<223> OTHER INFORMATION: Vhb04

<400> SEQUENCE: 12

| | | |
|---|---|---|
| atggtatctc agaaaacaat tgaaattgtc aaagctactg cacctattat ccgtgaaaag | 60 |
| ggtgaagaaa ttaccagacg catgtatgaa attacgtttg cggagcgccc agactacaag | 120 |
| cgtggattcg agactacgtg gatgcagcat ttggacggtg gcgaacaggc cataaactt | 180 |
| gcagcagcgg tttatgctta tgctacccat attgatcgct tggatgaact cgcaatggct | 240 |
| gttaaaacta ttgcgcatcg acatgtacag actcggacgc taccggagca atatccgctt | 300 |
| attggtgaaa agcttcttca agcgatgaaa gatgttctgc aagatgctgc gactgatgaa | 360 |
| gtgattagtg cgtgggcgga agcttacact gctttggctg acatcttcat ccagaaagaa | 420 |
| aaagcgatct atcagcaaga gatcgtgag cttactgagc aacttgctaa agctaataag | 480 |
| ccagaaacgt ccggatag | 498 |

<210> SEQ ID NO 13
<211> LENGTH: 513
<212> TYPE: DNA
<213> ORGANISM: Candidatus Entotheonella sp. TSY1
<220> FEATURE:
<221> NAME/KEY: misc_feature
<222> LOCATION: (1)..(513)
<223> OTHER INFORMATION: Vhb05

<400> SEQUENCE: 13

| | | |
|---|---|---|
| atgaatttta tgtctaaaact ttatggatt ctcacgttgg gccgtactgc gttgcttccg | 60 |
| atgccttctg cggagtctaa agttgatggt tcaatttccg ctcgccaggc atggcttgta | 120 |
| cagtctagtt ggaaacatgt tcggccaatt gctgatcagg ctgctacgct tttctatgat | 180 |
| aagcttttcg aattggaccc aagtatcaaa ccgcttttcg cacatactga gatgaaagaa | 240 |
| caacagaaaa agctaatgca aactatgaca gtagtcgtaa acggtcttaa tcgcctagat | 300 |
| aaaatggttc cagcggtgca agctttgggc aagcgtcata ttgattatgg tgtccaagct | 360 |
| gaccattact caaccgtggg ggcagcgctt ctgtggactc ttcaacaggg acttggagag | 420 |
| gcatttaccc ctgaagtcga agaagcgtgg tccgttacgt acactgtact ggcgggtacg | 480 |
| atgcagggtg ctgcggctga agtgactgtt tag | 513 |

<210> SEQ ID NO 14
<211> LENGTH: 429
<212> TYPE: DNA
<213> ORGANISM: Hassallia byssoidea VB512170
<220> FEATURE:
<221> NAME/KEY: misc_feature
<222> LOCATION: (1)..(429)
<223> OTHER INFORMATION: Vhb06

<400> SEQUENCE: 14

| | | |
|---|---|---|
| atgtcccta atgttgagct tcttgaacaa tcatttgaac agattaaacc acgcgcgaat | 60 |
| gacttcgttg caagttttta cgaaaacttg ttcgcaacac atccagaagt aaaaccgctt | 120 |
| tttgcgcata ccaatatggt agagcagcgt aagcatctca ttgcggcgct tgtattggtt | 180 |
| attcagaatc tacgtaagcc tgaagtcctt ggatctgctc ttaaaacgtt gggagcgaaa | 240 |
| catgtcggat atggtacgat cccggaacat tatccagctg tgggcgaagc tctgctaact | 300 |
| actttcgagc agtatctgca tcaagattgg acgcctgaag tgaaacaagc ttgggttgat | 360 |

-continued

```
gctcttactg caatcaccgc tcttatgctt aagggtgcgg gtgaggatta cgctttgctt    420
actgtgtag                                                             429
```

<210> SEQ ID NO 15
<211> LENGTH: 462
<212> TYPE: DNA
<213> ORGANISM: Unknown
<220> FEATURE:
<223> OTHER INFORMATION: mine drainage metagenome
<220> FEATURE:
<221> NAME/KEY: misc_feature
<222> LOCATION: (1)..(462)
<223> OTHER INFORMATION: Vhb07

<400> SEQUENCE: 15

```
atggctatta atattcaact aattcagagt tccggagcgg cagtcaaaga ccttggtgta     60
ccagtcgctg agcatttcta taactatatg ttcacgcatt tcccagaagt gcgtaaaatg    120
tttcctggtg atatgacaga gcagcgtgtt cgcttgttta actcagttat cttgattgcg    180
actaatatcg atactatgga agtacttgtg ccgtatttga aagaactcgg cattggacat    240
atcaaatatg atactcgccc cgaacattac ccgattgttg gtaagtctct tcttaatact    300
cttaagcatt ttctgggaga agcgtggacc caagaaatgg ctgagtcttg gatcgaagcg    360
tataatcttg ctagtacggt ttgtattgaa gcggcttacg aagctatggc accttctcgg    420
ttcgtaccgg ttacgattga cgatgtacct ccagcagtgt ag                       462
```

<210> SEQ ID NO 16
<211> LENGTH: 450
<212> TYPE: DNA
<213> ORGANISM: Aeromonas molluscorum 848
<220> FEATURE:
<221> NAME/KEY: misc_feature
<222> LOCATION: (1)..(450)
<223> OTHER INFORMATION: Vhb08

<400> SEQUENCE: 16

```
atgaccttcg atgaaattga cctagtacag cgcgcttgga gtcgtatctc tcttttctcc     60
aatgcatttg ttagagagat ttatcaagaa cttttttcgct tggatgaacg tttggaaact    120
atgttcagtc taacagatga tcgccttatc gataaagttg cgcagacttt gaatacggtc    180
cttacgtctt tggagcaact ggattcactt cgattcatta ttcgccatct tggagaacgg    240
catcgtcagt atggtgttct tccggcgcat tttgaccttg tgaaggaagc gatgactcgt    300
gtaatggctt gtcgtcttgg agaatacttt acgcctgctc ttgcactcgc gtggtccggt    360
gcttatgatg aaattgctgc gattatgatc gaaggcctgc aggctgagga accatgtact    420
gagggtgcag atatggacat ttctcaatag                                      450
```

<210> SEQ ID NO 17
<211> LENGTH: 411
<212> TYPE: DNA
<213> ORGANISM: Phaeobacter gallaeciensis DSM 26640
<220> FEATURE:
<221> NAME/KEY: misc_feature
<222> LOCATION: (1)..(411)
<223> OTHER INFORMATION: Vhb09

<400> SEQUENCE: 17

```
atggtgtctg aagatggtcg tactcttatt cataaatctg tcgaatctga acgtatggaa     60
ttggatcatt ttgttcgcct cttttatgcg aagtttttcg agatttgtcc agacgtacgc    120
```

-continued

```
gcgcttttcc ctaatgatat ggcaagtcaa catgaaaagc tacttacttc attgacgcat      180
atcatcgaag cgcttgacca tccagagaaa cttagtgcaa tccttaaaca tcagggcgaa      240
cggcatcgcg cgattcagat tactgatgcg catttcgatg gattcattca ttcttttact      300
ggtgctctgg ctgacattct gggaccggag tggtccgaag atacgcattc agcttggcgt      360
tcctttctta ccgatgttgc tcttaacatg aatttcttgc gaacagctta g               411
```

<210> SEQ ID NO 18
<211> LENGTH: 414
<212> TYPE: DNA
<213> ORGANISM: Spirosoma radiotolerans
<220> FEATURE:
<221> NAME/KEY: misc_feature
<222> LOCATION: (1)..(414)
<223> OTHER INFORMATION: Vhb10

<400> SEQUENCE: 18

```
atgacaaatc aacagcttac cctagttaaa cagtcctgga ctcttcttcg cgaagttgat       60
cctgcaattc ttggtgatgt attctatggt agattgtttt tcaattaccc taatctgcgt      120
ccgctcttta aaggcccaat ggatcgacag tatcaaaagt tcattgacat gcttagtatc      180
cttgtagcgc gtctagaccg tccgtatgct gttgagcaag aaatttcaca gttgggacag      240
tctcatgctc aatatgggat taagccagaa cattacgaac cagtgaaaga tgcgttgctg      300
tggactttgg agcgtggtct tggaaatgat tggaacgatg acgtccgcca gggttggatc      360
gcgtgttatg atcggcttac gcgcgctatg cttggacgcg aaaacaatct ttag            414
```

<210> SEQ ID NO 19
<211> LENGTH: 423
<212> TYPE: DNA
<213> ORGANISM: Shewanella loihica (strain ATCC BAA-1088 / PV-4)
<220> FEATURE:
<221> NAME/KEY: misc_feature
<222> LOCATION: (1)..(423)
<223> OTHER INFORMATION: Vhb11

<400> SEQUENCE: 19

```
atgccgctta ccgatgagca aaacaacttt attcagaagt ccttcgctga gatcaatcgc       60
cagaattcaa actttgcgtc ccatttctac gattgtcttt ttgctatggc gcctttgatt      120
cgaccaatgt ttcagagtga gcgtccggta tttgagtatc atttcaatga actaattact      180
acggcagtgg caaaagttca tcagttcaat gaagttaaac caaaacttga agaattggga      240
cgcaagcatc ttgattatgg tgtcaatatc tctcaattcg aagttgtacg ggctgctttg      300 ctgcttttcta ttcaggattg tctccgtgac gcttcatctc ctgcgattga acaggcttgg      360
tcttgttatt cgacgaaat tgcaaaagtg atgatcgcgg ctatgcaaga agcggcgagt      420
tag                                                                    423
```

<210> SEQ ID NO 20
<211> LENGTH: 429
<212> TYPE: DNA
<213> ORGANISM: Sulfurimonas gotlandica (strain DSM 19862 / JCM 16533 / GD1)
<220> FEATURE:
<221> NAME/KEY: misc_feature
<222> LOCATION: (1)..(429)
<223> OTHER INFORMATION: Vhb12

<400> SEQUENCE: 20

```
atggaactgt ctgctaaaac tatcgaaatt gtgaaggcta ctgcaccaat gttgctgcg        60
```

```
aatgctgaag ctattacgtc cactatgtac aagattatgt ttacgaacca tccggaaatc    120
aaagaacttt tcaaagatgc gaagcctgat cagcataaga aattggctgc agcggtcgga    180
gcgtatgcag ctaatatcga caatctgatt gtccttgaaa aagcgattga gaaaatggta    240
tcaacacata tccttaaaaa tgtgcagcca gagcattatc cgattgttgg cattagtatt    300
cttgaggcta tcaaaaaagt gttgggtgac gctgttaccc tcgaagtact tgatgcgtgg    360
aaagaagcat atttctttt ggcgcatgta ctaattgagc aagaaaagct tgcgtacgct    420
gatgtttag                                                             429
```

<210> SEQ ID NO 21
<211> LENGTH: 77
<212> TYPE: DNA
<213> ORGANISM: Corynebacterium glutamicum
<220> FEATURE:
<223> OTHER INFORMATION: T1 termination sequence

<400> SEQUENCE: 21

```
gcattttag tacgtgcaat aaccactctg gttttccag ggtggttttt tgatgccctt     60
tttggagtct tcaactg                                                    77
```

<210> SEQ ID NO 22
<211> LENGTH: 74
<212> TYPE: DNA
<213> ORGANISM: Corynebacterium glutamicum
<220> FEATURE:
<223> OTHER INFORMATION: T2 termination sequence

<400> SEQUENCE: 22

```
acaatagtaa aaggaaccct cacgaactgt gagggttcct tttttgggtt tcgccggagg    60
agacgtcgaa aagc                                                       74
```

<210> SEQ ID NO 23
<211> LENGTH: 146
<212> TYPE: PRT
<213> ORGANISM: Vitreoscilla stercoraria
<220> FEATURE:
<221> NAME/KEY: MISC_FEATURE
<222> LOCATION: (1)..(146)
<223> OTHER INFORMATION: Vhb01

<400> SEQUENCE: 23

```
Met Leu Asp Gln Gln Thr Ile Asn Ile Ile Lys Ala Thr Val Pro Val
1               5                   10                  15

Leu Lys Glu His Gly Val Thr Ile Thr Thr Thr Phe Tyr Lys Asn Leu
            20                  25                  30

Phe Ala Lys His Pro Glu Val Arg Pro Leu Phe Asp Met Gly Arg Gln
        35                  40                  45

Glu Ser Leu Glu Gln Pro Lys Ala Leu Ala Met Thr Val Leu Ala Ala
    50                  55                  60

Ala Gln Asn Ile Glu Asn Leu Pro Ala Ile Leu Pro Ala Val Lys Lys
65                  70                  75                  80

Ile Ala Val Lys His Cys Gln Ala Gly Val Ala Ala His Tyr Pro
                85                  90                  95

Ile Val Gly Gln Glu Leu Leu Gly Ala Ile Lys Glu Val Leu Gly Asp
            100                 105                 110

Ala Ala Thr Asp Asp Ile Leu Asp Ala Trp Gly Lys Ala Tyr Gly Val
        115                 120                 125

Ile Ala Asp Val Phe Ile Gln Val Glu Ala Asp Leu Tyr Ala Gln Ala
```

```
            130                 135                 140

Val Glu
145

<210> SEQ ID NO 24
<211> LENGTH: 136
<212> TYPE: PRT
<213> ORGANISM: Gordonia terrae C-6
<220> FEATURE:
<221> NAME/KEY: MISC_FEATURE
<222> LOCATION: (1)..(136)
<223> OTHER INFORMATION: Vhb02

<400> SEQUENCE: 24

Met Leu Asn Arg Glu Val Leu Gln Asp Ser Leu Ser Leu Val Ile Asp
1               5                   10                  15

Asp Glu Gln Lys Leu Met Leu Ser Phe Tyr Asp Arg Leu Phe Glu Glu
            20                  25                  30

His Pro Glu Val Arg Pro Met Phe Gly Ala Asp Leu Arg Pro Gln Ala
        35                  40                  45

Thr Met Leu Gln Gln Ala Ile Ala Ala Val Leu Asp His Leu Asp Asp
    50                  55                  60

Thr Glu Trp Leu Gly Arg Thr Leu Gly Ala Leu Gly Arg Arg His Ala
65                  70                  75                  80

Asp Leu Gly Val Thr Pro Glu Met Tyr Gly Trp Val Ala Gly Ala Leu
                85                  90                  95

Ile Thr Thr Met Ala Glu Arg Gly Gly Gly Asp Trp Thr Asp Glu Met
            100                 105                 110

Thr Ala Ala Trp Thr Glu Ala Leu Gly Ala Val Ala Gly Leu Met Leu
        115                 120                 125

Asp Ala Tyr Pro Ala Val Ala Asp
        130                 135

<210> SEQ ID NO 25
<211> LENGTH: 140
<212> TYPE: PRT
<213> ORGANISM: Sandaracinus amylolyticus
<220> FEATURE:
<221> NAME/KEY: MISC_FEATURE
<222> LOCATION: (1)..(140)
<223> OTHER INFORMATION: Vhb03

<400> SEQUENCE: 25

Met Ser Leu Asp Val Pro Leu Leu Arg Ser Ser Phe Glu Leu Val Leu
1               5                   10                  15

Glu Arg Glu Pro Ala Leu Thr Ala Arg Phe Tyr Glu Ile Leu Phe Glu
            20                  25                  30

Arg Tyr Pro Gln Ala Arg Pro Leu Phe Ala Arg Asn Ala Arg Lys Gln
        35                  40                  45

Gln Glu Glu Met Leu Ala Arg Ala Leu Ala Ala Val Val Asp Arg Leu
    50                  55                  60

Glu Asp Ala Pro Trp Leu Val Glu Thr Leu Gly Ala Met Gly Ala Lys
65                  70                  75                  80

His Val Asp Tyr Gly Val Thr Glu Met Tyr Gly Trp Val Gly Asp
                85                  90                  95

Ala Leu Leu Arg Thr Leu Ala Glu Val Ala Gly Asp Ala Trp Thr Pro
            100                 105                 110

Glu Leu Glu Ala Ala Trp Ala Ala Ala Tyr Gly Ala Ile Arg Asp Leu
        115                 120                 125
```

Met Leu Ala Gly Ala Ser Arg Ala Gln Ala Ala Glu
    130                 135                 140

<210> SEQ ID NO 26
<211> LENGTH: 165
<212> TYPE: PRT
<213> ORGANISM: Fischerella sp. JSC-11
<220> FEATURE:
<221> NAME/KEY: MISC_FEATURE
<222> LOCATION: (1)..(165)
<223> OTHER INFORMATION: Vhb04

<400> SEQUENCE: 26

Met Val Ser Gln Lys Thr Ile Glu Ile Val Lys Ala Thr Ala Pro Ile
1               5                   10                  15

Ile Arg Glu Lys Gly Glu Ile Thr Arg Arg Met Tyr Glu Ile Thr
            20                  25                  30

Phe Ala Glu Arg Pro Asp Tyr Lys Arg Gly Phe Glu Thr Thr Trp Met
            35                  40                  45

Gln His Leu Asp Gly Gly Glu Gln Ala His Lys Leu Ala Ala Ala Val
        50                  55                  60

Tyr Ala Tyr Ala Thr His Ile Asp Arg Leu Asp Glu Leu Ala Met Ala
65                  70                  75                  80

Val Lys Thr Ile Ala His Arg His Val Gln Thr Arg Thr Leu Pro Glu
                85                  90                  95

Gln Tyr Pro Leu Ile Gly Glu Lys Leu Leu Gln Ala Met Lys Asp Val
            100                 105                 110

Leu Gln Asp Ala Ala Thr Asp Glu Val Ile Ser Ala Trp Ala Glu Ala
        115                 120                 125

Tyr Thr Ala Leu Ala Asp Ile Phe Ile Gln Lys Glu Lys Ala Ile Tyr
    130                 135                 140

Gln Gln Glu Asp Arg Glu Leu Thr Gln Leu Ala Lys Ala Asn Lys
145                 150                 155                 160

Pro Glu Thr Ser Gly
                165

<210> SEQ ID NO 27
<211> LENGTH: 170
<212> TYPE: PRT
<213> ORGANISM: Candidatus Entotheonella sp. TSY1
<220> FEATURE:
<221> NAME/KEY: MISC_FEATURE
<222> LOCATION: (1)..(170)
<223> OTHER INFORMATION: Vhb05

<400> SEQUENCE: 27

Met Asn Phe Met Ser Lys Leu Tyr Gly Phe Leu Thr Leu Gly Arg Thr
1               5                   10                  15

Ala Leu Leu Pro Met Pro Ser Ala Glu Ser Lys Val Asp Gly Ser Ile
            20                  25                  30

Ser Ala Arg Gln Ala Trp Leu Val Gln Ser Ser Trp Lys His Val Arg
        35                  40                  45

Pro Ile Ala Asp Gln Ala Ala Thr Leu Phe Tyr Asp Lys Leu Phe Glu
    50                  55                  60

Leu Asp Pro Ser Ile Lys Pro Leu Phe Ala His Thr Glu Met Lys Glu
65                  70                  75                  80

Gln Gln Lys Lys Leu Met Gln Thr Met Thr Val Val Asn Gly Leu
                85                  90                  95

```
Asn Arg Leu Asp Lys Met Val Pro Ala Val Gln Ala Leu Gly Lys Arg
            100                 105                 110

His Ile Asp Tyr Gly Val Gln Ala Asp His Tyr Ser Thr Val Gly Ala
            115                 120                 125

Ala Leu Leu Trp Thr Leu Gln Gln Gly Leu Gly Glu Ala Phe Thr Pro
        130                 135                 140

Glu Val Glu Glu Ala Trp Ser Val Thr Tyr Thr Val Leu Ala Gly Thr
145                 150                 155                 160

Met Gln Gly Ala Ala Ala Glu Val Thr Val
                165                 170
```

```
<210> SEQ ID NO 28
<211> LENGTH: 142
<212> TYPE: PRT
<213> ORGANISM: Hassallia byssoidea VB512170
<220> FEATURE:
<221> NAME/KEY: MISC_FEATURE
<222> LOCATION: (1)..(142)
<223> OTHER INFORMATION: Vhb06

<400> SEQUENCE: 28
```

```
Met Ser Leu Asn Val Glu Leu Leu Gln Ser Phe Glu Gln Ile Lys
1               5                   10                  15

Pro Arg Ala Asn Asp Phe Val Ala Ser Phe Tyr Glu Asn Leu Phe Ala
            20                  25                  30

Thr His Pro Glu Val Lys Pro Leu Phe Ala His Thr Asn Met Val Glu
        35                  40                  45

Gln Arg Lys His Leu Ile Ala Ala Leu Val Leu Val Ile Gln Asn Leu
    50                  55                  60

Arg Lys Pro Glu Val Leu Gly Ser Ala Leu Lys Thr Leu Gly Ala Lys
65                  70                  75                  80

His Val Gly Tyr Gly Thr Ile Pro Glu His Tyr Pro Ala Val Gly Glu
                85                  90                  95

Ala Leu Leu Thr Thr Phe Glu Gln Tyr Leu His Gln Asp Trp Thr Pro
            100                 105                 110

Glu Val Lys Gln Ala Trp Val Asp Ala Leu Thr Ala Ile Thr Ala Leu
        115                 120                 125

Met Leu Lys Gly Ala Gly Glu Asp Tyr Ala Leu Leu Thr Val
    130                 135                 140
```

```
<210> SEQ ID NO 29
<211> LENGTH: 153
<212> TYPE: PRT
<213> ORGANISM: Unknown
<220> FEATURE:
<223> OTHER INFORMATION: mine drainage metagenome
<220> FEATURE:
<221> NAME/KEY: MISC_FEATURE
<222> LOCATION: (1)..(153)
<223> OTHER INFORMATION: Vhb07

<400> SEQUENCE: 29
```

```
Met Ala Ile Asn Ile Gln Leu Ile Gln Ser Ser Gly Ala Ala Val Lys
1               5                   10                  15

Asp Leu Gly Val Pro Val Ala Glu His Phe Tyr Asn Tyr Met Phe Thr
            20                  25                  30

His Phe Pro Glu Val Arg Lys Met Phe Pro Gly Asp Met Thr Glu Gln
        35                  40                  45

Arg Val Arg Leu Phe Asn Ser Val Ile Leu Ile Ala Thr Asn Ile Asp
    50                  55                  60
```

```
Thr Met Glu Val Leu Val Pro Tyr Leu Lys Glu Leu Gly Ile Gly His
65                  70                  75                  80

Ile Lys Tyr Asp Thr Arg Pro Glu His Tyr Pro Ile Val Gly Lys Ser
                85                  90                  95

Leu Leu Asn Thr Leu Lys His Phe Leu Gly Ala Trp Thr Gln Glu
            100                 105                 110

Met Ala Glu Ser Trp Ile Glu Ala Tyr Asn Leu Ala Ser Thr Val Cys
            115                 120                 125

Ile Glu Ala Ala Tyr Glu Ala Met Ala Pro Ser Arg Phe Val Pro Val
            130                 135                 140

Thr Ile Asp Asp Val Pro Pro Ala Val
145                 150
```

<210> SEQ ID NO 30
<211> LENGTH: 149
<212> TYPE: PRT
<213> ORGANISM: Aeromonas molluscorum 848
<220> FEATURE:
<221> NAME/KEY: MISC_FEATURE
<222> LOCATION: (1)..(149)
<223> OTHER INFORMATION: Vhb08

<400> SEQUENCE: 30

```
Met Thr Phe Asp Glu Ile Asp Leu Val Gln Arg Ala Trp Ser Arg Ile
1               5                   10                  15

Ser Leu Phe Ser Asn Ala Phe Val Arg Glu Ile Tyr Gln Glu Leu Phe
                20                  25                  30

Arg Leu Asp Glu Arg Leu Glu Thr Met Phe Ser Leu Thr Asp Asp Arg
                35                  40                  45

Leu Ile Asp Lys Val Ala Gln Thr Leu Asn Thr Val Leu Thr Ser Leu
    50                  55                  60

Glu Gln Leu Asp Ser Leu Arg Phe Ile Ile Arg His Leu Gly Glu Arg
65                  70                  75                  80

His Arg Gln Tyr Gly Val Leu Pro Ala His Phe Asp Leu Val Lys Glu
                85                  90                  95

Ala Met Thr Arg Val Met Ala Cys Arg Leu Gly Glu Tyr Phe Thr Pro
            100                 105                 110

Ala Leu Ala Leu Ala Trp Ser Gly Ala Tyr Asp Glu Ile Ala Ala Ile
            115                 120                 125

Met Ile Glu Gly Leu Gln Ala Glu Pro Cys Thr Glu Gly Ala Asp
            130                 135                 140

Met Asp Ile Ser Gln
145
```

<210> SEQ ID NO 31
<211> LENGTH: 136
<212> TYPE: PRT
<213> ORGANISM: Phaeobacter gallaeciensis DSM 26640
<220> FEATURE:
<221> NAME/KEY: MISC_FEATURE
<222> LOCATION: (1)..(136)
<223> OTHER INFORMATION: Vhb09

<400> SEQUENCE: 31

```
Met Val Ser Glu Asp Gly Arg Thr Leu Ile His Lys Ser Val Glu Ser
1               5                   10                  15

Glu Arg Met Glu Leu Asp His Phe Val Arg Leu Phe Tyr Ala Lys Phe
                20                  25                  30
```

```
Phe Glu Ile Cys Pro Asp Val Arg Ala Leu Phe Pro Asn Asp Met Ala
         35                  40                  45

Ser Gln His Glu Lys Leu Leu Thr Ser Leu Thr His Ile Ile Glu Ala
 50                  55                  60

Leu Asp His Pro Glu Lys Leu Ser Ala Ile Leu Lys His Gln Gly Glu
65                  70                  75                  80

Arg His Arg Ala Ile Gln Ile Thr Asp Ala His Phe Asp Gly Phe Ile
                 85                  90                  95

His Ser Phe Thr Gly Ala Leu Ala Asp Ile Leu Gly Pro Glu Trp Ser
            100                 105                 110

Glu Asp Thr His Ser Ala Trp Arg Ser Phe Leu Thr Asp Val Ala Leu
        115                 120                 125

Asn Met Asn Phe Leu Arg Thr Ala
    130                 135

<210> SEQ ID NO 32
<211> LENGTH: 137
<212> TYPE: PRT
<213> ORGANISM: Spirosoma radiotolerans
<220> FEATURE:
<221> NAME/KEY: MISC_FEATURE
<222> LOCATION: (1)..(137)
<223> OTHER INFORMATION: Vhb10

<400> SEQUENCE: 32

Met Thr Asn Gln Gln Leu Thr Leu Val Lys Gln Ser Trp Thr Leu Leu
1                5                  10                  15

Arg Glu Val Asp Pro Ala Ile Leu Gly Asp Val Phe Tyr Gly Arg Leu
                20                  25                  30

Phe Phe Asn Tyr Pro Asn Leu Arg Pro Leu Phe Lys Gly Pro Met Asp
             35                  40                  45

Arg Gln Tyr Gln Lys Phe Ile Asp Met Leu Ser Ile Leu Val Ala Arg
 50                  55                  60

Leu Asp Arg Pro Tyr Ala Val Glu Gln Glu Ile Ser Gln Leu Gly Gln
65                  70                  75                  80

Ser His Ala Gln Tyr Gly Ile Lys Pro Glu His Tyr Glu Pro Val Lys
                 85                  90                  95

Asp Ala Leu Leu Trp Thr Leu Glu Arg Gly Leu Gly Asn Asp Trp Asn
            100                 105                 110

Asp Asp Val Arg Gln Gly Trp Ile Ala Cys Tyr Asp Arg Leu Thr Arg
        115                 120                 125

Ala Met Leu Gly Arg Glu Asn Asn Leu
    130                 135

<210> SEQ ID NO 33
<211> LENGTH: 140
<212> TYPE: PRT
<213> ORGANISM: Shewanella loihica (strain ATCC BAA-1088 / PV-4)
<220> FEATURE:
<221> NAME/KEY: MISC_FEATURE
<222> LOCATION: (1)..(140)
<223> OTHER INFORMATION: Vhb11

<400> SEQUENCE: 33

Met Pro Leu Thr Asp Glu Gln Lys Gln Leu Ile Gln Lys Ser Phe Ala
1                5                  10                  15

Glu Ile Asn Arg Gln Asn Ser Asn Phe Ala Ser His Phe Tyr Asp Cys
                20                  25                  30

Leu Phe Ala Met Ala Pro Leu Ile Arg Pro Met Phe Gln Ser Glu Arg
```

```
                35                  40                  45
Pro Val Phe Glu Tyr His Phe Asn Glu Leu Ile Thr Thr Ala Val Ala
        50                  55                  60

Lys Val His Gln Phe Asn Glu Val Lys Pro Lys Leu Glu Glu Leu Gly
65                  70                  75                  80

Arg Lys His Leu Asp Tyr Gly Val Asn Ile Ser Gln Phe Glu Val Val
                85                  90                  95

Arg Ala Ala Leu Leu Leu Ser Ile Gln Asp Cys Leu Arg Asp Ala Ser
                100                 105                 110

Ser Pro Ala Ile Glu Gln Ala Trp Ser Cys Tyr Tyr Asp Glu Ile Ala
            115                 120                 125

Lys Val Met Ile Ala Ala Met Gln Glu Ala Ala Ser
            130                 135                 140

<210> SEQ ID NO 34
<211> LENGTH: 142
<212> TYPE: PRT
<213> ORGANISM: Sulfurimonas gotlandica (strain DSM 19862 / JCM 16533 /
      GD1)
<220> FEATURE:
<221> NAME/KEY: MISC_FEATURE
<222> LOCATION: (1)..(142)
<223> OTHER INFORMATION: Vhb12

<400> SEQUENCE: 34

Met Glu Leu Ser Ala Lys Thr Ile Glu Ile Val Lys Ala Thr Ala Pro
1               5                   10                  15

Ile Val Ala Ala Asn Ala Glu Ala Ile Thr Ser Thr Met Tyr Lys Ile
                20                  25                  30

Met Phe Thr Asn His Pro Glu Ile Lys Glu Leu Phe Lys Asp Ala Lys
            35                  40                  45

Pro Asp Gln His Lys Lys Leu Ala Ala Val Gly Ala Tyr Ala Ala
        50                  55                  60

Asn Ile Asp Asn Leu Ile Val Leu Glu Lys Ala Ile Glu Lys Met Val
65                  70                  75                  80

Ser Thr His Ile Leu Lys Asn Val Gln Pro Glu His Tyr Pro Ile Val
                85                  90                  95

Gly Ile Ser Ile Leu Glu Ala Ile Lys Lys Val Leu Gly Asp Ala Val
                100                 105                 110

Thr Leu Glu Val Leu Asp Ala Trp Lys Glu Ala Tyr Phe Phe Leu Ala
            115                 120                 125

His Val Leu Ile Glu Gln Glu Lys Leu Ala Tyr Ala Asp Val
            130                 135                 140
```

METHODS FOR GENERATING A BACTERIAL HEMOGLOBIN LIBRARY AND USES THEREOF

CROSS REFERENCE TO RELATED APPLICATONS

This application is a national phase of International Application No. PCT/US2017/039772, filed Jun. 28, 2017, which claims the benefit of priority to U.S. Provisional Application Serial No. 62/356,934, filed Jun. 30, 2016, each of which is herein incorporated by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ZYMR_006_01WO_ST25.txt. The text file is 29 KB, was created on Jun. 28, 2017, and is being submitted electronically via EFS-Web.

FIELD

The present disclosure is directed to microbial genomic engineering. The disclosed genomic engineering method entails the generation of a library of prokaryotic hemoglobin genes and introducing said library into microbial hosts, in order to produce strains capable of producing a product of interest while growing in oxygen poor or substantially anaerobic conditions.

BACKGROUND

The commercial production of a variety of desirable metabolites and important pharmaceuticals can employ the overexpression capacity of oxygen-requiring bacteria, fungi and mammalian cells. Further, during the optimization of a process (e.g., fermentation) for producing a commercial product involving a facultative aerobe or a product pathway that requires oxygen, oxygen delivery to the microbe often becomes rate limiting. This can largely be due to the incredibly low surface area to volume ratio of industrial scale processes (e.g., fermentations). Oxygen has very low solubility in water and various microorganisms and cultured cell types have high nutritional demand for oxygen, especially during large-scale and high-cell-density production processes. The high demand for oxygen can be partially satisfied by improving process parameters and bioreactor configurations, e.g. improved mixing rates, high-efficiency dispersion systems and modifications of the medium, which can all serve to increase the partial pressure of oxygen in the production medium. However, these improvements often directly contribute to the capital and operating cost of running the production process. Further, such improvements often employ methods that can produce undesirable rheological properties such as turbulence and/or shear rates in the culture vessel as well as utilize culture media that may produce suboptimal growth rates for a desired host microorganism.

Thus, there is a great need in the art for creative solutions to the problem of oxygen limitation in industrial fermentations, which are widely applicable to a range of microorganisms and are not dependent upon optimizing physical bioreactor components or fermentation media.

SUMMARY OF THE DISCLOSURE

The present disclosure overcomes the aforementioned limitations by taking a genetic engineering approach to alleviate the adverse effects of oxygen limitation on microorganisms in industrial fermentations. Specifically, the disclosure provides a library approach to solving the problem of a limited oxygen environment in industrial fermentations. For instance, in an embodiment, the disclosure provides for testing heterologous bacterial hemoglobin and/or flavohemoglobin genes in industrial microbes and assessing the effect of the introduction on, inter alia, increasing the partial pressure of oxygen, growth, and/or productivity, in the industrial microbes.

In one aspect, provided herein is a host cell comprising a heterologous bacterial hemoglobin gene functionally linked to a first promoter polynucleotide, wherein the first promoter polynucleotide comprises a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In some cases, the bacterial hemoglobin gene is a gene with a nucleotide sequence selected from SEQ ID NO: 12, SEQ ID NO: 10, SEQ ID NO: 11, SEQ ID NO: 9, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20. In some cases, the bacterial hemoglobin gene encodes a polypeptide with an amino acid sequence selected from SEQ ID NO: 26, SEQ ID NO: 24, SEQ ID NO: 25, SEQ ID NO: 23, SEQ ID NO: 27, SEQ ID NO: 28, SEQ ID NO: 29, SEQ ID NO: 30, SEQ ID NO: 31, SEQ ID NO: 32, SEQ ID NO: 33 or SEQ ID NO: 34. In some cases, the bacterial hemoglobin gene is from a strain, species, or sub-species of a microorganism listed in Table 2. In some cases, the bacterial hemoglobin gene is a bacterial flavohemoglobin gene. In some cases, the bacterial flavohemoglobin gene is from a strain, species, or sub-species of a microorganism listed in Table 2. In some cases, the host cell belongs to the genus *Corynebacterium*. In some cases, the host cell is *Corynebacterium glutamicum*. In some cases, the host cell is used in a method of producing a biomolecule comprising culturing the host cell under conditions suitable for producing the biomolecule. In some cases, the biomolecule is a small molecule, an amino acid, a nucleotide, an organic acid, or an alcohol. In some cases, the amino acid is lysine, glutamic acid, tyrosine, phenylalanine, tryptophan, aspartic acid, asparagine, threonine, isoleucine, or methionine. In some cases, the organic acid is succinate, lactate or pyruvate. In some cases, the alcohol is ethanol or isobutanol.

In another aspect, provided herein is a method for generating a microorganism capable of increased production of a biomolecule, the method comprising: a) genetically modifying a host microorganism, wherein the modifying comprises introducing a bacterial hemoglobin gene from a library of bacterial hemoglobin genes into the genome of the host microorganism, wherein each bacterial hemoglobin gene from the library of bacterial hemoglobin genes is functionally linked to a promoter comprising a nucleotide sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8 and wherein the modification generates a strain of the host microorganism expressing the bacterial hemoglobin gene; b) repeating step a) for a plurality of rounds until a plurality of strains of the host microorganism are generated, wherein each strain of the plurality of strains of the host microorganism expresses a separate bacterial hemoglobin gene from the library of bacterial hemoglobin genes; c) contacting each strain of the plurality of strains of the host microorganism with a carbon source under fermentative conditions; and d) selecting each strain of the host microorganism that produces an increased amount of a biomolecule as compared to the amount of the biomolecule produced from a control microorganism, wherein the control microorganism does not express a bacterial hemoglobin gene from the library of bacterial hemoglobin genes. In some cases, the library of bacterial hemoglobin genes comprises one or more bacterial hemoglobin genes with a nucleotide sequence selected from SEQ ID NO: 12, SEQ ID NO: 10, SEQ ID NO: 11, SEQ ID NO: 9, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20. In some cases, the library of bacterial hemoglobin genes comprises one or more bacterial hemoglobin genes that encode one or more polypeptide sequences selected from SEQ ID NO: 26, SEQ ID NO: 24, SEQ ID NO: 25, SEQ ID NO: 23, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34. In some cases, the library of bacterial hemoglobin genes comprises one or more bacterial hemoglobin genes from a strain, species, or sub-species of a microorganism listed in Table 2. In some cases, the bacterial hemoglobin gene is a bacterial flavohemoglobin gene. In some cases, the library of bacterial flavohemoglobin genes comprises one or more bacterial flavohemoglobin genes from a strain, species, or sub-species of a microorganism listed in Table 2. In some cases, at least one of the bacterial hemoglobins in the library of hemoglobins is a bacterial flavohemoglobin. In some cases, the library of bacterial hemoglobin genes comprises one or more bacterial hemoglobin genes from a strain, species, or sub-species of a microorganism listed in Table 2 and one or more bacterial flavohemoglobin genes from a strain, species, or sub-species of a microorganism listed in Table 2. In some cases, the host microorganism belongs to the genus *Corynebacterium*. In some cases, the host microorganism is *Corynebacterium glutamicum*. In some cases, the introducing is performed by transformation, transduction or electroporation. In some cases, the biomolecule is a small molecule, an amino acid, a nucleotide, an organic acid, or an alcohol. In some cases, the amino acid is lysine, glutamic acid, tyrosine, phenylalanine, tryptophan, aspartic acid, asparagine, threonine, isoleucine, or methionine. In some cases, the organic acid is succinate, lactate or pyruvate. In some cases, the alcohol is ethanol or isobutanol.

In yet another aspect, provided herein is a library of bacterial hemoglobin genes, wherein each bacterial hemoglobin gene in the library of bacterial hemoglobin genes is functionally linked to a promoter comprising a nucleotide sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In some cases, the library of bacterial hemoglobin genes comprises one or more bacterial hemoglobin genes with a nucleotide sequence selected from SEQ ID NO: 12, SEQ ID NO: 10, SEQ ID NO: 11, SEQ ID NO: 9, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20. In some cases, the library of bacterial hemoglobin genes comprises one or more bacterial hemoglobin genes that encode one or more polypeptide sequences selected from SEQ ID NO: 26, SEQ ID NO: 24, SEQ ID NO: 25, SEQ ID NO: 23, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34. In some cases, the library of bacterial hemoglobin genes comprises one or more bacterial hemoglobin genes from a strain, species, or sub-species of a microorganism listed in Table 2. In some cases, each of the bacterial hemoglobin genes in the library is a bacterial flavohemoglobin gene. In some cases, the library of bacterial flavohemoglobin genes comprises one or more bacterial flavohemoglobin genes from a strain, species, or sub-species of a microorganism listed in Table 2. In some cases, at least one of the bacterial hemoglobin genes in the library of bacterial hemoglobin genes is a bacterial flavohemoglobin gene. In some cases, the library of bacterial hemoglobin genes comprises one or more bacterial hemoglobin genes from a strain, species, or sub-species of a microorganism listed in Table 2 and one or more bacterial flavohemoglobins genes from a strain, species, or sub-species of a microorganism listed in Table 2. In some cases, the library is used in a method of producing a biomolecule comprising introducing a bacterial hemoglobin gene from the library into a host cell and culturing the host cell under conditions suitable for producing the biomolecule. In some cases, the biomolecule is a small molecule, an amino acid, a nucleotide, an organic acid, or an alcohol. In some cases, the amino acid is lysine, glutamic acid, tyrosine, phenylalanine, tryptophan, aspartic acid, asparagine, threonine, isoleucine, or methionine. In some cases, the organic acid is succinate, lactate or pyruvate. In some cases, the alcohol is ethanol or isobutanol. In some cases, the host cell belongs to the genus *Corynebacterium*. In some cases, the host cell is *Corynebacterium glutamicum*. In some cases, the introducing is performed by transformation, transduction or electroporation.

In a further aspect, provided herein is an isolated, synthetic or recombinant polynucleotide with a sequence comprising a codon optimized polynucleotide selected from SEQ ID NO: 12, SEQ ID NO: 10, SEQ ID NO: 11, SEQ ID NO: 9, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20, wherein the polynucleotide is codon optimized for expression in a host cell. In some cases, the host cell is *E. coli* and/or *C. glutamicum*.

BRIEF DESCRIPTION OF THE FIGURES

FIG. 3A illustrates the change in predicted productivity for each hemoglobin gene tested in each context (background). FIG. 3B illustrates the change in predicted yield for each hemoglobin gene tested in each context (background).

DETAILED DESCRIPTION

Definitions

Figure 1:
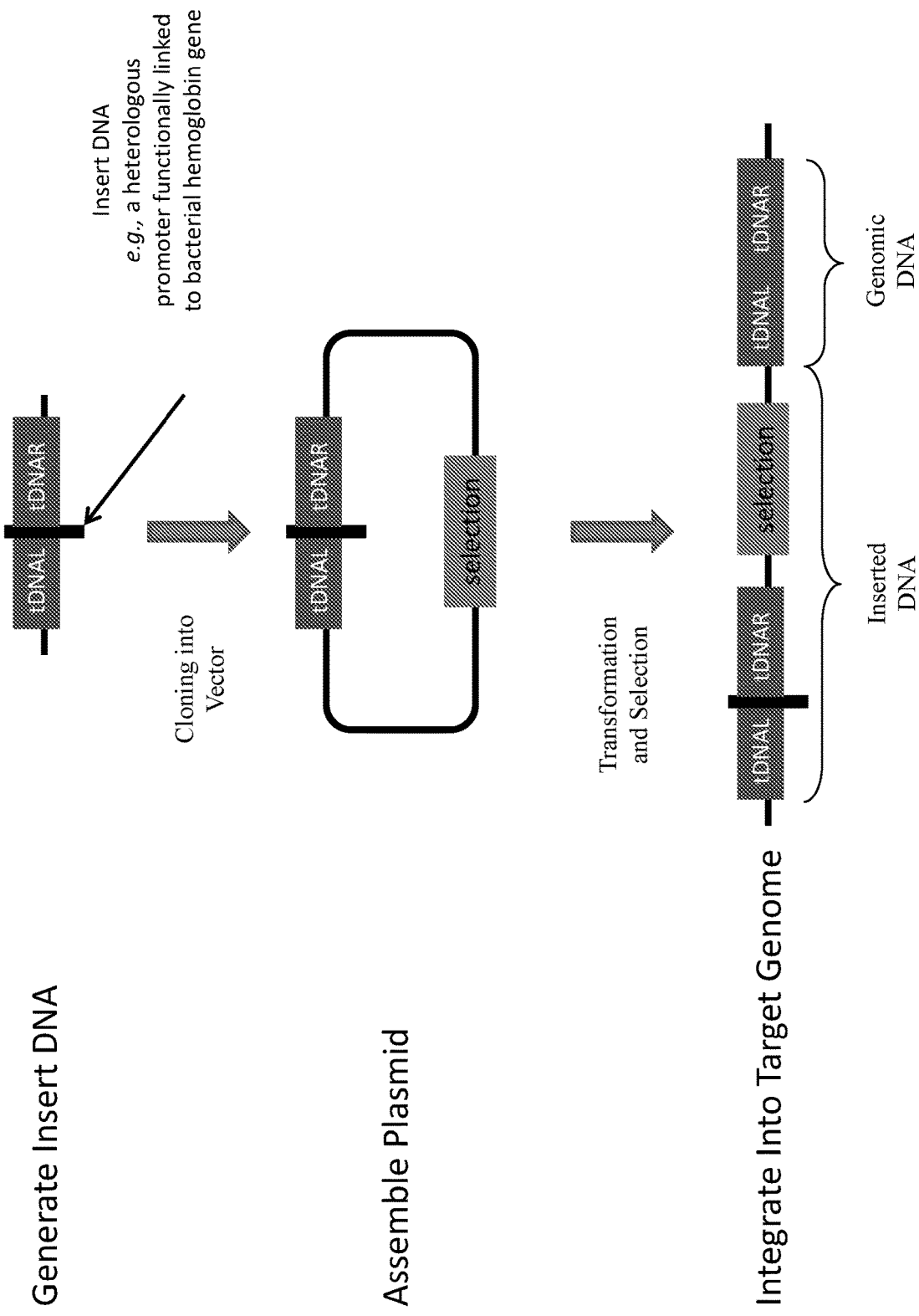
FIG. 1 illustrates assembly of transformation plasmids of the present disclosure, and their integration into host organisms. The insert sequence insert DNA is generated by combining one or more synthesized oligonucleotides in an assembly reaction. DNA inserts contain desired promoter sequence flanked by direct repeat region (i.e., homology arms) designed for looping out DNA in subsequent steps. Assembled plasmids contain the insert DNA (bacterial hemoglobin gene functionally linked to promoters provided herein), and optionally, one or more selection markers.

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Unless the context requires otherwise, throughout the present specification and claims, the word "comprise" and variations thereof, such as, "comprises" and "comprising" are to be construed in an open, inclusive sense that is as "including, but not limited to".

Reference throughout this specification to "one embodiment" or "an embodiment" means that a particular feature, structure or characteristic described in connection with the embodiment may be included in at least one embodiment of the present disclosure. Thus, the appearances of the phrases "in one embodiment" or "in an embodiment" in various places throughout this specification may not necessarily all referring to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

As used herein the terms "cellular organism" "microorganism" or "microbe" should be taken broadly. These terms can be used interchangeably and include, but may not be limited to, the two prokaryotic domains, Bacteria and Archaea, as well as certain eukaryotic fungi and protists. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in said tables or figures. The same characterization holds true for the recitation of these terms in other parts of the Specification, such as in the Examples.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) *thermophilus* (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) *Cyanobacteria*, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The terms "genetically modified microorganism," "recombinant microorganism," "recombinant host cell," and "recombinant strain" can be used interchangeably herein and can refer to microorganisms that have been genetically modified. Thus, the terms include a microorganism (e.g., bacteria, yeast cell, fungal cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring microorganism from which it was derived. It is understood that the terms refer not only to the particular recombinant microorganism in question, but also to the progeny or potential progeny of such a microorganism.

The term "wild-type microorganism" can describe a cell that occurs in nature, i.e. a cell that has not been genetically modified.

The term "genetically engineered" may refer to any manipulation of a microorganism's genome (e.g. by insertion or deletion of nucleic acids).

As used herein, the term "allele(s)" can mean any of one or more alternative forms of a gene, all of which alleles relate to at least one trait or characteristic. In a diploid cell, the two alleles of a given gene can occupy corresponding loci on a pair of homologous chromosomes. Since the present disclosure, in embodiments, relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype".

As used herein, the term "locus" (loci plural) can mean a specific place or places or a site on a chromosome where for example a gene or genetic marker is found.

As used herein, the term "genetically linked" can refer to two or more traits that are co-inherited at a high rate during breeding such that they are difficult to separate through crossing.

A "recombination" or "recombination event" as used herein can refer to a chromosomal crossing over or independent assortment. The term "recombinant" can refer to an organism having a new genetic makeup arising as a result of a recombination event.

As used herein, the term "phenotype" can refer to the observable characteristics of an individual cell, cell culture, organism, or group of organisms which results from the interaction between that individual's genetic makeup (i.e., genotype) and the environment.

As used herein, the term "chimeric" or "recombinant" when describing a nucleic acid sequence or a protein sequence can refer to a nucleic acid, or a protein sequence, that links at least two heterologous polynucleotides, or two heterologous polypeptides, into a single macromolecule, or that can re-arrange one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" can be a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" can refer to a polymeric form of nucleotides of any length, either ribonucleotides or deoxyribonucleotides, or analogs thereof. This term can refer to the primary structure of the molecule, and thus includes double- and single-stranded DNA, as well as double- and single-stranded RNA. It can also include modified nucleic acids such as methylated and/or capped nucleic acids, nucleic acids containing modified bases, backbone modifications, and the like. The terms "nucleic acid" and "nucleotide sequence" can be used interchangeably.

As used herein, the term "gene" can refer to any segment of DNA associated with a biological function. Thus, genes can include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and can refer to related sequences that share a common ancestor or family member and are determined based on the degree of sequence identity. The terms "homology," "homologous," "substantially similar" and "corresponding substantially" can be used interchangeably herein. They can refer to nucleic acid fragments wherein changes in one or more nucleotide bases do not affect the ability of the nucleic acid fragment to mediate gene expression or produce a certain phenotype. These terms can also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure can encompass more than the specific exemplary sequences. These terms can describe the relationship between a gene found in one species, subspecies, variety, cultivar or strain and the corresponding or equivalent gene in another species, subspecies, variety, cultivar or strain. For purposes of this disclosure homologous sequences can be compared. "Homologous sequences" or "homologues" or "orthologs" can be thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "nucleotide change" can refer to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" can refer to, e.g., amino acid substitution, amino acid modification, deletion, and/or insertion, as is well understood in the art.

As used herein, the term "at least a portion" or "fragment" of a nucleic acid or polypeptide can mean a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used can depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide can generally be longer than 4 amino acids.

Variant polynucleotides also encompass sequences that can be derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual (3$^{rd}$ ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR can include, but are not limited to, methods using paired primers, nested primers, single specific primers, degenerate primers, gene-specific primers, vector-specific primers, partially-mismatched primers, and the like.

The term "primer" as used herein can refer to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" can refer to hybridization conditions that affect the stability of hybrids, e.g., temperature, salt concentration, pH, formamide concentration and the like. These conditions can be empirically optimized to maximize specific binding and minimize non-specific binding of primer or probe to its target nucleic acid sequence. The terms as used can include reference to conditions under which a probe or primer will hybridize to its target sequence, to a detectably greater degree than other sequences (e.g. at least 2-fold over background). Stringent conditions can be sequence dependent and will be different in different circumstances. Longer sequences can hybridize specifically at higher temperatures. Generally, stringent conditions can be selected to be about 5° C. lower than the thermal melting point (Tm) for the specific sequence at a defined ionic strength and pH. The Tm can be the temperature (under defined ionic strength and pH) at which 50% of a complementary target sequence hybridizes to a perfectly matched probe or primer. Typically, stringent conditions may be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" can include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001. In some embodiments, stringent conditions are hybridization in 0.25 M Na2HPO4 buffer (pH 7.2) containing 1 mM Na2EDTA, 0.5-20% sodium dodecyl sulfate at 45° C., such as 0.5%, 1%, 2%, 3%, 4%, 5%, 6%, 7%, 8%, 9%, 10%, 11%, 12%, 13%, 14%, 15%, 16%, 17%, 18%, 19% or 20%, followed by a wash in 5×SSC, containing 0.1% (w/v) sodium dodecyl sulfate, at 55° C. to 65° C.

As used herein, "promoter" or "promoter polynucleotide" can refer to a DNA sequence capable of controlling the expression of a coding sequence or functional RNA. The promoter sequence consists of proximal and more distal upstream elements, the latter elements can often be referred to as enhancers. Accordingly, an "enhancer" can be a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, the phrases "recombinant construct", "expression construct", "chimeric construct", "construct", and "recombinant DNA construct" can be used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. In some cases, a chimeric construct can be a recombinant construct comprising a regulatory sequence (e.g., promoter) and a coding sequence (e.g., prokaryotic hemoglobin gene). Each coding sequence in a chimeric construct comprising a plurality of coding sequences can be controlled by or functionally linked to a separate regulatory sequence). Such constructs described herein may be used by itself or may be used in conjunction with a vector. If a vector is used then the choice of vector can be dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218: 78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" or "functionally linked" can mean in this context the sequential arrangement of the promoter polynucleotide according to the disclosure with a further oligo- or polynucleotide (e.g., prokaryotic hemoglobin gene), resulting in transcription of said further polynucleotide (e.g., prokaryotic hemoglobin gene). In other words, "operably linked" or "functionally linked" can mean the promoter controls the transcription of the gene (e.g. prokaryotic hemoglobin gene) adjacent or downstream or 3' to said promoter.

The term "carbon source" generally can refer to a substance suitable to be used as a source of carbon for cell growth. Carbon sources can include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These can include, for example, various monosaccharides such as glucose, xylose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "feedstock" can be defined as a raw material or mixture of raw materials supplied to a microorganism or fermentation process from which other products can be made. For example, a carbon source, such as biomass or the carbon compounds derived from biomass can be a feedstock for a microorganism that produces a product of interest (e.g. small molecule, peptide, synthetic compound, fuel, alcohol, etc.) in a fermentation process. However, a feedstock may contain nutrients other than a carbon source.

The term "volumetric productivity" or "production rate" can be defined as the amount of product formed per volume of medium per unit of time. Volumetric productivity can be reported in gram per liter per hour (g/L/h).

The term "specific productivity" can defined as the rate of formation of the product. To describe productivity as an inherent parameter of the microorganism and not of the fermentation process, productivity can herein further be defined as the specific productivity in gram product per gram of cell dry weight (CDW) per hour (g/g CDW/h). Using the relation of CDW to $OD_{600}$ for the given microorganism specific productivity can also be expressed as gram product per liter culture medium per optical density of the culture broth at 600 nm (OD) per hour (g/L/h/OD)

The term "yield" can be defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product.

The term "titre" or "titer" can be defined as the strength of a solution or the concentration of a substance in solution. For example, the titre of a product of interest (e.g. small molecule, peptide, synthetic compound, fuel, alcohol, etc.) in a fermentation broth can be described as g of product of interest in solution per liter of fermentation broth (g/L).

The term "total titer" can be defined as the sum of all product of interest produced in a process, including but not limited to the product of interest in solution, the product of interest in gas phase if applicable, and any product of interest removed from the process and recovered relative to the initial volume in the process or the operating volume in the process.

As used herein, the term "prokaryotic hemoglobin" can refer to any protein derived from a prokaryotic cell (i.e., Bacteria or Archaea) that is a heme-containing oxygen binding and/or transporting protein containing one or more globin domains. Prokaryotic hemoglobin can refer to a hemoglobin protein as described herein or a related protein such as, for example, flavohemoglobin. The prokaryotic hemoglobin protein can be from any genus and/or species of bacteria or Archaea known in the art. The term "bacterial hemoglobin" as used herein can refer to a hemoglobin protein as described herein derived from a bacteria.

As used herein, the term "prokaryotic hemoglobin gene" can refer to any nucleic acid (e.g., genomic DNA, cDNA and/or mRNA) that when transcribed and/or translated encodes a prokaryotic hemoglobin protein as described herein. The term "bacterial hemoglobin gene" as used herein can refer to a bacterial hemoglobin protein as described herein derived from a bacteria.

The term "product of interest" or "biomolecule" as used herein refers to any product produced by microbes from feedstock. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a microbe, such as: a microbial enzyme, including: catalase, amylase, protease, pectinase, glucose isomerase, cellulase, hemicellulase, lipase, lactase, streptokinase, and many others. The intracellular component may also include recombinant proteins, such as: insulin, hepatitis B vaccine, interferon, granulocyte colony-stimulating factor, streptokinase and others.

Overview

Given the enormous amount of products derived from metabolic processes in modern industrial microbes, it comes as no surprise that engineers are under tremendous pressure to improve the speed and efficiency by which a given microorganism is able to produce a target product. Accordingly, metabolic engineering approaches seek genetic strategies, for example to alleviate adverse effects of oxygen limitation on microorganisms. In one approach, the *Vitreo-*

*scilla* hemoglobin gene (vhb) was successfully transferred to *Escherichia coli* and upon expression of VHb, growth and protein production of *E. coli* was enhanced under microaerobic conditions (see Khosla C., Bailey J. E. (1988) Heterologous expression of a bacterial haemoglobin improves the growth properties of recombinant *E. coli*. Nature 331, 633-635 and Khosla C., Curtis J. E., DeModena J., Rinas U., Bailey J. E. (1990) Expression of intracellular hemoglobin improves protein synthesis in oxygen-limited *E. coli*. Bio-Technology 8, 849-853). Further, this approach has produced positive effects such as promoting either the efficiency of oxygen-limited growth and/or production of primary and secondary metabolites in numerous microorganisms as shown in Frey A D et al. (2003) Bacterial hemoglobins and flavohemoglobins: versatile proteins and their impact on microbiology and biotechnology FEMS Microbiol Rev. October 27(4), 525-545. However, the biochemical properties of Vhb may not be optimized for all foreign host cells and determining which hemoglobin gene will produce positive effects in a specific host microorganism using traditional microbial genomic engineering methods can be laborious and/or cost prohibitive.

The present disclosure provides a microbial genomic engineering method that does not suffer from the myriad of problems associated with traditional microbial strain improvement programs.

One aspect provided herein is a method for generating a microorganism (e.g., bacteria) that is capable of increased production of a biomolecule or product of interest. In general, the methods for generating a microorganism for use in producing any biomolecule as provided herein can entail genetically modifying a host microorganism by introducing a member of a library of target genes into said host microorganism to generate a genomically engineered strain of said microorganism, culturing said engineered strain under conditions suitable to produce the biomolecule or product of interest, and selecting said engineered strain if said engineered strain produces an increased amount of the biomolecule or product of interest. The increased amount can be as compared to a wild-type strain of the host microorganism. The increased amount can be as compared to a strain of the host microorganism that does not contain a member of the library of target genes. The library of target genes can comprise a plurality of vectors, wherein each vector in the library comprises a chimeric construct comprising at least one promoter polynucleotide functionally linked or coupled to a target gene.

An exemplary workflow of one of the embodiments of the disclosure entails selecting a target gene, acquiring or synthesizing nucleic acid (e.g., DNA) for the target gene, and cloning said acquired or synthesized target gene into a suitable vector. Any method known in the art and/or provided herein can be used to assemble or clone the target gene or target genes into a suitable vector. The vector can be any vector known in the art and/or provided herein that is compatible with the host microorganism to be utilized. Once the vector comprising the target gene(s) is assembled, it can be introduced into the host microorganism. The introduction of the vector can be using any method known in the art and/or provided herein. The host microorganism can be any host microorganism provided herein. Once introduced into the host microorganism, genetically modified hosts can be selected and the insertion of the target gene(s) can be evaluated. The target gene(s) can be engineered to be inserted into specific locations of the host microorganism's genome. In some cases, the target gene(s) is inserted into a neutral site of the genome that facilitates expression of the target gene(s) without perturbing unintended pathways/processes within the host microorganism. In some cases, the target gene(s) replace specific gene(s) within the host microorganism. The specific gene can be the homologous target gene normally present in the host microorganism. The integration site, such as, for example, the neutral integration site can be determined empirically such that various sites can tested and a site that permits expression of the integrated target gene(s) without being detrimental to the host cell can be chosen. Integration into a desired site (e.g., neutral site) can be facilitated by cloning the target gene(s) into a vector comprising portions of sequence homologous to the desired integration site (i.e., homologous arms) and subsequently performing a recombination event in the host cell. The target gene(s) can be inserted between the portions of homologous sequence. In one embodiment, the vector comprises about 2 kb of sequence homologous to the desired integration site. The sequence homologous to the desired site can flank a prokaryotic hemoglobin gene insert such that a first portion of the sequence is upstream (i.e., 5') of the gene insert and a second portion of the sequence is downstream (i.e., 3') of the gene insert. In another embodiment, the vector comprises about 4 kb of sequence homologous to the desired integration site. In this embodiment, the vector comprises about 2 kb of sequence homologous to the desired integration site upstream (i.e., 5') to a prokaryotic hemoglobin gene insert and about 2 kb of sequence homologous to the desired integration site downstream (i.e., 3') to a prokaryotic hemoglobin gene insert. In one embodiment, integration is performed by a single-cross-over integration and subsequent loop out of the plasmid backbone facilitated by counter-selection on a marker present in the vector backbone. In one embodiment, the target gene is any prokaryotic hemoglobin gene known in the art and/or provided herein.

Evaluation of the insertion can be performed using any method know in the art such as, for example, amplifying and/or sequencing of the genetically modified microorganism's genome or portions thereof. In some cases, the methods provided herein also entail the removal or looping out of selection markers through counter selection as described herein. The looping out can be performed using any of the methods provided herein.

Following the evaluation of the insertion of the target gene(s) and, optional, removal of selection markers, the genetically modified strain can be evaluated for its ability to produce a biomolecule or product of interest. Prior to evaluation an optional step can be expanding the strain. Expansion can entail culturing the genetically modified strain on plates or in wells in a multi-well plate in growth media suitable for expansion. The evaluation step can entail culturing the genetically modified strain on plates or in wells in a multi-well plate comprising growth media/conditions designed to mimic actual conditions for producing a biomolecule or product of interest. In some cases, the growth media in this step is suitable for the production of biomolecules or products of interest derived from the metabolic processing of glucose. If the genetically modified strain possesses or is predicted to produce a desired or threshold rate of production or yield of the biomolecule or product of interest as determined from the evaluation step, the strain can be selected and placed in cold storage. The prediction can be based on measuring the amount of product of interest and biomass formed at various time points during culturing of the strain and using said measurements to predict how said strain will perform under expanded or larger scale conditions (e.g., fermentation conditions). In one embodiment, the prediction is based on a linear regression analysis of the performance of the strain during the evaluation method.

In some cases, a genetically modified strain possessing or predicted to produce a desired or threshold rate of production or yield of the biomolecule or product of interest is transferred to or grown in a larger culture under conditions for producing the biomolecule or product of interest (e.g., fermentation conditions). This step can be used in order to determine if the selected strain can perform as predicted under actual conditions for the production of the biomolecule or product of interest. In some cases, the steps provided herein for the introduction and evaluation of each target gene from a library of target genes such as those provided herein are repeated for each target gene from the library in order to select one or more strains of genetically modified microorganisms that produce a desired or threshold yield and/or productivity rate of a biomolecule or product of interest.

In one embodiment, the biomolecule or product of interest is derived from a microorganism grown in an oxygen poor environment such that the methods provided herein entail the generation of a strain or strains of microorganisms possessing an increased partial pressure of oxygen within the microorganism thereby permitting the microorganism to produce an increased amount of a biomolecule or product of interest when grown in said oxygen poor environment. In one embodiment, the methods provided herein entail the introduction of one or more target genes involved in oxygen binding and/or transport. In one embodiment, the target gene is a prokaryotic hemoglobin gene such that a prokaryotic hemoglobin gene is introduced into the host microorganism in the methods provided herein. The prokaryotic hemoglobin gene can be a heterologous gene in the host microorganism. In one embodiment, the introduction of a prokaryotic hemoglobin gene into the host microorganism produces a system for increasing the level or partial pressure of oxygen within the host microorganism. The increased level or partial pressure can be vs. a wild-type strain of said microorganism or a microorganism that does not express said heterologous prokaryotic hemoglobin gene. The biomolecules or products of interest produced by the methods provided herein can be any commercial product produced from microbes. In some cases, the biomolecule or product of interest is produced by fermentation. In some cases, the biomolecule or product of interest is a pharmaceutical, a small molecule, an amino acid, a nucleotide, an organic acid, or an alcohol. The amino acid can be glutamic acid, tyrosine, phenylalanine, tryptophan, aspartic acid, asparagine, threonine, isoleucine, methionine, or lysine. The organic acid can be succinate, lactate or pyruvate. The alcohol can be ethanol or isobutanol.

In one embodiment, the disclosed microbial genomic engineering method utilizes a library of bacterial hemoglobin genes. A bacterial hemoglobin gene can be selected based on the hemoglobins affinity for binding and/or transport of oxygen into a cell. Following engineering, the microbes can be efficiently screened or evaluated for resultant outcome, e.g. growth rate and/or production of a product as provided herein. This process of utilizing the libraries provided herein to define particular genomic alterations and then testing/screening host microbial genomes harboring the alterations can be implemented in an efficient and iterative manner and can be used to identify specific bacterial hemoglobin genes whose expression in a host cell produces a desired or threshold level of growth or production of a biomolecule or product of interest.

In one embodiment, each prokaryotic hemoglobin gene (e.g., bacterial hemoglobin gene) as provided herein for use in the methods provided herein is under the control of or functionally linked to a native promoter or any of the promoter polynucleotides provided herein. A "promoter polynucleotide" or a "promoter" or a "polynucleotide having promoter activity" can mean a polynucleotide, preferably deoxyribopolynucleotide, or a nucleic acid, preferably deoxyribonucleic acid (DNA), which when functionally linked to a polynucleotide to be transcribed determines the point and frequency of initiation of transcription of the coding polynucleotide (e.g., prokaryotic hemoglobin or bacterial hemoglobin gene), thereby enabling the strength of expression of the controlled polynucleotide to be influenced. In one embodiment, each prokaryotic hemoglobin gene (e.g., bacterial hemoglobin gene) in a library comprising prokaryotic hemoglobin genes (e.g., bacterial hemoglobin genes) is under the control of the same or an identical promoter. In one embodiment, each prokaryotic hemoglobin gene (e.g., bacterial hemoglobin gene) in a library comprising prokaryotic hemoglobin genes (e.g., bacterial hemoglobin genes) is under the control of separate or different promoter.

In one embodiment, provided herein is a promoter ladder for use in generating a library of prokaryotic hemoglobin genes (e.g., bacterial hemoglobin genes). The term "promoter ladder" as used herein refers to a plurality of promoters with incrementally increasing levels of promoter activity. The term "promoter activity" as used herein refers to the ability of the promoter to initiate transcription of a polynucleotide sequence into mRNA. Methods of assessing promoter activity are well known to those of skill in the art and can include, for example the methods described in Example 2 of U.S. 62/264,232, filed Dec. 7, 2015, and PCT/US16/65464 (PCT Publication No. WO2017/100376), each of which is herein incorporated by references in its entirety. The term "constitutive promoter" as used herein can refer to a promoter that directs the transcription of its associated genes at a constant rate regardless of the internal or external cellular conditions.

Promoters

In some embodiments, the present disclosure teaches methods of selecting promoters with optimal expression properties to modulate RNA degradation function and produce beneficial effects on overall-host strain productivity.

Promoters regulate the rate at which genes are transcribed and can influence transcription in a variety of ways. Constitutive promoters, for example, direct the transcription of their associated genes at a constant rate regardless of the internal or external cellular conditions, while regulatable promoters increase or decrease the rate at which a gene is transcribed depending on the internal and/or the external cellular conditions, e.g. growth rate, temperature, responses to specific environmental chemicals, and the like. Promoters can be isolated from their normal cellular contexts and engineered to regulate the expression of virtually any gene, enabling the effective modification of cellular growth, product yield and/or other phenotypes of interest.

In some embodiments, the present disclosure teaches methods of identifying one or more promoters and/or generating variants of one or more promoters within a host cell, which exhibit a range of expression strengths (e.g. promoter ladders discussed infra), or superior regulatory properties (i.e., tighter regulatory control for selected genes). A particular combination of these identified and/or generated promoters can be grouped together as a promoter ladder for use in the RNA degradation perturbation experiments explained in more detail below.

In some embodiments, promoter ladders are created by identifying natural, native, or wild-type promoters associated with a target gene of interest that have a range of expression strengths. These identified promoters can be grouped together as a promoter ladder.

In some embodiments, promoter ladders are created by: identifying natural, native, or wild-type promoters associated with a target gene of interest and then mutating said promoter to derive multiple mutated promoter sequences. Each of these mutated promoters is tested for effect on target gene expression. In some embodiments, the edited promoters are tested for expression activity across a variety of conditions, such that each promoter variant's activity is documented/characterized/annotated and stored in a database. The resulting edited promoter variants are subsequently organized into promoter ladders arranged based on the strength of their expression (e.g., with highly expressing variants near the top, and attenuated expression near the bottom, therefore leading to the term "ladder").

In some embodiments, the present disclosure teaches promoter ladders that are a combination of identified naturally occurring promoters and mutated variant promoters.

In some embodiments, the present disclosure teaches methods of identifying natural, native, or wild-type promoters that satisfied both of the following criteria: 1) represented a ladder of constitutive promoters; and 2) could be encoded by short DNA sequences, ideally less than 100 base pairs. In some embodiments, constitutive promoters of the present disclosure exhibit constant gene expression across two selected growth conditions (typically compared among conditions experienced during industrial cultivation). In some embodiments, the promoters of the present disclosure will consist of a ~60 base pair core promoter, and a 5' UTR between 26- and 40 base pairs in length.

In some embodiments, one or more of the aforementioned identified naturally occurring promoter sequences are chosen for gene editing. In some embodiments, the natural promoters are edited via any known genetic mutation methods. In other embodiments, the promoters of the present disclosure are edited by synthesizing new promoter variants with the desired sequence.

The entire disclosures of U.S. Patent Application No. 62/264,232, filed on Dec. 7, 2015, and PCT/US16/65464 (PCT Publication No. WO2017/100376), filed on Dec. 7, 2016, are each hereby incorporated by reference in its entirety for all purposes.

A non-exhaustive list of the promoters of the present disclosure is provided in Table 1 below. Each of the promoter sequences in Table 1 can be referred to as a heterologous promoter or heterologous promoter polynucleotide.

TABLE 1

Selected promoter sequences of the present disclosure.

| SEQ ID No. | Promoter Short Name |
|---|---|
| 1 | P1 |
| 2 | P2 |
| 3 | P3 |
| 4 | P4 |
| 5 | P5 |
| 6 | P6 |
| 7 | P7 |
| 8 | P8 |

In some embodiments, the promoters of the present disclosure exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a promoter sequences from Table 1.

Prokaryotic Hemoglobin Genes

Provided herein is a library of prokaryotic hemoglobin genes for use in the methods provided herein. The library of prokaryotic hemoglobin genes can comprise one or more prokaryotic hemoglobin genes. Each prokaryotic hemoglobin gene in the library can be a native form of the prokaryotic hemoglobin gene or a mutated form. The mutated form can comprise one or more mutations selected from an insertion, deletion, single nucleotide polymorphism (SNP), or translocation. Each prokaryotic hemoglobin gene in the library can be a bacterial hemoglobin gene. The bacterial hemoglobin gene can be any bacterial hemoglobin gene known in the art. Bacterial hemoglobin genes can be selected for generation of a bacterial hemoglobin library based on their characteristics as reported in the literature such as, for example, WO1992003546 and U.S. Pat. No. 6,759,218, each of which is hereby incorporated by reference in its entirety. The host cell can be any host cell provided herein. In one embodiment, the library of prokaryotic hemoglobin genes comprises prokaryotic hemoglobin genes from any strain/species/sub-species of *Aeromonas, Aquifex, Candidatus, Campylobacter, Clostridium, Novosphingobium, Rhodopseudomonas, Vitreoscilla, Bacillus, Corynebacterium, Azotobacter, Gordonia, Hassallia, Hurkholderia, Deinococcus, Erwinia, Escherchia, Fischerella, Magnetospirillum, Nostoc, Oceanobacillus, Phaeobacter, Pseudomonas, Ralstonia, Salmonella, Sandaracinus, Shewanella, Shigella, Sinorhizobium, Spirosoma, Staphylococcus, Streptomyces, Sulfurimonas, Thermobifida, Vibrio, Xylella, Yersinia* or a combination thereof. In one embodiment, the library of prokaryotic hemoglobin genes comprises one or more prokaryotic hemoglobin genes selected from an organism listed in Table 2 or a combination thereof. A hemoglobin gene from an organism listed in Table 2 for inclusion in a library of hemoglobin genes as provided herein can be codon optimized as described herein for expression in a host cell as provided herein.

TABLE 2

Organisms containing Bacterial Hemoglobin (Hb) and flavohemoglobin (flavoHB) genes.

| Organism | Gene Type |
|---|---|
| *Aeromonas molluscorum* | Hemoglobin |
| *Aquifex aeolicus* | Hemoglobin |
| *Campylobacter jejuni* HCTC11168 | Hemoglobin |
| *Clostridium perfringens* hyp27 | Hemoglobin |
| *Corynebacterium glutamicum* | Hemoglobin |
| *Novosphingobium aromaticivorans* | Hemoglobin |
| *Rhodopseudomonas palustris* | Hemoglobin |
| *Gordonia* terrae C-6 | Hemoglobin |
| *Vitreoscilla stercoraria* | Hemoglobin |
| *Spirosoma radiotolerans* | Hemoglobin |
| *Shewanella loihica* (strain ATCC BAA-1088/PV-4) | Hemoglobin |
| *Sulfurimonas gotlandica* (strain DSM 19862/JCM 16533/GD1) | Hemoglobin |
| *Sandaracinus amylolyticus* | Hemoglobin |
| *Fischerella* sp. JSC-11 | Hemoglobin |
| *Candidatus Entotheonella* sp. TSY1 | Hemoglobin |
| *Hassallia byssoidea* VB512170 | Hemoglobin |
| *Phaeobacter gallaeciensis* DSM 26640 | Hemoglobin |
| *Azotobacter vinelandii* | Flavohemoglobin |
| *Bacillus anthracis* A2012 | Flavohemoglobin |

TABLE 2-continued

Organisms containing Bacterial Hemoglobin
(Hb) and flavohemoglobin (flavoHB) genes.

| Organism | Gene Type |
|---|---|
| *Bacillus halodurans* C-125 | Flavohemoglobin |
| *Bacillus subtilis* 168trpC2 | Flavohemoglobin |
| *Burkholderia fungorum* | Flavohemoglobin |
| *Burkholderia* sp. TH2 | Flavohemoglobin |
| *Corynebacterium glutamicum* ATCC 13032 | Flavohemoglobin |
| *Deinococcus radiodurans* | Flavohemoglobin |
| *Erwinia chrysanthemi* | Flavohemoglobin |
| *Escherichia coli* MG1655 | Flavohemoglobin |
| *Magnetospirillum magnetotacticum* | Flavohemoglobin |
| *Nostoc punctiforme* | Flavohemoglobin |
| *Oceanobacillus iheyensis* | Flavohemoglobin |
| *Pseudomonas fluorescens* | Flavohemoglobin |
| *Pseudomonas aeruginosa* PAO1 | Flavohemoglobin |
| *Ralstonia eutropha* | Flavohemoglobin |
| *Ralstonia metallidurans* | Flavohemoglobin |
| *Ralstonia solanacearum* | Flavohemoglobin |
| *Salmonella enterica* serovar *Typhi* | Flavohemoglobin |
| *Salmonella enterica* serovar *Typhimurium* | Flavohemoglobin |
| *Shigella flexneri* 2a str. 301 | Flavohemoglobin |
| *Sinorhizobium meliloti* | Flavohemoglobin |
| *Staphylococcus aureus* N315 | Flavohemoglobin |
| *Staphylococcus aureus* subsp. *aureus* MW2 | Flavohemoglobin |
| *Staphylococcus. aureus* MU50 | Flavohemoglobin |
| *Streptomyces coelicolor* A3 | Flavohemoglobin |
| *Streptomyces coelicolor* A3 | Flavohemoglobin |
| *Streptomyces coelicolor* A3 cosmid J11 | Flavohemoglobin |
| *Thermobifida fusca* | Flavohemoglobin |
| *Vibrio cholerae* | Flavohemoglobin |
| *Vibrio parahämolyticus* | Flavohemoglobin |
| *Xylella fastidiosa* 9a5c | Flavohemoglobin |
| *Yersinia pestis* OC92 | Flavohemoglobin |

In one embodiment, the library of prokaryotic hemoglobin genes comprises one or more bacterial hemoglobin genes selected from SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 or a combination thereof.

In some embodiments, the hemoglobin genes of the present disclosure exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a hemoglobin gene provided herein.

In one embodiment, the library of prokaryotic hemoglobin genes comprises prokaryotic hemoglobin genes that encode polypeptide sequences selected from SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 or a combination thereof.

In some embodiments, the hemoglobin polypeptides encoded by the hemoglobin genes of the present disclosure exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a hemoglobin polypeptide provided herein.

Each prokaryotic hemoglobin gene in the library can be functionally linked or under the control of its native promoter or a mutated form of its native promoter. Each prokaryotic hemoglobin gene in the library can be functionally linked to or controlled by any promoter provided herein. Each prokaryotic hemoglobin gene in the library can be controlled by a promoter polynucleotide sequence that comprises a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. Each prokaryotic hemoglobin gene in the library can be controlled by a promoter polynucleotide sequence that contains a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In one embodiment, each prokaryotic hemoglobin gene in the library is present as a set of prokaryotic hemoglobin genes, wherein each set has one prokaryotic hemoglobin gene functionally linked to SEQ ID NO: 1, one prokaryotic hemoglobin gene functionally linked to SEQ ID NO: 2, one prokaryotic hemoglobin gene functionally linked to SEQ ID NO: 3, one prokaryotic hemoglobin gene functionally linked to SEQ ID NO: 4, one prokaryotic hemoglobin gene functionally linked to SEQ ID NO: 5, one prokaryotic hemoglobin gene functionally linked to SEQ ID NO: 6, one prokaryotic hemoglobin gene functionally linked to SEQ ID NO: 7 and one prokaryotic hemoglobin gene functionally linked to SEQ ID NO: 8 or a combination thereof. Each prokaryotic hemoglobin gene in a library of prokaryotic hemoglobin genes can be present in a chimeric construct such that the gene can be flanked by one or more regulatory sequences and/or sequence homologous to sequence present in the genome of a host cell. The sequence homologous to sequence present in the host cell can facilitate integration of the prokaryotic hemoglobin gene into a site or locus of the host cell genome that comprises complementary sequence. Integration can be via a recombination event. The regulatory sequence can be any regulatory sequence known in the art or provided herein such as, for example, a promoter, start, stop, signal, secretion and/or termination sequence used by the genetic machinery of the host cell. The termination sequence can be selected from SEQ ID NO: 21 or SEQ ID NO: 22.

In one embodiment, a candidate prokaryotic hemoglobin is selected for inclusion in the libraries or methods provided herein based on its similarity to one or more prokaryotic hemoglobins known in the art. The similarity can be determined using algorithms known in the art for performing sequence alignments between nucleic acid or protein sequences such as, for example, BLAST algorithms. For example, the amino acid sequence of the hemoglobin from *Vitreoscilla stercocaria* can be used to seed a TREMBL protein database search using the BLAST algorithm. All candidate hemoglobins that are within a certain similarity to the seeded hemoglobin (e.g., amino acid sequence of the hemoglobin from *Vitreoscilla stercocaria*) can be selected. The certain similarity can be a threshold such that candidate hemoglobins that generally align with the hemoglobin used as a seed (e.g., the amino acid sequence of the hemoglobin from *Vitreoscilla stercocaria*) are selected. In some cases, the BLAST algorithm is used and the candidate hemoglobins that generally align with the seed hemoglobin (e.g., the amino acid sequence of the hemoglobin from *Vitreoscilla stercocaria*) are those with a BLAST E-value of 5. Subsequently, pairwise alignment between each selected candidate sequence in the set can be conducted to generate a similarity score associating each sequence with any other sequence in the set. Pairwise alignment can be done using any pairwise alignment tool known in the art such as, for example, the online tool available at http://efi.igb.illinois.edu/efi-est/. Selected candidates can be sub-grouped into sets of more or less similar candidate sequences. Sub-grouping can be performed using a clustering algorithm such as, for example, the software tool Cytoscape (cytoscape.org). Representative candidates from each subgroup can then be selected so as to maximize the diversity of the sequences that can be present in the library. Each selected candidate hemoglobin can have its corresponding nucleic acid sequence codon optimized as described herein for subsequent inclusion in a library of hemoglobin genes as provided herein.

Generating Mutated Forms of Prokaryotic Hemoglobin Genes

As provided herein, a prokaryotic hemoglobin gene for use in the methods provided herein can be a mutated form of the gene from which it is derived. The mutated gene can be mutated in any way known in the art or provided herein.

In some embodiments, the present disclosure teaches mutating cell populations by introducing, deleting, or replacing selected portions of genomic DNA. Thus, in some embodiments, the present disclosure teaches methods for targeting mutations to a specific locus (e.g., prokaryotic hemoglobin gene). In other embodiments, the present disclosure teaches the use of gene editing technologies such as ZFNs, TALENS, or CRISPR, to selectively edit target DNA regions. Following mutation of the cell populations, the targeted mutations can be isolated from the cells and subsequently used for generating a library of prokaryotic hemoglobin gene as described herein.

In some embodiments, the present disclosure teaches mutating selected DNA regions (e.g., prokaryotic hemoglobin genes) outside of the host organism. For example, in some embodiments, the present disclosure teaches mutating native prokaryotic hemoglobin genes.

In some embodiments, the selected regions of DNA are produced in vitro via gene shuffling of natural variants, or shuffling with synthetic oligos, plasmid-plasmid recombination, virus plasmid recombination, or virus-virus recombination. In other embodiments, the genomic regions are produced via error-prone PCR or site-directed mutagenesis.

In some embodiments, generating mutations in selected genetic regions containing a prokaryotic hemoglobin gene is accomplished by "reassembly PCR." Briefly, oligonucleotide primers (oligos) are synthesized for PCR amplification of segments of a nucleic acid sequence of interest (e.g., prokaryotic hemoglobin gene), such that the sequences of the oligonucleotides overlap the junctions of two segments. The overlap region is typically about 10 to 100 nucleotides in length. Each of the segments is amplified with a set of such primers. The PCR products are then "reassembled" according to assembly protocols. In brief, in an assembly protocol, the PCR products are first purified away from the primers, by, for example, gel electrophoresis or size exclusion chromatography. Purified products are mixed together and subjected to about 1-10 cycles of denaturing, reannealing, and extension in the presence of polymerase and deoxynucleoside triphosphates (dNTP's) and appropriate buffer salts in the absence of additional primers ("self-priming"). Subsequent PCR with primers flanking the gene are used to amplify the yield of the fully reassembled and shuffled genes.

In some embodiments of the disclosure, mutated hemoglobin DNA regions, such as those discussed above, are enriched for mutant sequences so that the multiple mutant spectrum, i.e. possible combinations of mutations, is more efficiently sampled. In some embodiments, mutated sequences are identified via a mutS protein affinity matrix (Wagner et al., Nucleic Acids Res. 23(19):3944-3948 (1995); Su et al., Proc. Natl. Acad. Sci. (U.S.A.), 83:5057-5061 (1986)) with a preferred step of amplifying the affinity-purified material in vitro prior to an assembly reaction. This amplified material is then put into an assembly or reassembly PCR reaction.

Generation of Libraries Comprising Prokaryotic Hemoglobin Genes

In some embodiments, the present disclosure teaches inserting and/or replacing and/or deleting a DNA segment comprising a prokaryotic hemoglobin gene of the host organism. In some aspects, the methods taught herein involve building an oligonucleotide of interest (i.e. a prokaryotic hemoglobin segment), which can be incorporated into the genome of a host organism. In some embodiments, the prokaryotic hemoglobin DNA segments of the present disclosure can be obtained via any method known in the art, including, copying or cutting from a known template, mutation, or DNA synthesis. In some embodiments, the present disclosure is compatible with commercially available gene synthesis products for producing DNA sequences (e.g., GeneArt™ GeneMaker™, GenScript™, Anagen™, Blue Heron™, Entelechon™, GeNOsys, Inc., or Qiagen™).

In some embodiments, the prokaryotic hemoglobin DNA segment is designed to incorporate the prokaryotic hemoglobin DNA segment into a selected DNA region of the host organism. The selected DNA region can be a neutral integration site. In other embodiments, the prokaryotic hemoglobin DNA segment is designed to remove the native prokaryotic hemoglobin gene from the DNA of the host organisms.

In some embodiments, the prokaryotic hemoglobin gene used in the inventive methods can be synthesized in stages as oligonucleotides using any of the methods of enzymatic or chemical synthesis known in the art. The oligonucleotides may be synthesized on solid supports such as controlled pore glass (CPG), polystyrene beads, or membranes composed of thermoplastic polymers that may contain CPG. Oligonucleotides can also be synthesized on arrays, on a parallel microscale using microfluidics (Tian et al., Mol. BioSyst., 5, 714-722 (2009)), or known technologies that offer combinations of both (see Jacobsen et al., U.S. Pat. App. No. 2011/0172127).

Synthesis on arrays or through microfluidics offers an advantage over conventional solid support synthesis by reducing costs through lower reagent use. The scale required for gene synthesis is low, so the scale of oligonucleotide product synthesized from arrays or through microfluidics is acceptable. However, the synthesized oligonucleotides are of lesser quality than when using solid support synthesis (See Tian infra.; see also Staehler et al., U.S. Pat. App. No. 2010/0216648).

A great number of advances have been achieved in the traditional four-step phosphoramidite chemistry since it was first described in the 1980's (see for example, Sierzchala, et al. *J. Am. Chem. Soc.*, 125, 13427-13441 (2003) using peroxy anion deprotection; Hayakawa et al., U.S. Pat. No. 6,040,439 for alternative protecting groups; Azhayev et al, *Tetrahedron* 57, 4977-4986 (2001) for universal supports; Kozlov et al., *Nucleosides, Nucleotides, and Nucleic Acids,* 24 (5-7), 1037-1041 (2005) for improved synthesis of longer oligonucleotides through the use of large-pore CPG; and Damha et al., *NAR,* 18, 3813-3821 (1990) for improved derivatization).

Regardless of the type of synthesis, the resulting oligonucleotides may then form the smaller building blocks for longer polynucleotides (i.e., prokaryotic hemoglobin gene). In some embodiments, smaller oligonucleotides can be joined together using protocols known in the art, such as polymerase chain assembly (PCA), ligase chain reaction (LCR), and thermodynamically balanced inside-out synthesis (TBIO) (see Czar et al. Trends in Biotechnology, 27, 63-71 (2009)). In PCA, oligonucleotides spanning the entire length of the desired longer product are annealed and extended in multiple cycles (typically about 55 cycles) to eventually achieve full-length product. LCR uses ligase enzyme to join two oligonucleotides that are both annealed to a third oligonucleotide. TBIO synthesis starts at the center of the desired product and is progressively extended in both directions by using overlapping oligonucleotides that are homologous to the forward strand at the 5' end of the gene and against the reverse strand at the 3' end of the gene.

Another method of synthesizing a larger double stranded DNA fragment is to combine smaller oligonucleotides through top-strand PCR (TSP). In this method, a plurality of oligonucleotides spans the entire length of a desired product and contain overlapping regions to the adjacent oligonucleotide(s). Amplification can be performed with universal forward and reverse primers, and through multiple cycles of amplification a full-length double stranded DNA product is formed. This product can then undergo optional error correction and further amplification that results in the desired double stranded DNA fragment end product.

In one method of TSP, the set of smaller oligonucleotides that will be combined to form the full-length desired product are between 40-200 bases long and overlap each other by at least about 15-20 bases. For practical purposes, the overlap region should be at a minimum long enough to ensure specific annealing of oligonucleotides and have a high enough melting temperature ($T_m$) to anneal at the reaction temperature employed. The overlap can extend to the point where a given oligonucleotide is completely overlapped by adjacent oligonucleotides. The amount of overlap does not seem to have any effect on the quality of the final product. The first and last oligonucleotide building block in the assembly should contain binding sites for forward and reverse amplification primers. In one embodiment, the terminal end sequence of the first and last oligonucleotide contain the same sequence of complementarity to allow for the use of universal primers.

Assembling/Cloning Plasmids

In some embodiments, the present disclosure teaches methods for constructing vectors capable of inserting desired prokaryotic hemoglobin genes into the genome of host organisms. In some embodiments, the present disclosure teaches methods of cloning vectors comprising the insert DNA (e.g., prokaryotic hemoglobin gene), homology arms, and at least one selection marker (see FIG. 1).

In some embodiments, the present disclosure is compatible with any vector suited for transformation into the host organism. In some embodiments, the present disclosure teaches use of shuttle vectors compatible with a host cell. In one embodiment, a shuttle vector for use in the methods provided herein is a shuttle vector compatible with an *E. coli* and/or *Corynebacterium* host cell. Shuttle vectors for use in the methods provided herein can comprise markers for selection and/or counter-selection as described herein. The markers can be any markers known in the art and/or provided herein. The shuttle vectors can further comprise any regulatory sequence(s) and/or sequences useful in the assembly of said shuttle vectors as known in the art. The shuttle vectors can further comprise any origins of replication that may be needed for propagation in a host cell as provided herein such as, for example, *E. coli* or *C. glutamicum*. The regulatory sequence can be any regulatory sequence known in the art or provided herein such as, for example, a promoter, start, stop, signal, secretion and/or termination sequence of the genetic machinery of the host cell. The termination sequence can be SEQ ID NO: 20 or 21. In certain instances, the target DNA can be inserted into vectors, constructs or plasmids obtainable from any repository or catalogue product, such as a commercial vector (see e.g., DNA2.0 custom or GATEWAY® vectors).

In some embodiments, the assembly/cloning methods of the present disclosure may employ at least one of the following assembly strategies: 1) type II conventional cloning, ii) type II S-mediated or "Golden Gate" cloning (see, e.g., Engler, C., R. Kandzia, and S. Marillonnet. 2008 "A one pot, one step, precision cloning method with high throughput capability". PLos One 3:e3647; Kotera, I., and T. Nagai. 2008 "A high-throughput and single-tube recombination of crude PCR products using a DNA polymerase inhibitor and type IIS restriction enzyme." J Biotechnol 137:1-7; Weber, E., R. Gruetzner, S. Werner, C. Engler, and S. Marillonnet. 2011 Assembly of Designer TAL Effectors by Golden Gate Cloning. PloS One 6:e19722), iii) GATEWAY® recombination, iv) TOPO® cloning, exonuclease-mediated assembly (Aslandis and de Jong 1990. "Ligation-independent cloning of PCR products (LIC-PCR)." Nucleic Acids Research, Vol. 18, No. 20 6069), v) homologous recombination, vi) non-homologous end joining, or a combination thereof. Modular type IIS based assembly strategies are disclosed in PCT Publication WO 2011/154147, the disclosure of which is included herein by reference.

In some embodiments, the present disclosure teaches cloning vectors with at least one selection marker. Various selection marker genes are known in the art often encoding antibiotic resistance function for selection in prokaryotic (e.g., against ampicillin, kanamycin, tetracycline, chloramphenycol, zeocin, spectinomycin/streptomycin) or eukaryotic cells (e.g. geneticin, neomycin, hygromycin, puromycin, blasticidin, zeocin) under selective pressure. Other marker systems allow for screening and identification of wanted or unwanted cells such as the well-known blue/white screening system used in bacteria to select positive clones in the presence of X-gal or fluorescent reporters such as green or red fluorescent proteins expressed in successfully transduced host cells. Another class of selection markers most of which are only functional in prokaryotic systems relates to counter selectable marker genes often also referred to as "death genes" which express toxic gene products that kill producer cells. Examples of such genes include sacB, rpsL (strA), tetAR, pheS, thyA, gata-1, or ccdB, the function of which is described in (Reyrat et al. 1998 "Counterselectable Markers: Untapped Tools for Bacterial Genetics and Pathogenesis." Infect Immun. 66(9): 4011-4017).

In one embodiment, the vector into which the target DNA segment is cloned into comprises a promoter polynucleotide from a promoter ladder or library as provided herein. In one embodiment, provided herein is promoter ladder comprising or containing a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8. The promoter polynucleotide can be used in each case for overexpressing or under-expressing a prokaryotic hemoglobin gene in a host microorganism.

In some embodiments, each generated strain comprising a heterologous prokaryotic hemoglobin is cultured and analyzed under one or more criteria of the present disclosure (e.g., growth and/or productivity of a biomolecule or product of interest). Data from each of the analyzed host strains is associated/correlated with a particular prokaryotic hemoglobin and is recorded for future use. Thus, the present disclosure enables the creation of large and highly annotated genetic diversity libraries/depositories that identify the effect of a prokaryotic hemoglobin gene on any number of microbial genetic or phenotypic traits of interest.

In some embodiments, the present disclosure teaches the use of vectors for cloning the prokaryotic hemoglobin gene with start and/or stop codon variants such that the cloned gene utilizes the start and/or stop codon variant. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218).

In one embodiment, the methods of the provided disclosure comprise codon optimizing one or more genes expressed by the host organism. Methods for optimizing codons to improve expression in various hosts are known in the art and are described in the literature (see U.S. Pat. App. Pub. No. 2007/0292918, incorporated herein by reference in its entirety). Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence.

In some embodiments, a hemoglobin gene or polynucleotide provided herein comprises a molecule codon optimized for translation in a host cell provided herein, such as, for example, *E. coli* and/or *C. glutamicum*. The gene or polynucleotide can be an isolated, synthetic or recombinant nucleic acid. The codon optimized hemoglobin gene or polynucleotide can be selected from an organism listed in Table 2. The codon optimized hemoglobin gene or polynucleotide can be selected from SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 or SEQ ID NO: 20. In some cases, provided herein is a hemoglobin gene or polynucleotide that is codon optimized to encode a polypeptide sequence for a hemoglobin polypeptide selected from an organism listed in Table 2. In some cases, provided herein is a hemoglobin gene or polynucleotide that is codon optimized to encode a polypeptide sequence selected from SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 or SEQ ID NO: 34. The codon optimized hemoglobin gene or polynucleotide provided herein can be generated using a method known in the art for generating codon optimized polynucleotides such as, for example, GenScript's OptimumGene™ gene design system or DNA2.0 GeneGPS® Expression Optimization technology.

Protein expression is governed by a host of factors including those that affect transcription, mRNA processing, and stability and initiation of translation. Optimization can thus address any of a number of sequence features of any particular gene. As a specific example, a rare codon induced translational pause can result in reduced protein expression. A rare codon induced translational pause includes the presence of codons in the polynucleotide of interest that are rarely used in the host organism may have a negative effect on protein translation due to their scarcity in the available tRNA pool.

Alternate translational initiation also can result in reduced heterologous protein expression. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes eliminating putative internal RBS sequences from an optimized polynucleotide sequence.

Repeat-induced polymerase slippage can result in reduced heterologous protein expression. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage, includes altering extended repeats of G or C nucleotides.

Interfering secondary structures also can result in reduced heterologous protein expression. Secondary structures can sequester the RBS sequence or initiation codon and have been correlated to a reduction in protein expression. Stem-loop structures can also be involved in transcriptional pausing and attenuation. An optimized polynucleotide sequence can contain minimal secondary structures in the RBS and gene coding regions of the nucleotide sequence to allow for improved transcription and translation.

For example, the optimization process can begin by identifying the desired amino acid sequence to be expressed by the host. From the amino acid sequence a candidate polynucleotide or DNA sequence can be designed. During the design of the synthetic DNA sequence, the frequency of codon usage can be compared to the codon usage of the host expression organism and rare host codons can be removed from the synthetic sequence. Additionally, the synthetic candidate DNA sequence can be modified in order to remove undesirable enzyme restriction sites and add or remove any desired signal sequences, linkers or untranslated regions. The synthetic DNA sequence can be analyzed for the presence of secondary structure that may interfere with the translation process, such as G/C repeats and stem-loop structures.

Transformation of Host Cells

In some embodiments, the vectors of the present disclosure may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., 1986 "Basic Methods in Molecular Biology"). Other methods of transformation include for example, lithium acetate transformation and electroporation See, e.g., Gietz et al., Nucleic Acids Res. 27:69-74 (1992); Ito et al., J. Bacterol. 153:163-168 (1983); and Becker and Guarente, Methods in Enzymology 194:182-187 (1991). In some embodiments, transformed host cells are referred to as recombinant host strains.

In some embodiments, the present disclosure teaches high throughput transformation of cells using 96-well plate robotics platform and liquid handling machines known in the art.

In some embodiments, the present disclosure teaches screening transformed cells with one or more selection markers. In one such embodiment, cells transformed with a vector comprising a kanamycin resistance marker (KanR) are plated on media containing effective amounts of the kanamycin antibiotic. Colony forming units visible on kanamycin-laced media are presumed to have incorporated the vector cassette into their genome. Insertion of the desired sequences can be confirmed via PCR, restriction enzyme analysis, and/or sequencing of the relevant insertion site.

Looping Out of Selected Sequences

In some embodiments, the present disclosure teaches methods of looping out selected regions of DNA from the host organisms. The looping out method can be as described in Nakashima et al. 2014 "Bacterial Cellular Engineering by Genome Editing and Gene Silencing." Int. J. Mol. Sci. 15(2), 2773-2793. In some embodiments, the present disclosure teaches looping out selection markers from positive transformants. Looping out deletion techniques are known in the art, and are described in (Tear et al. 2014 "Excision of Unstable Artificial Gene-Specific inverted Repeats Mediates Scar-Free Gene Deletions in *Escherichia coli*." Appl. Biochem. Biotech. 175:1858-1867). The looping out methods used in the methods provided herein can be performed using single-crossover homologous recombination or double-crossover homologous recombination. In one embodiment, looping out of selected regions as described herein can entail using single-crossover homologous recombination as described herein.

Figure 2:
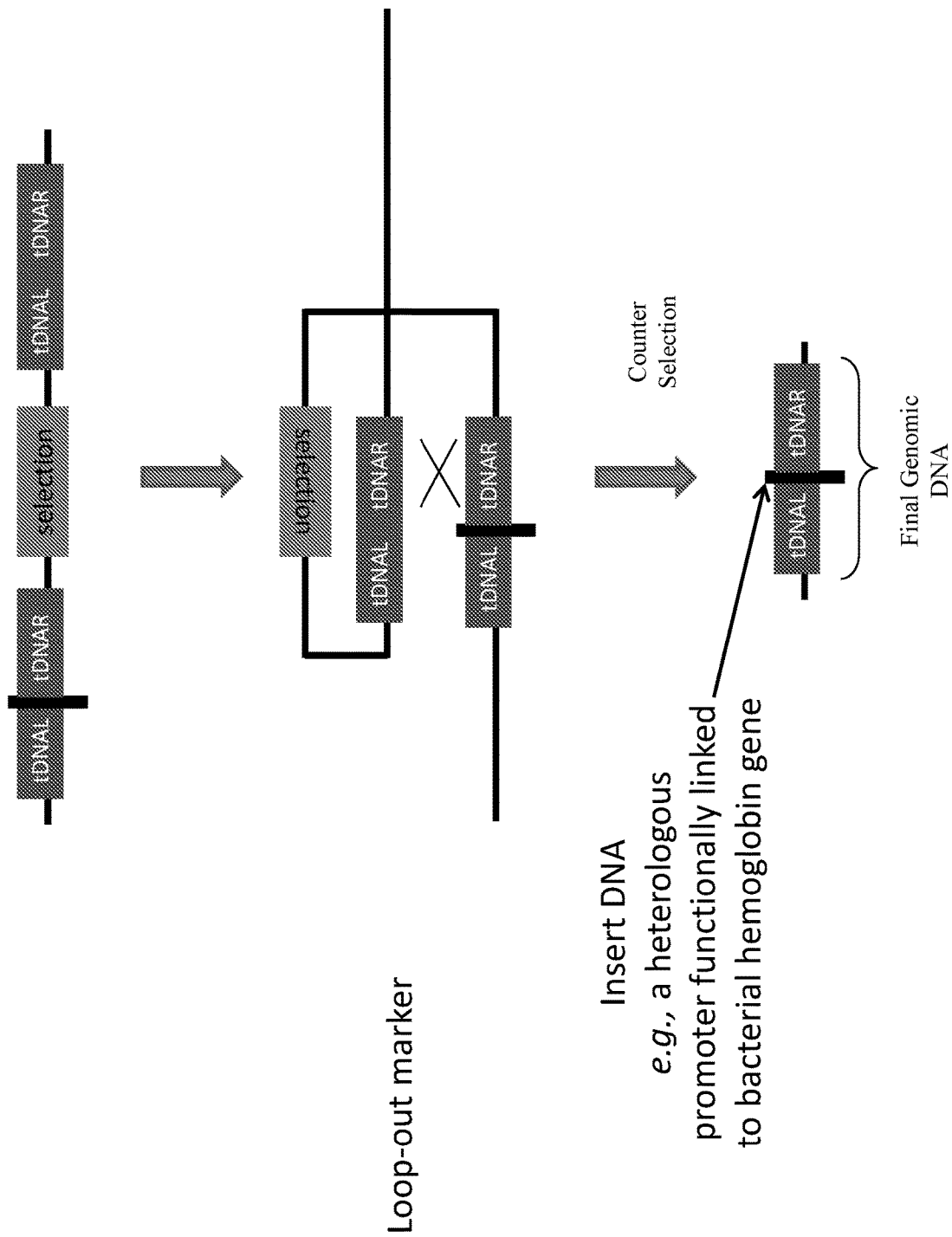
FIG. 2 illustrates a procedure for looping-out selected regions of DNA from host strains. Direct repeat (DR) regions of the inserted DNA form a loop with corresponding sequences in the host strain's genome. Cells counter selected for selection marker exhibit DNA deletion of loop DNA.

First, loop out vectors are inserted into selected target regions within the genome of the host organism (e.g., via homologous recombination, CRISPR, or other gene editing technique). In one embodiment, single-crossover homologous recombination is used between a circular plasmid or vector and the host cell genome in order to loop-in the circular plasmid or vector such as depicted in FIG. 1. The inserted vector can be designed with a sequence which is a direct repeat of an existing or introduced nearby host sequence, such that the direct repeats flank the region of DNA slated for looping and deletion. Once inserted, cells containing the loop out plasmid or vector can be counter selected for deletion of the selection region (e.g., see FIG. 2; lack of resistance to the selection gene).

Host Microorganisms

The genomic engineering methods provided herein are exemplified with industrial microbial cell cultures, but can be applicable to any organism where desired traits can be identified in a population of genetic mutants.

Thus, as used herein, the term "microorganism" should be taken broadly. It includes, but is not limited to, the two prokaryotic domains, Bacteria and Archaea, as well as certain eukaryotic fungi and protists. However, in certain aspects, "higher" eukaryotic organisms such as insects, plants, and animals can be utilized in the methods taught herein.

Suitable host cells include, but are not limited to: bacterial cells, algal cells, plant cells, fungal cells, insect cells, and mammalian cells. In one illustrative embodiment, suitable host cells include *E. coli* (e.g., SHuffle™ competent *E. coli* available from New England BioLabs in Ipswich, Mass.).

Other suitable host organisms of the present disclosure include microorganisms of the genus *Corynebacterium*. In some embodiments, preferred *Corynebacterium* strains/species include: *C. efficiens*, with the deposited type strain being DSM44549, *C. glutamicum*, with the deposited type strain being ATCC13032, and *C. ammoniagenes*, with the deposited type strain being ATCC6871. In some embodiments, the preferred host of the present disclosure is *C. glutamicum*.

Suitable host strains of the genus *Corynebacterium*, in particular of the species *Corynebacterium glutamicum*, are in particular the known wild-type strains: *Corynebacterium glutamicum* ATCC13032, *Corynebacterium acetoglutamicum* ATCC15806, *Corynebacterium acetoacidophilum* ATCC13870, *Corynebacterium melassecola* ATCC17965, *Corynebacterium thermoaminogenes* FERM BP-1539, *Brevibacterium flavum* ATCC14067, *Brevibacterium lactofermentum* ATCC13869, and *Brevibacterium divaricatum* ATCC14020; and L-amino acid-producing mutants, or strains, prepared therefrom, such as, for example, the L-lysine-producing strains: *Corynebacterium glutamicum* FERM-P 1709, *Brevibacterium flavum* FERM-P 1708, *Brevibacterium lactofermentum* FERM-P 1712, *Corynebacterium glutamicum* FERM-P 6463, *Corynebacterium glutamicum* FERM-P 6464, *Corynebacterium glutamicum* DM58-1, *Corynebacterium glutamicum* DG52-5, *Corynebacterium glutamicum* DSM5714, and *Corynebacterium glutamicum* DSM12866.

The term "*Micrococcus glutamicus*" has also been in use for *C. glutamicum*. Some representatives of the species *C. efficiens* have also been referred to as *C. thermoaminogenes* in the prior art, such as the strain FERM BP-1539, for example.

In some embodiments, the host cell of the present disclosure is a eukaryotic cell. Suitable eukaryotic host cells include, but are not limited to: fungal cells, algal cells, insect cells, animal cells, and plant cells. Suitable fungal host cells include, but are not limited to: *Ascomycota, Basidiomycota, Deuteromycota, Zygomycota, Fungi imperfecti*. Certain preferred fungal host cells include yeast cells and filamentous fungal cells. Suitable filamentous fungi host cells include, for example, any filamentous forms of the subdivision *Eumycotina* and *Oomycota*. (see, e.g., Hawksworth et al., In Ainsworth and Bisby's Dictionary of The Fungi, 8$^{th}$ edition, 1995, CAB International, University Press, Cambridge, UK, which is incorporated herein by reference). Filamentous fungi are characterized by a vegetative mycelium with a cell wall composed of chitin, cellulose and other complex polysaccharides. The filamentous fungi host cells are morphologically distinct from yeast.

In certain illustrative, but non-limiting embodiments, the filamentous fungal host cell may be a cell of a species of: *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella*, or teleomorphs, or anamorphs, and synonyms or taxonomic equivalents thereof.

Suitable yeast host cells include, but are not limited to: *Candida, Hansenula, Saccharomyces, Schizosaccharomyces, Pichia, Kluyveromyces*, and *Yarrowia*. In some embodiments, the yeast cell is *Hansenula polymorpha, Saccharomyces cerevisiae, Saccaromyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

In certain embodiments, the host cell is an algal such as, *Chlamydomonas* (e.g., *C. Reinhardtii*) and *Phormidium* (P. sp. ATCC29409).

In other embodiments, the host cell is a prokaryotic cell. Suitable prokaryotic cells include gram positive, gram negative, and gram-variable bacterial cells. The host cell may be a species of, but not limited to: *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia,* and *Zymomonas*. In some embodiments, the host cell is *Corynebacterium glutamicum*.

In some embodiments, the bacterial host strain is an industrial strain. Numerous bacterial industrial strains are known and suitable in the methods and compositions described herein.

In some embodiments, the bacterial host cell is of the *Agrobacterium* species (e.g., *A. radiobacter, A. rhizogenes, A. rubi*), the *Arthrobacter* species (e.g., *A. aurescens, A. citreus, A. globformis, A. hydrocarboglutamicus, A. mysorens, A. nicotianae, A. paraffineus, A. protophonniae, A. roseoparaffinus, A. sulfureus, A. ureafaciens*), the *Bacillus* species (e.g., *B. thuringiensis, B. anthracis, B. megaterium, B. subtilis, B. lentus, B. circulars, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens*. In some embodiments, the host cell will be an industrial *Clostridium* species (e.g., *C. acetobutylicum, C. tetani* E88, *C. lituseburense, C. saccharobutylicum, C. perfringens, C. beijerinckii*). In some embodiments, the host cell will be an industrial *Corynebacterium* species (e.g., *C. glutamicum, C. acetoacidophilum*). In some embodiments, the host cell will be an industrial *Escherichia* species (e.g., *E. coli*). In some embodiments, the host cell will be an industrial *Erwinia* species (e.g., *E. uredovora, E. carotovora, E. ananas, E. herbicola, E. punctata, E. terreus*). In some embodiments, the host cell will be an industrial *Pantoea* species (e.g., *P. citrea, P. agglomerans*). In some embodiments, the host cell will be an industrial *Pseudomonas* species, (e.g., *P. putida, P. aeruginosa, P. mevalonii*). In some embodiments, the host cell will be an industrial *Streptococcus* species (e.g., *S. equisimiles, S. pyogenes, S. uberis*). In some embodiments, the host cell will be an industrial *Streptomyces* species (e.g., *S. ambofaciens, S. achromogenes, S. avermitilis, S. coelicolor, S. aureofaciens, S. aureus, S. fungicidicus, S. griseus, S. lividans*). In some embodiments, the host cell will be an industrial *Zymomonas* species (e.g., *Z. mobilis, Z. lipolytica*), and the like.

In various embodiments, strains that may be used in the practice of the disclosure including both prokaryotic and eukaryotic strains, are readily accessible to the public from a number of culture collections such as American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

In some embodiments, the methods of the present disclosure are also applicable to multi-cellular organisms. For example, the platform could be used for improving the performance of crops. The organisms can comprise a plurality of plants such as *Gramineae, Fetucoideae, Poacoideae, Agrostis, Phleum, Dactylis, Sorgum, Setaria, Zea, Oryza, Triticum, Secale, Avena, Hordeum, Saccharum, Poa, Festuca, Stenotaphrum, Cynodon, Coix, Olyreae, Phareae, Compositae* or *Leguminosae*. For example, the plants can be corn, rice, soybean, cotton, wheat, rye, oats, barley, pea, beans, lentil, peanut, yam bean, cowpeas, velvet beans, clover, alfalfa, lupine, vetch, lotus, sweet clover, wisteria, sweet pea, sorghum, millet, sunflower, canola or the like. Similarly, the organisms can include a plurality of animals such as non-human mammals, fish, insects, or the like.

Cell Fermentation and Culture

Microorganisms of the present disclosure including those genetically engineered as described herein can be cultured in conventional nutrient media modified as appropriate for any desired biosynthetic reactions or selections. In some embodiments, the present disclosure teaches culture in inducing media for activating promoters. In some embodiments, the present disclosure teaches media with selection agents, including selection agents of transformants (e.g., antibiotics), or selection of organisms suited to grow under inhibiting conditions (e.g., high ethanol conditions). In some embodiments, the present disclosure teaches growing cell cultures in media optimized for cell growth. In other embodiments, the present disclosure teaches growing cell cultures in media optimized for product yield such as, for example, products or biomolecules of interest. In some embodiments, the present disclosure teaches growing cultures in media capable of inducing cell growth and also contains the necessary precursors for final product production (e.g., high levels of sugars for ethanol production). The biomolecules or products of interest produced by the methods provided herein can be any commercial product produced from microbes. In some cases, the biomolecule or product of interest is a pharmaceutical, small molecule, an amino acid, a nucleotide, an organic acid, or an alcohol. The amino acid can be glutamic acid, tyrosine, phenylalanine, tryptophan, aspartic acid, asparagine, threonine, isoleucine, methionine, or lysine. The organic acid can be succinate, lactate or pyruvate. The alcohol can be ethanol or isobutanol.

Culture conditions, such as temperature, pH and the like, are those suitable for use with the host cell selected for expression, and will be apparent to those skilled in the art. As noted, many references are available for the culture and production of many cells, including cells of bacterial, plant, animal (including mammalian) and archebacterial origin. See e.g., Sambrook, Ausubel (all supra), as well as Berger, *Guide to Molecular Cloning Techniques, Methods in Enzymology* volume 152 Academic Press, Inc., San Diego, Calif.; and Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelle et al., (1989) *In Vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* from Sigma-Aldrich, Inc (St Louis, Mo.) ("Sigma-LSRCCC") and, for example, *The Plant Culture Catalogue* and supplement also from Sigma-Aldrich, Inc (St Louis, Mo.) ("Sigma-PCCS"), all of which are incorporated herein by reference.

The culture medium or fermentation medium to be used must in a suitable manner satisfy the demands of the respective strains. Descriptions of culture media for various microorganisms are present in the "Manual of Methods for General Bacteriology" of the American Society for Bacteriology (Washington D.C., USA, 1981). The terms culture medium and fermentation medium are interchangeable. In some cases, the levels of oxygen provided in the culture medium or fermentation medium for growing a genetically modified strain produced by the methods provided herein can be less than for a wildtype strain or a strain that does not express a heterologous hemoglobin gene provided herein.

In some embodiments, the present disclosure teaches that the microorganisms produced may be cultured continuously—as described, for example, in WO 05/021772—or discontinuously in a batch process (batch cultivation) or in a fed-batch or repeated fed-batch process for the purpose of producing the desired biomolecule or product of interest. A summary of a general nature about known cultivation methods is available in the textbook by Chmiel (BioprozeStechnik. 1: Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

In some embodiments, the cells of the present disclosure are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present disclosure. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is a system where a defined fermentation medium is added continuously to a bioreactor and an equal amount of conditioned medium is removed simultaneously for processing and harvesting of desired proteins. In some embodiments, continuous fermentation generally maintains the cultures at a constant high density where cells are primarily in log phase growth. In some embodiments, continuous fermentation generally maintains the cultures at a stationary or late log/stationary, phase growth. Continuous fermentation systems strive to maintain steady state growth conditions.

Methods for modulating nutrients and growth factors for continuous fermentation processes as well as techniques for maximizing the rate of product formation are well known in the art of industrial microbiology.

For example, a non-limiting list of carbon sources for the cultures of the present disclosure include, sugars and carbohydrates such as, for example, glucose, xylose, sucrose, lactose, fructose, maltose, molasses, sucrose-containing solutions from sugar beet or sugar cane processing, starch, starch hydrolysate, and cellulose; oils and fats such as, for example, soybean oil, sunflower oil, groundnut oil and coconut fat; fatty acids such as, for example, palmitic acid, stearic acid, and linoleic acid; alcohols such as, for example, glycerol, methanol, and ethanol; and organic acids such as, for example, acetic acid or lactic acid.

A non-limiting list of the nitrogen sources for the cultures of the present disclosure include, organic nitrogen-containing compounds such as peptones, yeast extract, meat extract, malt extract, corn steep liquor, soybean flour, and urea; or inorganic compounds such as ammonium sulfate, ammonium chloride, ammonium phosphate, ammonium carbonate, and ammonium nitrate. The nitrogen sources can be used individually or as a mixture.

A non-limiting list of the possible phosphorus sources for the cultures of the present disclosure include phosphoric acid, potassium dihydrogen phosphate or dipotassium hydrogen phosphate or the corresponding sodium-containing salts. The culture medium may additionally comprise salts, for example in the form of chlorides or sulfates of metals such as, for example, sodium, potassium, magnesium, calcium and iron, such as, for example, magnesium sulfate or iron sulfate, which are necessary for growth. Finally, essential growth factors such as amino acids, for example homoserine and vitamins, for example thiamine, biotin or pantothenic acid, may be employed in addition to the abovementioned substances.

In some embodiments, the pH of the culture can be controlled by any acid or base, or buffer salt, including, but not limited to sodium hydroxide, potassium hydroxide, ammonia, or aqueous ammonia; or acidic compounds such as phosphoric acid or sulfuric acid in a suitable manner. In some embodiments, the pH is generally adjusted to a value of from 6.0 to 8.5, preferably 6.5 to 8.

In some embodiments, the cultures of the present disclosure may include an anti-foaming agent such as, for example, fatty acid polyglycol esters. In some embodiments the cultures of the present disclosure are modified to stabilize the plasmids of the cultures by adding suitable selective substances such as, for example, antibiotics.

In some embodiments, the culture is carried out under aerobic conditions. In order to maintain these conditions, oxygen or oxygen-containing gas mixtures such as, for example, air are introduced into the culture. It is likewise possible to use liquids enriched with hydrogen peroxide. The fermentation is carried out, where appropriate, at elevated pressure, for example at an elevated pressure of from 0.03 to 0.2 MPa. The temperature of the culture is normally from 20° C. to 45° C. and preferably from 25° C. to 40° C., particularly preferably from 30° C. to 37° C. In batch or fed-batch processes, the cultivation is preferably continued until an amount of the desired organic-chemical compound sufficient for being recovered has formed. In some embodiments, the culture is carried out under anaerobic conditions.

Product Recovery and Quantification

Methods for screening for the production of products of interest are known to those of skill in the art and are discussed throughout the present specification. Such methods may be employed when screening the strains of the disclosure. The biomolecules or products of interest produced by the methods provided herein can be any commercial product produced from glucose or any feedstock or source of energy. In some cases, the biomolecule or product of interest is a pharmaceutical, an amino acid, a nucleotide, an organic acid, or an alcohol. The amino acid can be glutamic acid, tyrosine, phenylalanine, tryptophan, aspartic acid, asparagine, threonine, isoleucine, methionine, or lysine. The organic acid can be succinate, lactate or pyruvate. The alcohol can be ethanol or isobutanol.

In some embodiments, the present disclosure teaches methods of improving strains designed to produce non-secreted intracellular products. For example, the present disclosure teaches methods of improving the robustness, yield, efficiency, or overall desirability of cell cultures producing intracellular enzymes, oils, pharmaceuticals, or other valuable small molecules or peptides. The recovery or isolation of non-secreted intracellular products can be achieved by lysis and recovery techniques that are well known in the art, including those described herein.

For example, in some embodiments, cells of the present disclosure can be harvested by centrifugation, filtration, settling, or other method. Harvested cells are then disrupted by any convenient method, including freeze-thaw cycling, sonication, mechanical disruption, or use of cell lysing agents, or other methods, which are well known to those skilled in the art.

The resulting product of interest, e.g. a polypeptide, may be recovered/isolated and optionally purified by any of a number of methods known in the art. For example, a product polypeptide may be isolated from the nutrient medium by conventional procedures including, but not limited to: centrifugation, filtration, extraction, spray-drying, evaporation, chromatography (e.g., ion exchange, affinity, hydrophobic interaction, chromatofocusing, and size exclusion), or precipitation. Finally, high performance liquid chromatography (HPLC) can be employed in the final purification steps. (See for example Purification of intracellular protein as described in Parry et al., 2001, *Biochem. J.* 353:117, and Hong et al., 2007, *Appl. Microbiol. Biotechnol.* 73:1331, both incorporated herein by reference).

In addition to the references noted supra, a variety of purification methods are well known in the art, including, for example, those set forth in: Sandana (1997) *Bioseparation of Proteins*, Academic Press, Inc.; Bollag et al. (1996) *Protein Methods*, $2^{nd}$ Edition, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice* $3^{rd}$ Edition, Springer Verlag, NY; Janson and Ryden (1998) *Protein Purification: Principles, High Resolution Methods and Applications*, Second Edition, Wiley-VCH, NY; and Walker (1998) *Protein Protocols on CD-ROM*, Humana Press, NJ; all of which are incorporated herein by reference.

In some embodiments, the present disclosure teaches the methods of improving strains designed to produce secreted products. For example, the present disclosure teaches methods of improving the robustness, yield, efficiency, or overall desirability of cell cultures producing valuable small molecules or peptides.

In some embodiments, immunological methods may be used to detect and/or purify secreted or non-secreted products produced by the cells of the present disclosure. In one example approach, antibody raised against a product molecule (e.g., against an insulin polypeptide or an immunogenic fragment thereof) using conventional methods is immobilized on beads, mixed with cell culture media under conditions in which the endoglucanase is bound, and precipitated. In some embodiments, the present disclosure teaches the use of enzyme-linked immunosorbent assays (ELISA).

In other related embodiments, immunochromatography is used, as disclosed in U.S. Pat. Nos. 5,591,645, 4,855,240, 4,435,504, 4,980,298, and Se-Hwan Paek, et al., "Development of rapid One-Step Immunochromatographic assay, Methods", 22, 53-60, 2000), each of which are incorporated by reference herein. A general immunochromatography detects a specimen by using two antibodies. A first antibody exists in a test solution or at a portion at an end of a test piece in an approximately rectangular shape made from a porous membrane, where the test solution is dropped. This antibody is labeled with latex particles or gold colloidal particles (this antibody will be called as a labeled antibody hereinafter). When the dropped test solution includes a specimen to be detected, the labeled antibody recognizes the specimen so as to be bonded with the specimen. A complex of the specimen and labeled antibody flows by capillarity toward an absorber, which is made from a filter paper and attached to an end opposite to the end having included the labeled antibody. During the flow, the complex of the specimen and labeled antibody is recognized and caught by a second antibody (it will be called as a tapping antibody hereinafter) existing at the middle of the porous membrane and, as a result of this, the complex appears at a detection part on the porous membrane as a visible signal and is detected.

In some embodiments, the screening methods of the present disclosure are based on photometric detection techniques (absorption, fluorescence). For example, in some embodiments, detection may be based on the presence of a fluorophore detector such as GFP bound to an antibody. In other embodiments, the photometric detection may be based on the accumulation on the desired product from the cell culture. In some embodiments, the product may be detectable via UV of the culture or extracts from said culture.

In some embodiments, the product recovery methods allow for the quantitative determination of the effect on performance of each candidate prokaryotic hemoglobin gene. In some embodiments, the product recovery methods allow for the quantitative determination of the effect on performance of each candidate prokaryotic hemoglobin gene and selection for microorganisms expressing candidate prokaryotic hemoglobin genes that facilitate optimal growth and/or productivity rates of desired biomolecules or products of interest. In some embodiments, the methods provided herein allow for the selection of microorganisms or strains of microorganisms expressing a candidate heterologous prokaryotic hemoglobin gene (e.g., bacterial hemoglobin gene) that produces a concentration of intracellular hemoglobin greater than 0 and less than 125 nmoles per gram wet weight of cells. In some embodiments, the methods provided herein allow for the selection of microorganisms or strains of microorganisms expressing a candidate heterologous prokaryotic hemoglobin gene (e.g., bacterial hemoglobin gene) that produces a concentration of intracellular hemoglobin greater than 0 and less than 100 nmoles per gram wet weight of cells. In some embodiments, the methods provided herein allow for the selection of microorganisms or strains of microorganisms expressing a candidate heterologous prokaryotic hemoglobin gene (e.g., bacterial hemoglobin gene) that produces a concentration of intracellular hemoglobin greater than 0 and less than 75 nmoles per gram wet weight of cells.

Selection Criteria and Goals

The selection of a particular strain of host cell expressing a heterologous prokaryotic hemoglobin gene (e.g., bacterial hemoglobin gene) can be based on specific goals. For example, in some embodiments, the program goal may be to maximize single batch yields of reactions with no immediate time limits. In other embodiments, the program goal may be to rebalance biosynthetic yields to produce a specific product, or to produce a particular ratio of products. In some embodiments, the program goal may be to improve performance characteristics such as yield, titer, productivity, by-product elimination, tolerance to process excursions, optimal growth temperature and growth rate. In some embodiments, the program goal is improved host performance as measured by volumetric productivity, specific productivity, yield or titre, of a product of interest produced by a microbe. In some embodiments, the program goal is to provide microorganisms or strains of microorganisms that produce a concentration of intracellular hemoglobin greater than 0 and less than 125 nmoles per gram wet weight of cells. In some embodiments, the program goal is to provide microorganisms or strains of microorganisms that produce a concentration of intracellular hemoglobin greater than 0 and less than 100 nmoles per gram wet weight of cells. In some embodiments, the program goal is to provide microorganisms or strains of microorganisms that produce a concentration of intracellular hemoglobin greater than 0 and less than 75 nmoles per gram wet weight of cells.

In some embodiments, the program goal is to provide genetically modified host microorganisms or strains of host microorganisms that grow under low levels of oxygen (oxygen limitation). In some embodiments, the program goal is to provide genetically modified host microorganisms or strains of host microorganisms that grow under conditions of oxidative or nitrosative stress. The growth can be increased vs wildtype strains of the host microorganism. The growth can be increased vs. strains of the host microorganism not genetically modified to express a heterologous prokaryotic hemoglobin gene. In some embodiments, the host microorganism or strain of host microorganism of the present disclosure genetically modified to express a prokaryotic hemoglobin gene exhibit at least or about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10% or 5% more growth under oxidative stress, nitrosative stress, or oxygen limitation conditions than a control or reference. The control or reference can be a wildtype strain of the host microorganism or a host microorganism not genetically modified to express a heterologous prokaryotic hemoglobin gene.

In other embodiments, the program goal may be to optimize synthesis efficiency of a commercial strain in terms of final product yield per quantity of inputs (e.g., total amount of ethanol produced per pound of sucrose). In other embodiments, the program goal may be to optimize synthesis speed, as measured for example in terms of batch completion rates, or yield rates in continuous culturing systems. In one embodiment, the program goal is to optimize final product yield and/or production rate of a biomolecule or product of interest. The biomolecules or products of interest produced by the methods provided herein can be any commercial product produced from glucose microbe or microorganism. In some cases, the biomolecule or product of interest is a pharmaceutical, a small molecule, an amino acid, a nucleotide, an organic acid, or an alcohol. The amino acid can be glutamic acid, tyrosine, phenylalanine, tryptophan, aspartic acid, asparagine, threonine, isoleucine, methionine, or lysine. The organic acid can be succinate, lactate or pyruvate. The alcohol can be ethanol or isobutanol.

Persons having ordinary skill in the art will recognize how to tailor strain selection criteria to meet the particular project goal. For example, selections of a strain's single batch max yield at reaction saturation may be appropriate for identifying strains with high single batch yields. Selection based on consistency in yield across a range of temperatures and conditions may be appropriate for identifying strains with increased robustness and reliability.

In some embodiments, the selection criteria for the initial phase and the tank-based validation will be identical. In other embodiments, tank-based selection may operate under additional and/or different selection criteria.

EXAMPLES

The present disclosure is further illustrated by reference to the following Examples. However, it should be noted that these Examples, like the embodiments described above, is illustrative and is not to be construed as restricting the scope of the disclosure in any way.

Example 1

Transformation of *Corynebacterium* with Bacterial Hemoglobin Library Generation of Bacterial Hemoglobin Libraries A number of bacterial hemoglobin were selected for generation of a bacterial hemoglobin library using a computer based method employing an algorithm designed to search for sequence similarities between a specific bacterial hemoglobin and candidate bacterial hemoglobins. More specifically, the amino acid sequence of the hemoglobin from *Vitreoscilla stercocaria* was used to seed a TREMBL protein database search using the BLAST algorithm. All sequences that matched to within a certain similarity (i.e., BLAST E-value of 5) to the seeded hemoglobin were pulled from the database. Pairwise alignment between each sequence in the set was then conducted so that a similarity score associating each sequence with any other sequence in the set was generated. This was done using the online tool available at http://efi.igb.illinois.edu/efi-est/. An organic clustering algorithm was then deployed using the software tool Cytoscape (cytoscape.org) to sub-group members of the set into groups that were more or less similar. Representative candidates from each subgroup were selected so as to maximize the diversity of the sequences that were present in the library, with the hope that sequence diversity corresponded with functional diversity.

The bacterial hemoglobin genes that encode the bacterial hemoglobins selected for inclusion in the library were codon optimized using DNA2.0 GeneGPS® Expression Optimization technology. As such, the bacterial hemoglobin genes selected for inclusion in the library were the bacterial hemoglobin genes: Vhb01 (*Vitreoscilla stercoraria*; SEQ ID NO: 9),Vhb02 (*Gordonia terrae* C-6; SEQ ID NO: 10), Vhb03 (*Sandaracinus amylolyticus*; SEQ ID NO: 11), Vhb04 (*Fischerella* sp. JSC-11; SEQ ID NO: 12), Vhb05 (*Candidatus Entotheonella* sp. TSY1; SEQ ID NO:13), Vhb06 (*Hassallia byssoidea* VB512170; SEQ ID NO: 14), Vhb07 (mine drainage metagenome; SEQ ID NO: 15), Vhb08 (*Aeromonas molluscorum* 848; SEQ ID NO: 16), Vhb09 (*Phaeobacter gallaeciensis* DSM 26640; SEQ ID NO: 17), Vhb10 (*Spirosoma radiotolerans*; SEQ ID NO:

18), Vhb11 (*Shewanella loihica* (strain ATCC BAA-1088/ PV-4); SEQ ID NO: 19) and Vhb12 (*Sulfurimonas gotlandica* (strain DSM 19862/JCM 16533/GD1); SEQ ID NO: 20).

For generation of the hemoglobin library, each codon optimized hemoglobin gene described above was sequenced to ensure sequence integrity and subsequently cloned into a *C. glutamicum/Escherichia coli* compatible expression vector using type IIs restriction and ligation cloning techniques. In addition, within each hemoglobin construct, a P1 promoter (SEQ ID NO: 1) was cloned in front of the respective hemoglobin gene. Finally, each hemoglobin gene in a construct ended with a termination sequence (SEQ ID NO: 21).

Transformation of Assembled Clones into *E. coli*

Vectors containing the codon optimized hemoglobin genes were verified by sequencing and subsequently each individually transformed into *E. coli* in order to identify correctly assembled clones, and to amplify vector DNA for *Corynebacterium* transformation. Amplified DNA was validated via PCR/sequencing. Positive clones were saved at −20° C. fridge for future use.

Transformation of Assembled Clones into *Corynebacterium*

Validated clones were then individually transformed into *Corynebacterium glutamicum* host cells via electroporation. In order to test the effect of strain background on construct performance, three different strain backgrounds (i.e., context 1, context 2, and context 3 in FIG. 3A-3B) of *C. glutamicum* were used with each construct being transformed into each background. Each vector was designed to integrate into a neutral integration site within the *C. glutamicum* genome that was empirically determined to permit expression of the heterologous hemoglobin genes but not be detrimental to the host cell. To facilitate integration, the expression vector further comprised about 4 kb of sequence homologous (i.e., homology arms) to the desired integration site whereby each hemoglobin gene cassette described above was inserted between 2 kb of sequence homologous to the desired integration site on either side. Integration into the genome occurred by single-crossover integration and then loop-out of the plasmid backbone facilitated by counter-selection on a second marker included in the plasmid backbone.

Transformed bacteria were then tested for assembly success (correct integration into the genome). Colonies from each *Corynebacterium* transformation plate were cultured and tested for correct integration via PCR. This process was repeated for each of the transformations conducted for each bacterial hemoglobin construct. Genomic integration of each transformation was also analyzed with respect to the targeted genome location for each plasmid.

Evaluation of Individual Bacterial Hemoglobin Constructs in *Corynebacterium*

The phenotype of each transformant was then tested in an evaluation method designed to mimic or simulate a specific fermentation process for producing a desired fermentation end product in order to determine the effects the expression of each construct in each host cell background had on the desired phenotype (i.e., improved ability to produce a desired fermentation end product). Briefly, the evaluation method was an experiment where the transformants were cultured in a 96 well plate format under conditions that were meant to mimic fermentation conditions. The amount of product and biomass formed at various time points was measured and used to predict how each strain would perform under fermentation conditions. This prediction was a linear regression generated from testing strains with various fermentation performance in the evaluation method and determining the correlation of measurements to performance.

Figure 3A:
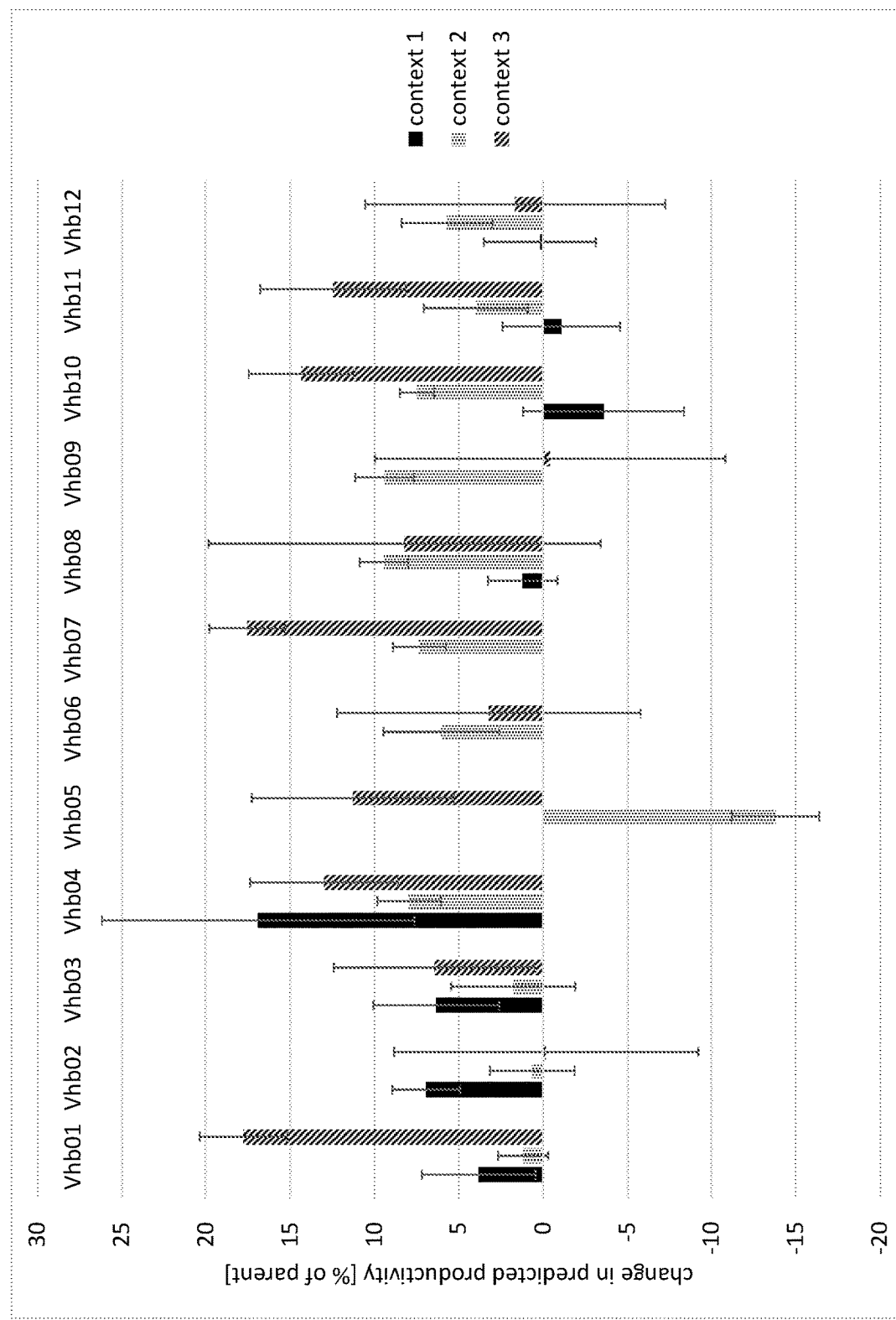
FIGS. 3A-3B illustrates performance of heterologous bacterial hemoglobin genes in an evaluation method as described in Example 1.
Figure 3B:
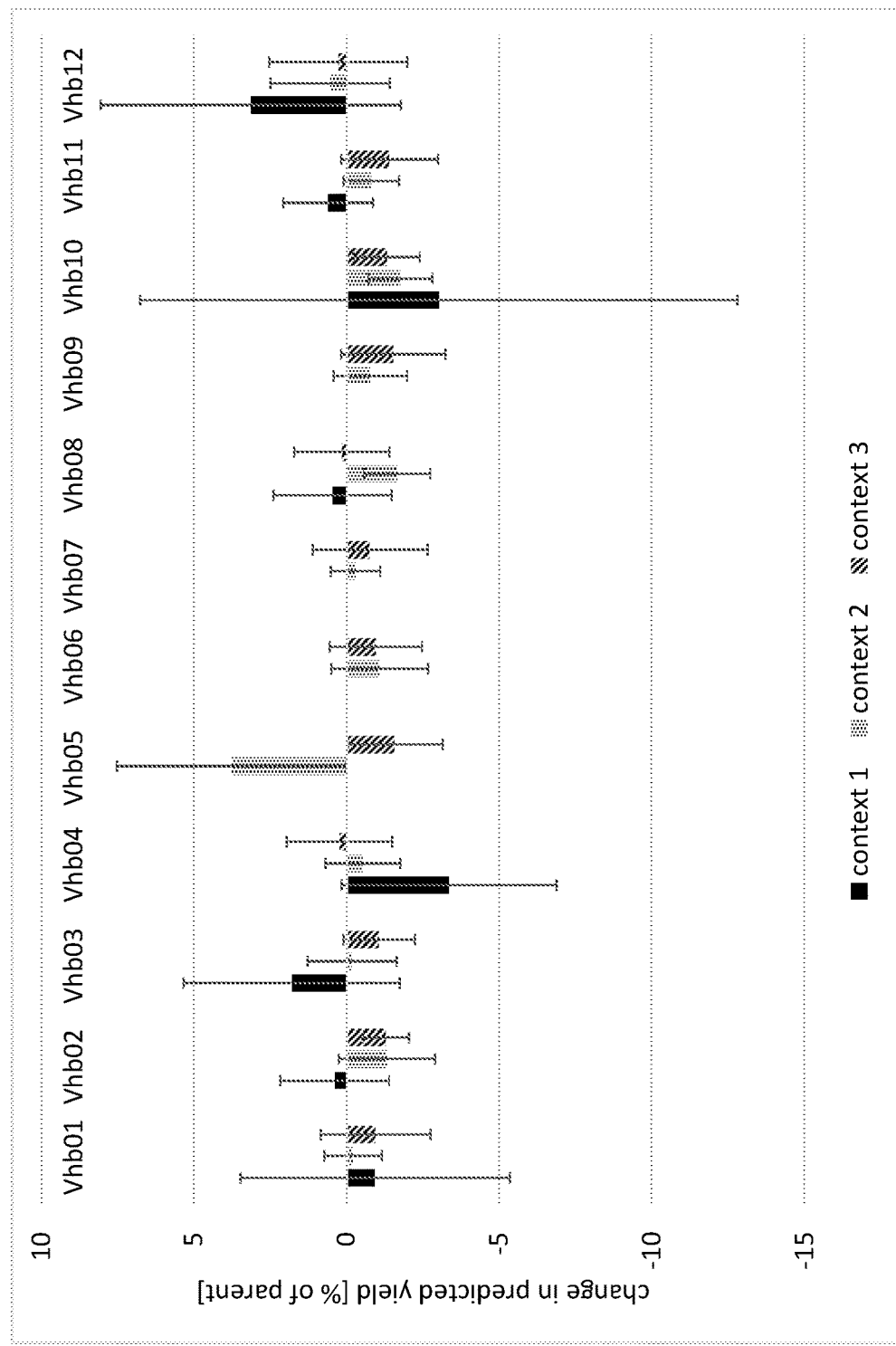

The predicted rate of production and yield of the desired fermentation end product was determined for each hemoglobin transformant, some examples of which are shown in FIGS. 3A-3B. As shown in FIG. 3A, for the specific hemoglobin inserts shown, the productivity in a fermentation process was predicted to generally increase in each context (i.e., host background) for each hemoglobin insert shown vs. the parent strain, except for a couple of specific hemoglobin/ background combinations (i.e., Vhb05 in combination with context 1 and 2; Vhb10 and Vhb11 in combination with context 1). Strains expressing Vhb04 showed an increase in predicted productivity as a % of parent strain in each context tested. In contrast, as shown in FIG. 3B, the predicted yield was much more variable with respect to hemoglobin insert in combination with context vs. the parent strain. In summary, in general, the hemoglobin genes had an effect on productivity but a much less significant effect on yield. Strains expressing Vhb04 showed a similar predicted yield as a % of parent strain in each context tested.

Assessment of Individual Bacterial Hemoglobin Constructs Under Fermentation Conditions Following evaluation as described above, transformants with heterologous hemoglobin genes with predicted increased performance (i.e., increased predicted productivity and/or predicted yield) were selected and subsequently grown in medium under conditions designed to facilitate fermentation and the production of desired fermentation end products. Following growth of each transformant for a predetermined length of time under fermentation conditions designed to produce a desired end-product, the yield and volumetric productivity of the end-product for each transformant was then determined. Briefly, high-performance liquid chromatography (HPLC) was used to determine the amount of product (i.e., avg yield) produced for a certain amount of substrate fed. Productivity (i.e., avg productivity) was similarly determined with the addition of time and volume data.

Figure 4:
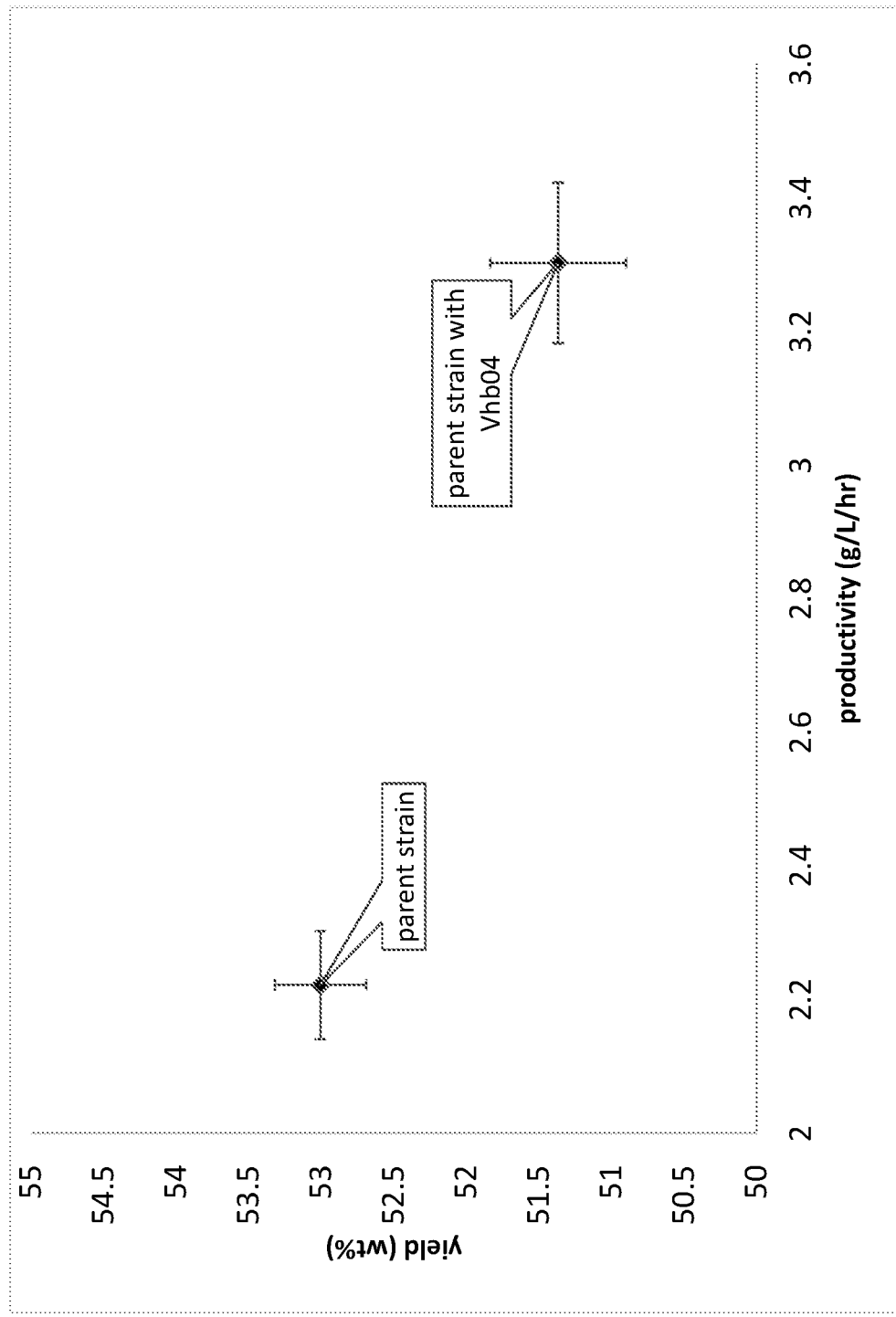
FIG. 4 illustrates performance of heterologous bacterial hemoglobin gene in desired fermentation conditions as described in Example 1.

As shown in FIG. 4, the Vhb04 construct increased productivity of the parent strain vs. the parent strain alone but showed a reduced yield. Accordingly, this example shows that the methods provided herein can be used to increase the performance of microbial strains in terms of producing fermentation end products.

Example 2

Transformation of *Corynebacterium* with Heterologous Bacterial Hemoglobin Construct: Assessment of Vhb01 Expressing *Corynebacteria* Transformants Grown Under Fermentation Conditions to Produce a Second Fermentation End Product As a follow-up to Example 1, following evaluation as described above, transformants heterologously expressing Vhb01 with predicted increased performance (i.e., increased predicted productivity and/or predicted yield) were selected and subsequently grown in medium under conditions designed to facilitate fermentation and the production of a second desired fermentation end product that was separate and distinct from the end product examined in Example 1. Following growth of each transformant for a predetermined length of time under fermentation conditions designed to produce the desired second end-product, the yield and volumetric productivity of the end-product for each transformant was then determined. Briefly, high-performance liquid chromatography (HPLC) was used to determine the amount of product (i.e., avg yield) produced for a certain amount of substrate fed. Productivity (i.e., avg productivity) was similarly determined with the addition of time and volume data.

The Vhb01 construct exhibited a 20% improvement in the productivity of the second fermentation product relative to Corynebacteria which did not contain the heterologous Vhb01 construct. Accordingly, this example shows that the methods provided herein can be used to increase the performance of microbial strains in terms of producing multiple fermentation end products.

INCORPORATION BY REFERENCE

The following applications are hereby incorporated by reference in their entirety, including all descriptions, references, figures, and claims for all purposes: U.S. application Ser. No. 15/396,230, filed on Dec. 30, 2016; International Application No. PCT/US2016/065465, filed on Dec. 7, 2016; U.S. application Ser. No. 15/140,296, filed on Apr. 27, 2016; U.S. Provisional Application No. 62/368,786, filed on Jul. 29, 2016; and U.S. Provisional Application No. 62/264,232, filed on Dec. 7, 2015.

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A host cell comprising a heterologous bacterial hemoglobin gene functionally linked to a first promoter polynucleotide, wherein the first promoter polynucleotide comprises a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

2. The host cell of claim 1, wherein the bacterial hemoglobin gene is a gene with a nucleotide sequence selected from SEQ ID NO: 12, SEQ ID NO: 10, SEQ ID NO: 11, SEQ ID NO: 9, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

3. The host cell of claim 1, wherein the bacterial hemoglobin gene encodes a polypeptide with an amino acid sequence selected from SEQ ID NO: 26, SEQ ID NO: 24, SEQ ID NO: 25, SEQ ID NO: 23, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

4. The host cell of claim 1, wherein the host cell is *Corynebacterium glutamicum*.

5. A method of producing a biomolecule comprising culturing the host cell of claim 1 under conditions suitable for producing the biomolecule.

6. A method for generating a microorganism capable of increased production of a biomolecule, the method comprising:
   a) genetically modifying a host microorganism, wherein the modifying comprises introducing a bacterial hemoglobin gene from a library of bacterial hemoglobin genes into the genome of the host microorganism, wherein each bacterial hemoglobin gene from the library of bacterial hemoglobin genes is functionally linked to a promoter comprising a nucleotide sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8 and wherein the modification generates a strain of the host microorganism expressing the bacterial hemoglobin gene;

b) repeating step a) for a plurality of rounds until a plurality of strains of the host microorganism are generated, wherein each strain of the plurality of strains of the host microorganism expresses a separate bacterial hemoglobin gene from the library of bacterial hemoglobin genes;

c) contacting each strain of the plurality of strains of the host microorganism with a carbon source under fermentative conditions; and d) selecting each strain of the host microorganism that produces an increased amount of a biomolecule as compared to the amount of the biomolecule produced from a control microorganism, wherein the control microorganism does not express a bacterial hemoglobin gene from the library of bacterial hemoglobin genes.

7. The method of claim 6, wherein the library of bacterial hemoglobin genes comprises one or more bacterial hemoglobin genes with a nucleotide sequence selected from SEQ ID NO: 12, SEQ ID NO: 10, SEQ ID NO: 11, SEQ ID NO: 9, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

8. The method of claim 6, wherein the library of bacterial hemoglobin genes comprises one or more bacterial hemoglobin genes that encode one or more polypeptide sequences selected from SEQ ID NO: 26, SEQ ID NO: 24, SEQ ID NO: 25, SEQ ID NO: 23, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

9. The method of claim 6, wherein the library of bacterial hemoglobin genes comprises one or more bacterial hemoglobin genes from a strain, species, or sub-species of a microorganism listed in Table 2.

10. The method of claim 6, wherein the library of bacterial hemoglobin genes comprises one or more bacterial flavohemoglobin genes from a strain, species, or sub-species of a microorganism listed in Table 2.

11. The method of claim 6, wherein the library of bacterial hemoglobin genes comprises one or more bacterial hemoglobin genes from a strain, species, or sub-species of a microorganism listed in Table 2 and one or more bacterial flavohemoglobin genes from a strain, species, or sub-species of a microorganism listed in Table 2.

12. The method of claim 6, wherein the host microorganism is *Corynebacterium glutamicum*.

13. A library of bacterial hemoglobin genes, wherein each bacterial hemoglobin gene in the library of bacterial hemoglobin genes is functionally linked to a promoter comprising a nucleotide sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

14. The library of claim 13, wherein the library of bacterial hemoglobin genes comprises one or more bacterial hemoglobin genes selected from SEQ ID NO: 12, SEQ ID NO: 10, SEQ ID NO: 11, SEQ ID NO: 9, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

15. The library of claim 13, wherein the library of bacterial hemoglobin genes comprises one or more bacterial hemoglobin genes that encode one or more polypeptide sequences selected from SEQ ID NO: 26, SEQ ID NO: 24, SEQ ID NO: 25, SEQ ID NO: 23, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

16. The library of claim 13, wherein the library of bacterial hemoglobin genes comprises one or more bacterial hemoglobin genes from a strain, species, or sub-species of a microorganism listed in Table 2.

17. The library of claim 13, wherein the library of bacterial hemoglobin genes comprises one or more bacterial flavohemoglobin genes from a strain, species, or sub-species of a microorganism listed in Table 2.

18. The library of claim 13, wherein the library of bacterial hemoglobin genes comprises one or more bacterial hemoglobin genes from a strain, species, or sub-species of a microorganism listed in Table 2 and one or more bacterial flavohemoglobins genes from a strain, species, or sub-species of a microorganism listed in Table 2.

19. A method of producing a biomolecule comprising introducing a bacterial hemoglobin gene from the library of claim 13 into a host cell and culturing the host cell under conditions suitable for producing the biomolecule.

20. The method of claim 19, wherein the host cell is *Corynebacterium glutamicum*.

* * * * *